(12) United States Patent
Bassett et al.

(10) Patent No.: US 12,383,659 B2
(45) Date of Patent: Aug. 12, 2025

(54) HIGH STRENGTH POROUS MATERIALS INCORPORATING WATER SOLUBLE POLYMERS

(71) Applicant: Access Vascular, Inc., Billerica, MA (US)

(72) Inventors: Michael Bassett, Hampton, NH (US); James F. Biggins, Waltham, MA (US); Daniel T. Donahue, Cambridge, MA (US); Matthew M. Mannarino, Burlington, MA (US)

(73) Assignee: Access Vascular, Inc., Billerica, MA (US)

( * ) Notice: Subject to any disclaimer, the term of this patent is extended or adjusted under 35 U.S.C. 154(b) by 0 days.

(21) Appl. No.: 17/944,966

(22) Filed: Sep. 14, 2022

(65) Prior Publication Data

US 2023/0256141 A1    Aug. 17, 2023

Related U.S. Application Data

(63) Continuation of application No. 16/014,886, filed on Jun. 21, 2018, now Pat. No. 11,577,008.

(Continued)

(51) Int. Cl.
*A61L 29/12*      (2006.01)
*A61L 29/04*      (2006.01)
(Continued)

(52) U.S. Cl.
CPC .......... *A61L 29/126* (2013.01); *A61L 29/049* (2013.01); *A61L 29/145* (2013.01); *C08J 9/28* (2013.01);
(Continued)

(58) Field of Classification Search
CPC .. A61L 2400/18; A61L 29/049; A61L 29/126; A61L 29/145; C08J 2329/04;
(Continued)

(56) References Cited

U.S. PATENT DOCUMENTS 3,220,960 A    11/1965    Vaclavkova
3,566,874 A    3/1971    Shepherd et al.
(Continued)

FOREIGN PATENT DOCUMENTS

CN    1579601 A    2/2005
CN    102580145 A    7/2012
(Continued)

OTHER PUBLICATIONS

Hamada et al., Melting point of polyvinyl alcohol. Polym Chem. 1966;23(254):395-9.
(Continued)

*Primary Examiner* — Yan Lan
(74) *Attorney, Agent, or Firm* — Wolf, Greenfield & Sacks, P.C.

(57) ABSTRACT

High strength biomedical materials and processes for making the same are disclosed. Included in the disclosure are nanoporous hydrophilic solids that can be extruded with a high aspect ratio to make high strength medical catheters and other devices with lubricious and biocompatible surfaces. Polymers may be entrapped in pores of materials to provide a durable modification of the materials.

25 Claims, 38 Drawing Sheets

Related U.S. Application Data

(60) Provisional application No. 62/523,100, filed on Jun. 21, 2017.

(51) Int. Cl.

| | |
|---|---|
| A61L 29/14 | (2006.01) |
| C08J 9/28 | (2006.01) |
| C08K 3/16 | (2006.01) |
| C08K 3/22 | (2006.01) |
| C08K 3/32 | (2006.01) |
| C08K 3/38 | (2006.01) |
| C08K 5/053 | (2006.01) |
| C08L 29/04 | (2006.01) |
| C08L 33/10 | (2006.01) |
| C08L 33/26 | (2006.01) |
| C08L 85/02 | (2006.01) |

(52) U.S. Cl.
CPC ............ *C08K 3/16* (2013.01); *C08K 3/22* (2013.01); *C08K 3/32* (2013.01); *C08K 3/38* (2013.01); *C08K 5/053* (2013.01); *C08L 29/04* (2013.01); *C08L 33/10* (2013.01); *C08L 33/26* (2013.01); *C08L 85/02* (2013.01); *A61L 2400/18* (2013.01); *C08J 2329/04* (2013.01); *C08K 2003/321* (2013.01); *C08K 2003/387* (2013.01); *C08L 2203/02* (2013.01); *C08L 2205/22* (2013.01)

(58) Field of Classification Search
CPC .......... C08J 9/28; C08K 2003/321; C08K 2003/387; C08K 3/16; C08K 3/22; C08K 3/26; C08K 3/32; C08K 3/38; C08K 5/053; C08L 2203/02; C08L 2205/22; C08L 29/04; C08L 33/02; C08L 33/08; C08L 33/10; C08L 33/26; C08L 71/02; C08L 85/02

See application file for complete search history.

(56) References Cited

U.S. PATENT DOCUMENTS

| | | | |
|---|---|---|---|
| 3,995,623 | A | 12/1976 | Blake et al. |
| 4,024,873 | A | 5/1977 | Antoshkiw et al. |
| 4,026,296 | A | 5/1977 | Stoy et al. |
| 4,073,733 | A | 2/1978 | Yamauchi et al. |
| 4,379,874 | A | 4/1983 | Stoy |
| 4,543,102 | A | 9/1985 | Defago et al. |
| 4,663,358 | A | 5/1987 | Hyon et al. |
| 4,943,618 | A | 7/1990 | Stoy et al. |
| 5,061,254 | A | 10/1991 | Karakelle et al. |
| 5,225,120 | A | 7/1993 | Gravier et al. |
| 5,336,205 | A | 8/1994 | Zenzen et al. |
| 5,443,727 | A | 8/1995 | Gagnon |
| 5,449,382 | A | 9/1995 | Dayton |
| 5,508,036 | A | 4/1996 | Bakker et al. |
| 5,523,335 | A | 6/1996 | Whyzmuzis et al. |
| 5,578,075 | A | 11/1996 | Dayton |
| 5,601,538 | A | 2/1997 | Deem |
| 5,679,400 | A | 10/1997 | Tuch |
| 5,688,459 | A | 11/1997 | Mao et al. |
| 5,820,918 | A | 10/1998 | Ronan et al. |
| 5,928,279 | A | 7/1999 | Shannon et al. |
| 6,099,562 | A | 8/2000 | Ding et al. |
| 6,231,605 | B1 | 5/2001 | Ku |
| 6,271,278 | B1 | 8/2001 | Park et al. |
| 6,656,206 | B2 | 12/2003 | Corcoran et al. |
| 6,706,024 | B2 | 3/2004 | Modak et al. |
| 7,112,298 | B2 | 9/2006 | Kampa et al. |
| 7,329,695 | B2 | 2/2008 | Tucker et al. |
| 7,455,674 | B2 | 11/2008 | Rose |
| 7,485,670 | B2 | 2/2009 | Ruberti et al. |
| 7,619,009 | B2 | 11/2009 | Ruberti et al. |
| 7,631,760 | B2 | 12/2009 | Guelzow et al. |
| 7,745,532 | B2 | 6/2010 | Ruberti et al. |
| 7,845,670 | B2 | 12/2010 | Oberg |
| 8,017,139 | B2 | 9/2011 | Thomas et al. |
| 8,313,760 | B2 | 11/2012 | Hunter et al. |
| 8,470,035 | B2 | 6/2013 | Cruise et al. |
| 8,541,484 | B2 | 9/2013 | Choi et al. |
| 8,637,063 | B2 | 1/2014 | Kopesky et al. |
| 8,784,893 | B2 | 7/2014 | Daniloff et al. |
| 8,821,583 | B2 | 9/2014 | Myung et al. |
| 9,216,268 | B2 | 12/2015 | Liu et al. |
| 10,182,985 | B2 | 1/2019 | Bellinger et al. |
| 10,471,183 | B2 | 11/2019 | Biggins et al. |
| 10,485,898 | B2 | 11/2019 | Biggins et al. |
| 11,389,570 | B2 | 7/2022 | Biggins et al. |
| 11,577,008 | B2 | 2/2023 | Bassett et al. |
| 11,992,627 | B2 | 5/2024 | Bassett et al. |
| 2001/0002411 | A1 | 5/2001 | Ronan et al. |
| 2002/0055710 | A1 | 5/2002 | Tuch |
| 2002/0138154 | A1 | 9/2002 | Li et al. |
| 2004/0092653 | A1 | 5/2004 | Ruberti et al. |
| 2004/0247867 | A1 | 12/2004 | Chaouk et al. |
| 2006/0240059 | A1 | 10/2006 | Bavaro et al. |
| 2006/0287650 | A1 | 12/2006 | Cao et al. |
| 2007/0129690 | A1 | 6/2007 | Rosenblatt et al. |
| 2008/0065010 | A1 | 3/2008 | Bavaro et al. |
| 2008/0075628 | A1 | 3/2008 | Judd et al. |
| 2008/0160062 | A1 | 7/2008 | Richard et al. |
| 2008/0208347 | A1 | 8/2008 | Muratoglu et al. |
| 2009/0010983 | A1 | 1/2009 | Melvik et al. |
| 2009/0075267 | A1 | 3/2009 | Siena et al. |
| 2009/0076495 | A2 | 3/2009 | Dando et al. |
| 2010/0087788 | A1 | 4/2010 | Rosenblatt et al. |
| 2010/0105801 | A1 | 4/2010 | Choi |
| 2010/0106103 | A1 | 4/2010 | Ziebol et al. |
| 2010/0145286 | A1 | 6/2010 | Zhang et al. |
| 2010/0152708 | A1 | 6/2010 | Li et al. |
| 2010/0204800 | A1* | 8/2010 | Thomas .............. C08J 3/075 623/20.14 |
| 2010/0210752 | A1 | 8/2010 | Muratoglu et al. |
| 2010/0234815 | A1 | 9/2010 | Do et al. |
| 2011/0000846 | A1 | 1/2011 | Ishizuka et al. |
| 2011/0027181 | A1 | 2/2011 | Amodei et al. |
| 2011/0091515 | A1 | 4/2011 | Zilberman et al. |
| 2011/0190683 | A1 | 8/2011 | Gellman et al. |
| 2011/0244010 | A1 | 10/2011 | Doshi |
| 2013/0046346 | A1 | 2/2013 | Thorwarth et al. |
| 2013/0338431 | A1 | 12/2013 | Shalon et al. |
| 2014/0045398 | A1 | 2/2014 | Zhang et al. |
| 2014/0058251 | A1 | 2/2014 | Stigall et al. |
| 2014/0178446 | A1 | 6/2014 | Zhu et al. |
| 2014/0287179 | A1 | 9/2014 | Kamioka et al. |
| 2016/0015863 | A1 | 1/2016 | Gupta et al. |
| 2016/0136389 | A1 | 5/2016 | Christian et al. |
| 2016/0175483 | A1 | 6/2016 | Zeitels et al. |
| 2017/0143952 | A1 | 5/2017 | Siess et al. |
| 2017/0173219 | A1 | 6/2017 | Biggins et al. |
| 2017/0182223 | A1 | 6/2017 | Biggins et al. |
| 2017/0340867 | A1 | 11/2017 | Acisano, III |
| 2018/0200185 | A1* | 7/2018 | Labib .............. A61L 31/148 |
| 2018/0250116 | A1 | 9/2018 | Mourhatch et al. |
| 2018/0369454 | A1 | 12/2018 | Mannarino et al. |
| 2019/0167942 | A1 | 6/2019 | Schonfeldt |
| 2020/0093965 | A1 | 3/2020 | Biggins et al. |
| 2020/0230295 | A1 | 7/2020 | Mannarino et al. |
| 2021/0069468 | A1 | 3/2021 | Keating et al. |
| 2021/0275774 | A1 | 9/2021 | Doherty et al. |
| 2022/0088348 | A1 | 3/2022 | Bassett et al. |
| 2022/0378984 | A1 | 12/2022 | Biggins et al. |

FOREIGN PATENT DOCUMENTS

| | | |
|---|---|---|
| CN | 102634865 A | 8/2012 |
| EP | 0 532 037 A1 | 3/1993 |
| EP | 2 075 014 B1 | 7/2011 |
| JP | S52-21420 A | 2/1977 |
| JP | S55-106162 A | 8/1980 |
| JP | S58-014906 A | 1/1983 |
| JP | S61-226061 A | 10/1986 |

(56) References Cited

FOREIGN PATENT DOCUMENTS

| JP | S62-11460 A | 1/1987 |
|---|---|---|
| JP | H01-299564 A | 12/1989 |
| JP | H10-306191 A | 11/1998 |
| JP | H11-130929 A | 5/1999 |
| JP | 2002-360685 A | 12/2002 |
| JP | 2007-500764 A | 1/2007 |
| JP | 2012-251057 A | 12/2012 |
| JP | 5820918 B1 | 11/2015 |
| KR | 2018-0110695 A | 10/2018 |
| WO | WO 92/07899 A2 | 5/1992 |
| WO | WO 97/41180 A1 | 11/1997 |
| WO | WO 99/44665 A2 | 9/1999 |
| WO | WO 01/68746 A1 | 9/2001 |
| WO | WO 2007/002004 A2 | 1/2007 |
| WO | WO 2012/122023 A2 | 9/2012 |
| WO | WO 2014/063711 A1 | 5/2014 |
| WO | WO 2014/077886 A1 | 5/2014 |
| WO | WO 2017/112878 A1 | 6/2017 |
| WO | WO 2018/237166 A1 | 12/2018 |
| WO | WO 2021/168284 A1 | 8/2021 |

OTHER PUBLICATIONS

International Search Report and Written Opinion for PCT/US2018/038796 mailed Nov. 14, 2018.

[No Author Listed], Dimethyl Sulfoxide Physical Properties. Gaylord Chemical Company, L.L.C., Bulletin 101. Jun. 2014. 14 pages.

Chirilia et al., Poly(2-hydroxyethyl methacrylate) sponges as implant materials: in vivo and in vitro evaluation of cellular invasion. Biomaterials. 1993;14(1):26-38.

Fukumori et al., Significant improvement of mechanical properties for polyvinyl alcohol film prepared from freeze/thaw cycled gel. Open Journal of Organic Polymer Materials. 2013;3:110-116.

Kang, The synthesis of nanoporous hydrogels using sacrificial block copolymers. Dissertation. Massachusetts Institute of Technology. Jul. 21, 2006. 106 pages.

Peppas et al., Semicrystalline poly(vinyl alcohol) films and their blends with poly(acrylic acid) and poly(ethylene glycol) for drug delivery applications. Journal of Drug Delivery Science and Technology. 2004;14(4):291-297.

Sandeman et al., Adsorption of anionic and cationic dyes by activated carbons, PVA hydrogels, and PVA/AC composite. J Colloid Interface Sci. Jun. 15, 2011;358(2):582-92. doi: 10.1016/j.jcis.2011.02.031. Epub Feb. 17, 2011.

Speybrouck et al., Successful superior thyroid artery embolisation using microporous beads. European Society for Vascular Surgery. 2012;24:e5-e6.

U.S. Appl. No. 17/841,813, filed Jun. 16, 2022, Biggins et al.
U.S. Appl. No. 17/361,025, filed Jun. 28, 2021, Bassett et al.
U.S. Appl. No. 16/719,753, filed Dec. 18, 2019, Mannarino et al.
U.S. Appl. No. 17/193,258, filed Mar. 5, 2021, Doherty et al.
PCT/US2018/038796, Nov. 14, 2018, International Search Report and Written Opinion.
U.S. Appl. No. 18/640,689, filed Apr. 19, 2024, Bassett et al.

\* cited by examiner

HIGH STRENGTH POROUS MATERIALS INCORPORATING WATER SOLUBLE POLYMERS

RELATED APPLICATIONS

This Application is a Continuation of U.S. application Ser. No. 16/014,886, filed Jun. 21, 2018, which claims priority under 35 U.S.C. § 119 (e) to U.S. Provisional Application Ser. No. 62/523,100, filed Jun. 21, 2017, which is incorporated herein by reference in its entirety for all purposes.

TECHNICAL FIELD

The technical field generally relates to porous biomaterials, including high strength hydrophilic nanoporous biomaterials, e.g., for medical devices.

BACKGROUND

Biomaterials with high strength, low thrombogenicity, and lubricious surface properties are useful in the medical arts. The properties of materials can generally be improved with surface treatments so that the bulk material properties are preserved and the surface has properties that a preferable relative to the properties of the bulk material. However, despite such treatments, thrombus formation on medical devices may still restrict flow through and around the device, which can adversely affect infusion and aspiration, often requiring the use of expensive thrombolytic medications or even device replacement to resolve the blockage. For example, seconds after a catheter is placed into the bloodstream, blood proteins (e.g., fibrinogen and collagen) and host cells (e.g., platelets) begin to deposit on the device surface. Thrombus formation restricts flow through and around the device and can become friable and dislodge into the bloodstream, which has resulted in deep vein thrombosis and pulmonary embolism in several major clinical studies. Complications seen with such devices lengthen hospital stays and increase patient morbidity and mortality.

Accordingly, improved devices and methods are needed.

SUMMARY

Biomaterials which may be useful to make medical devices are disclosed herein. In some embodiments, materials and methods are provided herein for the fabrication of tough, lubricious biocompatible biomaterials for a variety of medical device applications. Processing techniques are disclosed to make materials with superior properties such as strength and hemocompatibility. Included herein are methods for extrusion of hydrophilic polymers to create high strength, hemocompatible, nanoporous biomaterials or other materials. The porous material may further be made to have polymers in the pores of the materials. These processes can be performed without the use of chemical crosslinkers or radiation crosslinking. Bulk incorporation of polymers into the pores of the materials is in contrast to a coating or bonding process that covers-over the pores or that relies only on bonding of a surface-treating material to a surface of the bulk material.

In one aspect, articles are provided. In some embodiments, the article comprises a polymeric material comprising a first water soluble polymer having a plurality of pores and a second water soluble polymer, same or different than the first water soluble polymer, positioned within at least a portion of the plurality of pores, wherein the article is substantially non-thrombogenic.

In some embodiments, the article comprises a polymeric material comprising a first water soluble polymer having a plurality of pores, a second water soluble polymer, same or different than the first water soluble polymer, and positioned within at least a portion of the plurality of pores, an osmotic agent present in the polymeric material, and wherein the polymeric material has a Young's elastic modulus of greater than or equal to 500 MPa in a dehydrated state and a Young's elastic modulus of less than or equal to 300 MPa and greater than or equal to 5 MPa at an equilibrium water content state.

In another aspect, dehydrated articles are provided. In some embodiments, the dehydrated article comprises a polymeric material comprising a first water soluble polymer having a plurality of pores and a second water soluble polymer, different than the first water soluble polymer, and positioned within at least a portion of the plurality of pores, wherein the polymeric material has a water content of less than 5 w/w % and greater than or equal to 0.1 w/w % in a dehydrated state, and wherein the polymeric material is configured to swell in an amount greater than or equal to 5 w/w % and less than or equal to 50 w/w % from a dehydrated state to an equilibrium water content state in less than or equal to 60 minutes at 25° C.

In some embodiments described above and herein, the plurality of pores have a mean pore size of less than or equal to 500 nm and greater than or equal to 10 nm. In some embodiments, at least 50% of the plurality of pores have a diameter of less than or equal to 1 μm. In some embodiments described above and herein, the article has a porosity of greater than or equal to 5% and less than or equal to 50% in a dehydrated state.

In some embodiments described above and herein, the article is configured to swell in an amount greater than or equal to 5 w/w % and less than or equal to 50 w/w % from a dehydrated state to an equilibrium water content state. In some embodiments described above and herein, swelling occurs in less than or equal to 60 minutes in water. In some embodiments, swelling occurs in less than or equal to 60 minutes in standard normal saline.

In some embodiments described above and herein, the article has a Young's elastic modulus of greater than or equal to 1 GPa in a dehydrated state. In some embodiments described above and herein, the article has a Young's elastic modulus of less than or equal to 100 MPa and greater than or equal to 5 MPa at an equilibrium water content state.

In some embodiments described above and herein, the article is substantially lubricious at an equilibrium water content state. In some embodiments described above and herein, the article has a surface roughness of less than or equal to 500 nm (Ra) at an equilibrium water content state. In some embodiments described above and herein, the article has a coefficient of friction of less than or equal to 0.10 at an equilibrium water content state.

In some embodiments described above and herein, the article comprises an osmotic agent present in the polymeric material in an amount greater than or equal to 0.05 w/w % and less than or equal to 2 w/w % versus the total article weight. In some embodiments described above and herein, the osmotic agent is selected from the group consisting of phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments described above and herein, the polymeric material has a water contact angle of less than or equal to 45 degrees at an equilibrium water content state.

In some embodiments described above and herein, the first water soluble polymer is present in the article in an amount of greater than or equal to 20 w/w % and less than or equal to 95 w/w % at an equilibrium water content state. In some embodiments described above and herein, the first water soluble polymer does not comprise covalent cross-linking agents. In some embodiments described above and herein, the first water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

In some embodiments described above and herein, the polymeric material comprises a mixture comprising the first water soluble polymer and a third water soluble polymer. In some embodiments described above and herein, the third water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

In some embodiments described above and herein, the second water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

In some embodiments described above and herein, the article is, or is configured for use with, a medical device such as a catheter, a balloon, a shunt, a wound drain, an infusion port, a drug delivery device, a tube, a guidewire, a contraceptive device, a feminine hygiene device, an endoscope, a graft, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device. In some embodiments described above and herein, the catheter is selected from the group consisting of central venous catheters, peripheral central catheters, midline catheters, peripheral catheters, tunneled catheters, dialysis access catheters, urinary catheters, neurological catheters, percutaneous transluminal angioplasty catheters, and peritoneal catheters.

In some embodiments described above and herein, the second water soluble polymer is positioned within the bulk of the first water soluble polymer.

In some embodiments described above and herein, less than 0.5 w/w % sorption of a therapeutic agent to the bulk of the first water-soluble polymer occurs at equilibrium water content after flushing with 5 times the volume of the article with water or normal saline.

In some embodiments described above and herein, the article comprises a first component comprising a water-soluble polymer, a second component adjacent the first component, the second component comprising a plurality of surface features configured to mechanically retain the second component within the first component, a first thermoplastic layer disposed between the first component and the second component, and a second thermoplastic layer in contact with an external surface of the first component.

In some embodiments described above and herein, the article comprises a first component comprising a water-soluble polymer, a second component adjacent the first component, the second component comprising a plurality of surface features configured to mechanically retain the second component within the first component, wherein the article has a joint strength of greater than or equal to 10 N at the interface between the first component and the second component.

In some embodiments described above and herein, the article comprises a polymeric material comprising a water-soluble polymer and a component mechanically coupled to the polymeric material, wherein the polymeric material has a water content of less than 5 w/w % and greater than or equal to 0.1 w/w % in a dehydrated state, and wherein the polymeric material is configured to swell in an amount greater than or equal to 5 w/w % and less than or equal to 50 w/w % from the dehydrated state to an equilibrium water content state in less than or equal to 60 minutes, and wherein the polymeric material is substantially non-thrombogenic.

In some embodiments described above and herein, the second component is thermally bonded to the first component. In some embodiments described above and herein, the second component has a Young's elastic modulus greater than a Young's elastic modulus of the first component.

In some embodiments described above and herein, an interface between the first component and the second component is fluidically sealed. In some embodiments described above and herein, the interface between the first component and the second component is configured to withstand an injection pressure of greater than or equal to 100 PSI.

In some embodiments described above and herein, the article comprises at least a first thermoplastic layer disposed between the first component and the second component. In some embodiments described above and herein, the second component is placed adjacent to the first component prior to sorption of a second water-soluble polymer. In some embodiments described above and herein, the second component is placed adjacent to the first component after sorption of a second water-soluble polymer and after a re-extraction of the second water-soluble polymer with a solvent.

In some embodiments described above and herein, the first component has a porosity of greater than or equal to 5%. In some embodiments described above and herein, the first component comprises a plurality of pores having a mean pore size of less than or equal to 500 nm and greater than or equal to 10 nm.

In some embodiments described above and herein, the first component is configured to swell in an amount greater than or equal to 5 w/w % and less than or equal to 50 w/w % from a dehydrated state to an equilibrium water content state. In some embodiments described above and herein, the first component has a Young's elastic modulus of greater than or equal to 1 GPa in a dehydrated state.

In some embodiments described above and herein, the first component comprises a second material positioned within the pores of the water-soluble polymer.

In some embodiments described above and herein, the first component is substantially non-thrombogenic.

In some embodiments described above and herein, the article comprises an osmotic agent present in the polymeric material in an amount greater than or equal to 0.05 w/w % versus the total article weight in the dehydrated state. In some embodiments described above and herein, the osmotic agent is selected from the group consisting of phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments described above and herein, the first component does not comprise covalent crosslinking.

In some embodiments described above and herein, the article further comprises a polyurethane dip layer between the first component and the second component.

In some embodiments described above and herein, the article comprises a first component comprising a water-soluble polymer and a plurality of pores, a second component comprising a first thermoplastic material positioned within at least a portion of the plurality of pores, and a third component comprising a second thermoplastic material associated with the second component. In some embodiments described above and herein, the third component is thermally bonded to the second component.

In some embodiments described above and herein, the first thermoplastic material at least partially swells in water at 25° C.

In some embodiments described above and herein, the third component is solvent-bonded to the first thermoplastic material.

In some embodiments described above and herein, the first thermoplastic material and/or second thermoplastic material are selected from the group consisting of: polyurethane elastomers, silicone elastomers, silicone-polyurethane copolymer, polyethylene, polypropylene, styrene isoprene butadiene copolymer, homopolymers and copolymers of vinyl acetate such as ethylene vinyl acetate copolymer, polyvinylchlorides, homopolymers and copolymers of acrylates and methacrylates, polyvinylpyrrolidone, 2-pyrrolidone, polyacrylonitrile butadiene, polycarbonates, polyamides, polyether block amide, fluoropolymers (including homopolymers and copolymers of polytetrafluoroethylene and polyvinyl fluoride), fluorinated ethylene propylene, polystyrenes, homopolymers and copolymers of styrene acrylonitrile, homopolymers and copolymers of styrene butadiene, cellulose acetate, homopolymers and copolymers of acrylonitrile butadiene styrene, polymethylpentene, polysulfones, polyesters, polyimides, polyisobutylene, polymethylstyrene, polyoxymethylene, and homopolymers and copolymers of poly(lactic acid), poly(glycolic acid), and poly(caprolactone).

In another aspect, compositions are provided. In some embodiments, the composition comprises an aqueous solution, an osmotic agent present in the solution at a concentration of greater than or equal to 0.1 M and less than or equal to 8 M, a radiopaque agent present in the solution in an amount of greater than or equal to 0 w/w % and less than or equal to 40 w/w %, and a water-soluble polymer having a molecular weight of greater than or equal to 40 kDa and less than or equal to 5000 kDa, and present in the solution in an amount greater than or equal to 10 w/w % and less than or equal to 50 w/w %.

In some embodiments described above and herein, the water-soluble polymer is present in the solution in an amount greater than or equal to 13 w/w %.

In some embodiments described above and herein, the water-soluble polymer comprises poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

In some embodiments described above and herein, the composition forms a swellable polymeric material upon extrusion.

In yet another aspect, methods are provided. In some embodiments, a method comprises: with a mixture comprising a first water soluble polymer and a salt, wherein the first water soluble polymer is present in the mixture in an amount greater than or equal to 13 w/w % versus the total weight of the mixture, performing the steps of: extruding the mixture at a temperature greater than or equal to 65° C. on a core material to form the polymeric material disposed on the core material, exposing the polymeric material to a non-solvent of the polymeric material at a temperature less than or equal to 28° C. for greater than or equal to 1 hour, introducing, to the polymeric material, a solution comprising a second water soluble polymer, different than the first water soluble polymer, and a salt, heating the polymeric material and the solution to a temperature of greater than or equal to 30° C., flowing the solution adjacent the polymeric material for greater than or equal to 3 hours, and drying the polymeric material, wherein the second water soluble polymer is positioned in at least one pore of the first water soluble polymer.

In some embodiments described above and herein, the non-solvent comprises alcohol. In some embodiments, the non-solvent is ethanol.

In some embodiments described above and herein, exposing the polymeric material to the non-solvent of the polymeric material is for greater than or equal to 10 hours.

In some embodiments described above and herein, the method comprises annealing the polymeric material to a temperature of greater than or equal to 100° C. for greater than or equal to 60 minutes.

In some embodiments described above and herein, the core material may be air, water, a non-solvent liquid, a solid, or a gas.

In some embodiments described above and herein, the method comprises: with a mixture comprising at least one water soluble polymer, a salt, and water, wherein the at least one water soluble polymer is present in the mixture in an amount greater than or equal to 13 w/w % versus the total weight of the mixture, performing the steps of: heating the mixture to a temperature greater than or equal to 65° C., after heating the mixture, cooling the mixture to a temperature at least 20° C. cooler than a melting point of the mixture and mechanically shaping the mixture, after cooling the mixture, extruding the mixture at a temperature greater than or equal to 65° C. on a core material to form the polymeric material disposed on the core material, exposing the polymeric material to non-solvent of the polymeric material at a temperature less than or equal to room temperature for greater than or equal to 4 hours, and removing at least a portion of the core material from the polymeric material.

In some embodiments described above and herein, the method comprises mixing the mixture at an agitation speed of greater than or equal to 200 RPM.

In some embodiments described above and herein, the method comprises mixing the mixture at an agitation speed of greater than or equal to 1000 RPM and at a temperature greater than or equal to 80° C.

In some embodiments described above and herein, the method comprises annealing the polymeric material at a temperature of greater than or equal to 100° C. for greater than or equal to 1.0 hours.

In some embodiments described above and herein, the method comprises sorption of a second water-soluble polymer into the polymeric material.

In some embodiments described above and herein, the second water soluble polymer is PAA.

In some embodiments described above and herein, the method comprises mechanical agitation of the mixture.

In some embodiments described above and herein, the non-solvent comprises alcohol. In some embodiments, the non-solvent is ethanol.

In some embodiments described above and herein, the method comprises administering, into an external orifice of a subject, a polymeric material comprising a water-soluble polymer and having an aspect ratio of greater than or equal to 3:1, wherein administration of the article does not comprise the use of a sheath introducer, wherein the polymeric material is substantially non-thrombogenic, and wherein the polymeric material has a water content of less than 5 w/w % and greater than or equal to 0.1 w/w % in the dehydrated state, and wherein the polymeric material is configured to swell in an amount greater than or equal to 5 w/w % and less than or equal to 50 w/w % from a dehydrated state to an equilibrium water content state in less than or equal to 60 minutes.

In some embodiments, the method comprises providing a mixture comprising at least one water soluble polymer, a salt, and water, wherein the at least one water soluble polymer is present in the mixture in an amount greater than or equal to 13 w/w % versus the total weight of the mixture, extruding the mixture at a temperature greater than or equal to 65° C. on a core material to form the polymeric material disposed on the core tubing, exposing the polymeric material to ethanol at a temperature less than or equal to room temperature, exposing the polymeric material to a humectant, and dehydrating the polymeric material, wherein the dehydrated polymeric material has a water content of less than 5 w/w % and greater than or equal to 0.1 w/w % in the dehydrated state.

Another embodiment is a process for making a hydrophilic material comprising heating a mixture that comprises at least one water soluble polymer and a solvent to a temperature above a melting point of the polymer, forming the mixture, and passing the mixture into a solvent-removing environment. Extrusion may be used to form the mixture, with the mixture being formed into a continuous porous solid as it passes through a die. A nanoporous solid may be made that has a Young's modulus of at least 5 MPa at equilibrium water content (EWC) of the porous solid. Extrusion may be used to form high strength materials with a high aspect ratio, including tubulars useful as catheters.

Another embodiment is a polymeric material comprising a hydrophilic porous solid, with the porous solid having a solids content of at least 33% w/w and a Young's modulus of at least 5 MPa, at equilibrium water content (EWC). The material may be formed with a high aspect ratio, for example, more than 10:1, including materials formed as catheters.

Another embodiment is a process comprising solvating, in a mixture, a pre-desolvated hydrophilic structural matrix that comprises one or more hydrophilic polymers physically crosslinked form a porous matrix, with the mixture having one or more water soluble polymers that resolvates the porous hydrophilic porous matrix. The matrix may further be annealed.

Another embodiment is a material comprising a porous matrix of physically crosslinked hydrophilic polymers that are crosslinked to form the matrix and to define pores of the matrix, with the matrix comprising a water-soluble polymer incorporated into the surface without covalent crosslinking to the surface. The water-soluble polymer may be, for instance, incorporated as a monolayer or present in pores of the matrix at the surface and under the surface.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 22A-22C are photographs of a sixth experimental result of the thrombogenicity test of Example 14 showing control (22A), a porous solid without (22B) or with (22C) a bulk incorporated water-soluble polymer.

DETAILED DESCRIPTION

High strength porous materials incorporating water soluble polymers, are generally provided. For example, materials, methods, and uses are set forth herein for a biomaterial comprising a medically acceptable porous solid. The disclosed compositions and articles may be useful for administration to a subject (e.g., a patient). Advantageously, the compositions and/or articles described herein may be substantially non-thrombogenic, lubricious, and/or biocompatible. In some embodiments, the compositions and/or articles described herein may be suitable for administration to a subject for a relatively long period of time, e.g., without the formation of a thrombus, without fouling, and/or without absorbing (or adsorbing) one or more substances (e.g., therapeutic agents, proteins, blood, plasma) internal to the subject. Methods for forming such compositions and/or articles are also provided.

In some embodiments, the compositions and articles (e.g., article 10 of FIG. 1A, article 12 of FIG. 1B) described herein comprise a polymeric material comprising a first water soluble polymer having a plurality of pores and a second water soluble polymer, same or different than the first water soluble polymer, positioned within at least a portion of the plurality of pores. Without wishing to be bound by theory, in some embodiments, the presence of a second water soluble polymer positioned within at least a portion of the plurality of the pores of the first water soluble may decrease the thrombogenicity and/or increase the lubriciousness of the article (e.g., article 10 of FIG. 1A, article 12 of FIG. 1B) as compared to articles (e.g., article 10 of FIG. 1A, article 12 of FIG. 1B) without the second water soluble polymer positioned within the pores (all other factors being equal). In an exemplary set of embodiments, the first water soluble polymer is polyvinyl alcohol. In another exemplary set of embodiments, the second water soluble polymer is polyacrylic acid. Other water soluble polymers are also possible, as described herein.

In some embodiments, the articles (e.g., article 10 of FIG. 1A, article 12 of FIG. 1B) and compositions described herein are administered to a subject. In some embodiments, the article may be administered orally, rectally, vaginally, nasally, intravenously, subcutaneously, or uretherally. In some cases, the article may be administered into a cavity, epidural space, and/or abscess of a subject.

Figure 1A:
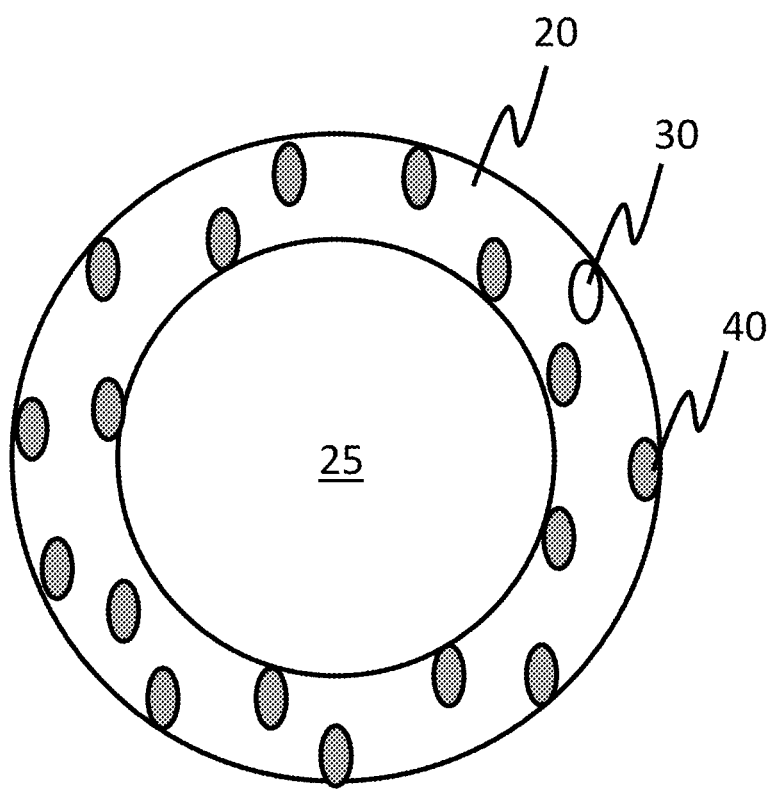
FIG. 1A is a cross-sectional schematic diagram of an exemplary article comprising a plurality of pores, according to one set of embodiments.

As described herein, in some embodiments, the compositions and articles described herein comprise a polymeric material comprising a first water soluble polymer having a plurality of pores. For example, as illustrated in FIG. 1A article 10 comprises polymeric material comprising a first water soluble polymer 20 and having a plurality of pores 30. In some embodiments, second water soluble polymer 40 is positioned within at least a portion (e.g., at least 10%, at least 20%, at least 30%, at least 40%, at least 50%, at least 60%, at least 70%, at least 80%, at least 90%, at least 95%, at least 98%, at least 99%, at least 99.99%) of the plurality of pores. In some embodiments, second water soluble polymer 40 is positioned within less than or equal to 100%, less than or equal to 90%, less than or equal to 80%, less than or equal to 70%, less than or equal to 60%, less than or equal to 50%, less than or equal to 40%, less than or equal to 30%, less than or equal to 20%, or less than or equal to 10% of the plurality of pores 30. Combinations of the above-referenced ranges are also possible.

Figure 1B:
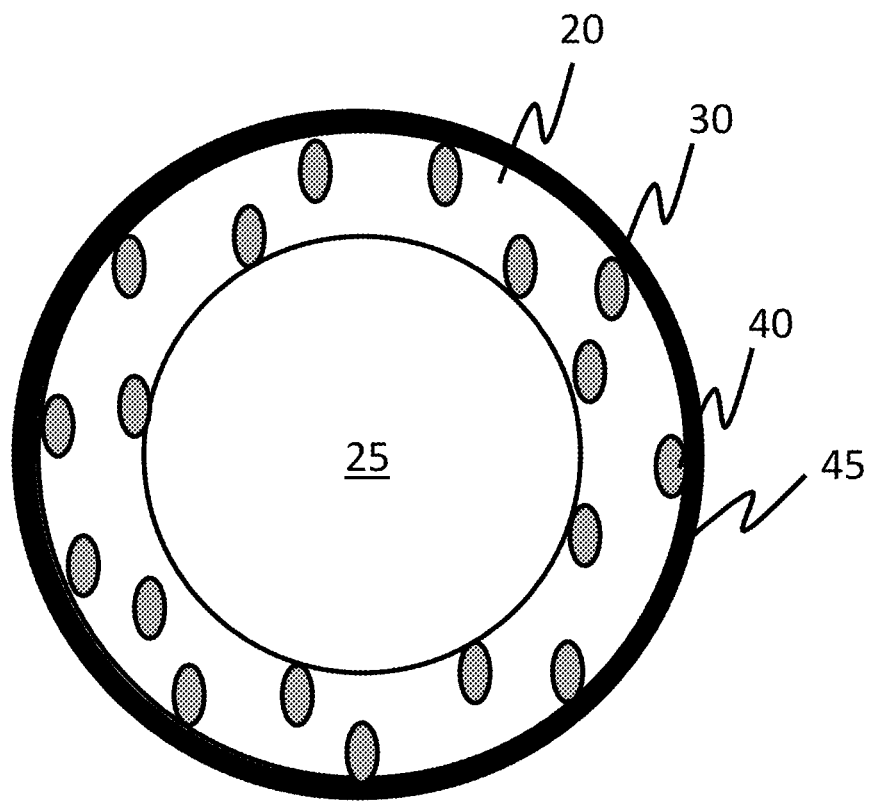
FIG. 1B is a cross-sectional schematic diagram of an exemplary article comprising a plurality of pores, according to one set of embodiments.

In some embodiments, the second water soluble polymer is positioned within the bulk of the first water soluble polymer (e.g., within the pores and/or interstices of the first water soluble polymer). In some embodiments, as illustrated in FIG. 1B, the second water soluble polymer 40 may be present as a coating 45 on at least a portion of a surface of polymeric material 20. Although FIG. 1B shows the second water soluble polymer as a coating on the first water soluble polymer and in the pores of the first water soluble polymer, it should be appreciated that in some embodiments, only a coating 45 is present and the pores 30 are not substantially filled with the second water soluble polymer 40. Other configurations are also possible.

In some embodiments, article 10 and/or article 12 may be hollow (e.g., comprising a hollow core 25). However, while FIGS. 1A and 1B are depicted having a hollow core, those of ordinary skill in the art would understand based upon the teachings of this specification that such a hollow core may not be present. That is to say, in some cases, the core 25 of the article (e.g., article 10 of FIG. 1A, article 12 of FIG. 1B) may be a bulk material without a hollow core 25.

In some embodiments, the plurality of pores (e.g., of an article (e.g., article 10 of FIG. 1A, article 12 of FIG. 1B) or of a first water soluble material, optionally having a second water soluble polymer positioned within at least a portion of said pores) have a particular mean pore size. In some embodiments, the mean pore size of the plurality of pores is less than or equal to 500 nm, less than or equal to 450 nm, less than or equal to 400 nm, less than or equal to 350 nm, less than or equal to 300 nm, less than or equal to 250 nm, less than or equal to 200 nm, less than or equal to 150 nm, less than or equal to 100 nm, less than or equal to 75 nm, less than or equal to 50 nm, less than or equal to 25 nm, less than or equal to 20 nm, or less than or equal to 15 nm. In some embodiments, the plurality of pores have a mean pore size of greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, or greater than or equal to 450 nm. Combinations of the above referenced ranges are also possible (e.g., less than or equal to 500 nm and greater than or equal to 10 nm). Other ranges are also possible. Mean pore size, as described herein, may be determined by mercury intrusion porosimetry of the material in a dehydrated state (i.e. having less than 5 w/w % water).

In some embodiments, at least a portion of the plurality of pores may be characterized as nanopores, e.g., pores having an average cross-sectional dimension of less than 1 micron. In some embodiments, at least a portion of the plurality of pores may be characterized as micropores, e.g., pores having an average cross-sectional dimension of less than 1 mm and greater than or equal to 1 micron. In some embodiments, at least 50% (e.g., at least 60%, at least 70%, at least 80%, at least 90%, at least 95%, at least 98%, at least 99%, at least 99.9%) of the plurality of pores have a diameter that is less than 1 micron, less than or equal to 800 nm, less than or equal to 600 nm, less than or equal to 500 nm, less than or equal to 450 nm, less than or equal to 400 nm, less than or equal to 350 nm, less than or equal to 300 nm, less than or equal to 250 nm, less than or equal to 200 nm, less than or equal to 150 nm, less than or equal to 100 nm, less than or equal to 75 nm, less than or equal to 50 nm, less than or equal to 25 nm, less than or equal to 20 nm, or less than or equal to 15 nm. In some cases, at least 50% of the plurality of pores have a diameter than is greater than or equal to 10 nm, greater than or equal to 15 nm, greater than or equal to 20 nm, greater than or equal to 25 nm, greater than or equal to 50 nm, greater than or equal to 75 nm, greater than or equal to 100 nm, greater than or equal to 150 nm, greater than or equal to 200 nm, greater than or equal to 250 nm, greater than or equal to 300 nm, greater than or equal to 350 nm, greater than or equal to 400 nm, greater than or equal to 450 nm, greater than or equal to 500 nm, greater than or equal to 600 nm, or greater than or equal to 800 nm. Combinations of the above referenced ranges are also possible (e.g., less than or equal to 1000 nm and greater than or equal to 10 nm). Other ranges are also possible.

The compositions and article (e.g., article 10 of FIG. 1A, article 12 of FIG. 1B) described herein may have a particular porosity e.g., in a dehydrated state. In some embodiments, the article (or polymeric material) has a porosity of greater than or equal to 5%, greater than or equal to 10%, greater than or equal to 15%, greater than or equal to 20%, greater than or equal to 25%, greater than or equal to 30%, greater than or equal to 35%, greater than or equal to 40%, or greater than or equal to 45% in a dehydrated state. In some embodiments, the article (or polymeric material) has a porosity of less than or equal to 50%, less than or equal to 45%, less than or equal to 40%, less than or equal to 35%, less than or equal to 30%, less than or equal to 25%, less than or equal to 20%, less than or equal to 15%, or less than or equal to 10% in a dehydrated state. Combinations of the above-referenced ranges are also possible (e.g., greater than or equal to 5% and less than or equal to 50% in a dehydrated state). Other ranges are also possible.

As described herein, in some embodiments, the article (or polymeric material) is substantially non-thrombogenic. Nonthrombogenicity may be determined as described in Example 13.

In some embodiments, the article (e.g., article 10 of FIG. 1A, article 12 of FIG. 1B) (or polymeric material (e.g., polymeric material 20 of FIGS. 1A-1B)) is hydrophilic. The term "hydrophilic" as used herein is given its ordinary meaning in the art and refers to a material surface having a water contact angle as determined by goniometry of less than 90 degrees. In some embodiments, a surface of the polymeric material of the article has a water contact angle of less than or equal to 45 degrees, less than or equal to 40 degrees, less than or equal to 35 degrees, less than or equal to 30 degrees, less than or equal to 25 degrees, less than or equal to 20 degrees, less than or equal to 15 degrees, less than or equal to 10 degrees, less than or equal to 5 degrees, or less than or equal to 2 degrees at an equilibrium water content state. In some embodiments, the surface of the polymeric material has a water contact angle of greater than or equal to 1 degree, greater than or equal to 2 degrees, greater than or equal to 5 degrees, greater than or equal to 10 degrees, greater than or equal to 15 degrees, greater than or equal to 20 degrees, greater than or equal to 25 degrees, greater than or equal to 30 degrees, greater than or equal to 35 degrees, or greater than or equal to 40 degrees at an equilibrium water content state. Combinations of the above-referenced ranges are also possible (e.g., greater than or equal to 1 degree and less than or equal to 45 degrees). Other ranges are also possible.

Equilibrium water content state, as used herein, refers the steady state of an article (or material) which does not gain (e.g., absorb) or lose bulk water content as determined when submerged in water at 25° C. without externally applied mechanical stresses. Those skilled in the art would understand that steady state (or equilibrium water content state) shall be understood to not require absolute conformance to a strict thermodynamic definition of such term, but, rather, shall be understood to indicate conformance to the thermodynamic definition of such term to the extent possible for the subject matter so characterized as would be understood by one skilled in the art most closely related to such subject matter (e.g., accounting for factors such as passive diffusion and/or Brownian motion).

In some embodiments, the article (e.g., article 10 of FIG. 1A, article 12 of FIG. 1B) is substantially lubricious at an equilibrium water content state. For example, in some embodiments, the article (or polymeric material of the article) has a surface roughness of less than or equal to 1000 nm (Ra) at an equilibrium water content state. In some embodiments, the article (or polymeric material of the article) has a surface roughness (Ra) of less than or equal to 500 nm, less than or equal to 400 nm, less than or equal to 300 nm, less than or equal to 250 nm, less than or equal to 200 nm, less than or equal to 150 nm, less than or equal to 100 nm, less than or equal to 50 nm, less than or equal to 25 nm, less than or equal to 10 nm, or less than or equal to 5 nm at an equilibrium water content state. In some embodiments, the article (or polymeric material of the article) has a surface roughness (Ra) of greater than or equal to 5 nm at an equilibrium water content state, greater than or equal to 10 nm, greater than or equal to 25 nm, greater than or equal to 50 nm, greater than or equal to 100 nm, greater than or equal to 150 nm, greater than or equal to 200 nm, greater than or equal to 250 nm, greater than or equal to 300 nm, greater than or equal to 400 nm, or greater than or equal to 500 nm at an equilibrium water content state. Combinations of the above-referenced ranges are also possible (e.g., greater than or equal to 5 nm and less than or equal to 1000 nm). Other ranges are also possible.

In some embodiments, the article (e.g., article 10 of FIG. 1A, article 12 of FIG. 1B) has a surface having a coefficient of friction of less than or equal to 0.10 at an equilibrium water content state. For example, the coefficient of friction of a surface of the article (or polymeric material of the article) is less than or equal to 0.1, less than or equal to 0.09, less than or equal to 0.08, less than or equal to 0.07, less than or equal to 0.06, less than or equal to 0.05, less than or equal to 0.04, less than or equal to 0.03, or less than or equal to 0.02. In some embodiments, the coefficient of friction of the surface of the article (or polymeric material of the article) is greater than or equal to 0.01, greater than or equal to 0.02, greater than or equal to 0.03, greater than or equal to 0.04, greater than or equal to 0.05, greater than or equal to 0.06, greater than or equal to 0.07, greater than or equal to 0.08, or greater than or equal to 0.09. Combinations of the above-referenced ranges are also possible (e.g., less than or equal to 0.1 and greater than or equal to 0.01). Other ranges are also possible.

Advantageously, the compositions and articles described herein may have low sorption of substances such as therapeutic agents (and/or e.g., proteins) in the presence of a dynamic fluid comprising such substances. Such articles and compositions may be useful for use in subjects where, for example, the presence of the article should not substantially decrease the availability and/or concentration of therapeutic agents delivered to the subject (e.g., via the article). In some embodiments, administration of therapeutic agents via a fluid flowed within the articles described herein do not substantially reduce the concentration of the therapeutic agent within the fluid. In some cases, the article may not absorb and/or adsorb the therapeutic agent, e.g., during flow or use.

In some embodiments, less than or equal to 0.5 w/w % sorption of a therapeutic agent to the surface and/or bulk of the first water-soluble polymer occurs as determined at equilibrium water content after exposing the polymer to the therapeutic agent and flushing with 5 times the volume of the article with an aqueous solution, such as water or normal saline. In some embodiments, less than or equal to 0.5 w/w %, less than or equal to 0.4 w/w %, less than or equal to 0.3 w/w %, less than or equal to 0.2 w/w %, or less than or equal to 0.1 w/w % sorption of the therapeutic agent to the surface and/or bulk of the first water-soluble polymer occurs. In some embodiments, greater than or equal to 0.05 w/w %, greater than or equal to 0.1 w/w %, greater than or equal to 0.2 w/w %, greater than or equal to 0.3 w/w %, or greater than or equal to 0.4 w/w % sorption of the therapeutic agent to the surface and/or bulk of the first water-soluble polymer occurs. Combinations of the above-referenced ranges are also possible (e.g., less than or equal to 0.5 w/w % and greater than or equal to 0.05 w/w %). Other ranges are also possible.

Advantageously, the articles and compositions described herein may have desirable swelling characteristics (e.g., in water, in saline, in a fluidic environment of a subject).

In some embodiments, the articles (e.g., article 10 of FIG. 1A, article 12 of FIG. 1B) described herein are in a dehydrated state. For example, in some embodiments, the articles (or polymeric materials) described herein have a water content of less than or equal to 5 w/w %, less than or equal to 4 w/w %, less than or equal to 3 w/w %, less than or equal to 2 w/w %, less than or equal to 1 w/w %, less than or equal to 0.8 w/w %, less than or equal to 0.6 w/w %, less than or equal to 0.4 w/w %, or less than or equal to 0.2 w/w % in the dehydrated state. In some embodiments, the articles (or polymeric materials) described herein have a water content of greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 2 w/w %, greater than or equal to 3 w/w %, or greater than or equal to 4 w/w %. Combinations of the above-referenced ranges are also possible (e.g., less than 5 w/w % and greater than or equal to 0.1 w/w %). Other ranges are also possible. The dehydrated state, as described herein, generally refers to the steady state determined under ambient conditions in which the article (or polymeric material) has no appreciable decrease in water content of less than 5 w/w % over 24 hours. In some embodiments, the articles described herein may comprise a coating or unbound porogen, such as a humectant coating, as described in more detail below.

Advantageously, the articles and compositions described herein may be configured for rapid swelling in the presence of an aqueous solution, such as water and/or saline. In some embodiments, the article (e.g., article 10 of FIG. 1A, article 12 of FIG. 1B) (or polymeric material (e.g., polymeric material 20 of FIGS. 1A-1B)) is configured to swell in an amount greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w % from a dehydrated state to an equilibrium water content state at 25° C., e.g., in a particular amount of time (e.g., less than or equal to 60 minutes), as described in more detail below. In some embodiments, the article (or polymeric material) is configured to swell in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, or less than or equal to 10 w/w % from a dehydrated state to an equilibrium water content state at 25° C., e.g., in a particular amount of time (e.g., less than or equal to 60 minutes) as described in more detail below. Combinations of the above-referenced ranges are also possible (e.g., greater than or equal to 5 w/w % and less than or equal to 50 w/w %). Other ranges are also possible.

In some embodiments, the article (e.g., article 10 of FIG. 1A, article 12 of FIG. 1B) (or polymeric material (e.g., polymeric material 20 of FIGS. 1A-1B)) is configured to swell in an amount greater than or equal to 5 w/w % from a dehydrated state to an equilibrium water content state in less than or equal to 60 minutes, less than or equal to 50 minutes, less than or equal to 40 minutes, less than or equal to 30 minutes, less than or equal to 20 minutes, less than or equal to 10 minutes, less than or equal to 5 minutes, or less than or equal to 2 minutes at 25° C. In some embodiments, the article (or polymeric material) is configured to swell in an amount greater than or equal to 5 w/w % from a dehydrated state to an equilibrium water content state in greater than or equal to 1 minute, greater than or equal to 2 minutes, greater than or equal to 5 minutes, greater than or equal to 10 minutes, greater than or equal to 20 minutes, greater than or equal to 30 minutes, greater than or equal to 40 minutes, or greater than or equal to 50 minutes at 25° C. Combinations of the above-referenced ranges are also possible (e.g., less than or equal to 60 minutes and greater than or equal to 1 minute). Other ranges are also possible.

In an exemplary embodiment, article (e.g., article 10 of FIG. 1A, article 12 of FIG. 1B) (or polymeric material (e.g., polymeric material 20 of FIGS. 1A-1B)) is configured to swell to an equilibrium water content state (e.g., greater than or equal to 5 w/w %) in less than or equal to 60 minutes from a dehydrated state (e.g., less than 5 w/w %) in water. In some embodiments, the article (or polymeric material) is configured to swell to an equilibrium water content (e.g., greater than or equal to 5 w/w %) in less than or equal to 60 minutes from a dehydrated state (e.g., less than 5 w/w %) in standard normal saline. In another exemplary embodiment, the article (or polymeric material) is configured to swell to an equilibrium water content (e.g., greater than or equal to 5 w/w %) in less than or equal to 60 minutes from a dehydrated state (e.g., less than 5 w/w %) in normal saline.

In some embodiments, the article (e.g., article 10 of FIG. 1A, article 12 of FIG. 1B) (or polymeric material (e.g., polymeric material 20 of FIGS. 1A-1B)) has a particular length in the dehydrated state. In some embodiments, the article (or polymeric material) has an increase in overall length in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to its length in the dehydrated state. In some cases, the article (or polymeric material) has an increase in overall length in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to its length in the dehydrated state. Combinations of the above-referenced ranges are also possible (e.g., greater than or equal to 0.1% and less than or equal to 20%). Other ranges are also possible.

In some embodiments, the article (e.g., article 10 of FIG. 1A, article 12 of FIG. 1B) (or polymeric material (e.g., polymeric material 20 of FIGS. 1A-1B)) has a particular outer maximum cross-sectional dimension, such as an outer diameter, in the dehydrated state. In some embodiments, the article (or polymeric material) has an increase in an outer maximum cross-sectional dimension (e.g., outer diameter) in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to the maximum cross-sectional dimension (e.g., outer diameter) in the dehydrated state. In some cases, the article (or polymeric material) has an increase in the maximum cross-sectional dimension (e.g., outer diameter) in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to the maximum cross-sectional dimension (e.g., outer diameter) in the dehydrated state. Combinations of the above-referenced ranges are also possible (e.g., greater than or equal to 0.1% and less than or equal to 20%, greater than or equal to 0.1% and less than or equal to 10%). Other ranges are also possible.

In some embodiments, the article (or polymeric material) has a particular inner diameter in the dehydrated state (e.g., in an embodiment in which the article comprises a hollow core). In some embodiments, the article (or polymeric material) has an increase in the inner diameter in the equilibrium water content state of greater than or equal to 0.1%, greater than or equal to 0.5%, greater than or equal to 1%, greater than or equal to 2%, greater than or equal to 4%, greater than or equal to 6%, greater than or equal to 8%, greater than or equal to 10%, greater than or equal to 12%, greater than or equal to 14%, greater than or equal to 16%, or greater than or equal to 18% as compared to the inner diameter in the dehydrated state. In some cases, the article (or polymeric material) has an increase in the inner diameter in the equilibrium water content state of less than or equal to 20%, less than or equal to 18%, less than or equal to 16%, less than or equal to 14%, less than or equal to 12%, less than or equal to 10%, less than or equal to 8%, less than or equal to 6%, less than or equal to 4%, less than or equal to 2%, less than or equal to 1%, or less than or equal to 0.5% as compared to the inner diameter in the dehydrated state. Combinations of the above-referenced ranges are also possible (e.g., greater than or equal to 0.1% and less than or equal to 20%). Other ranges are also possible.

In some embodiments, the article (e.g., article 10 of FIG. 1A, article 12 of FIG. 1B) comprises a polymeric material having desirable mechanical properties. For example, in some embodiments, the polymeric material has a Young's elastic modulus in the dehydrated state (e.g., less than 5 w/w % water content) of greater than or equal to 500 MPa, greater than or equal to 600 MPa, greater than or equal to 750 MPa, greater than or equal to 800 MPa, greater than or equal to 900 MPa, greater than or equal to 1000 MPa, greater than or equal to 1250 MPa, greater than or equal to 1500 MPa, greater than or equal to 1750 MPa, greater than or equal to 2000 MPa, greater than or equal to 2500 MPa, greater than or equal to 3000 MPa, greater than or equal to 3500 MPa, or greater than or equal to 4000 MPa. In some embodiments, the polymeric material has a Young's elastic modulus in the dehydrated state (e.g., less than 5 w/w % water content) of less than or equal to 5000 MPa, less than or equal to 4000 MPa, less than or equal to 3500 MPa, less than or equal to 3000 MPa, less than or equal to 2500 MPa, less than or equal to 2000 MPa, less than or equal to 1750 MPa, less than or equal to 1500 MPa, less than or equal to 1250 MPa, less than or equal to 1000 MPa, less than or equal to 900 MPa, less than or equal to 800 MPa, less than or equal to 750 MPa, or less than or equal to 600 MPa. Combinations of the above-referenced ranges are also possible (e.g., greater than or equal to 500 MPa and less than or equal to 5000 MPa). Other ranges are also possible.

In some embodiments, the polymeric material has a Young's elastic modulus at an equilibrium water content state of less than or equal to 300 MPa, less than or equal to 250 MPa, less than or equal to 200 MPa, less than or equal to 150 MPa, less than or equal to 100 MPa, less than or equal to 75 MPa, less than or equal to 50 MPa, less than or equal to 25 MPa, less than or equal to 20 MPa, or less than or equal to 10 MPa. In some embodiments, the polymeric material has a Young's elastic modulus at an equilibrium water content state of greater than or equal to 5 MPa, greater than or equal to 10 MPa, greater than or equal to 20 MPa, greater than or equal to 25 MPa, greater than or equal to 50 MPa, greater than or equal to 75 MPa, greater than or equal to 100 MPa, greater than or equal to 150 MPa, greater than or equal to 200 MPa, or greater than or equal to 250 MPa. Combinations of the above-referenced ranges are also possible (e.g., less than or equal to 300 MPa and greater than or equal to 5 MPa). Other ranges are also possible.

In some embodiments, the article (e.g., article 10 of FIG. 1A, article 12 of FIG. 1B) comprises an osmotic agent. For example, in some embodiments, an osmotic agent may be added (e.g., to the pre-polymer) during formation of the article. In some embodiments, the osmotic agent is present in the polymeric material (e.g., after formation of the polymeric material) in an amount greater than or equal to 0.05 w/w %, greater than or equal to 0.1 w/w %, greater than or equal to 0.2 w/w %, greater than or equal to 0.4 w/w %, greater than or equal to 0.6 w/w %, greater than or equal to 0.8 w/w %, greater than or equal to 1 w/w %, greater than or equal to 1.2 w/w %, greater than or equal to 1.4 w/w %, greater than or equal to 1.6 w/w %, or greater than or equal to 1.8 w/w %. In some cases, the osmotic agent may be present in the polymeric material (e.g., after formation of the polymeric material) in an amount of less than or equal to 2 w/w %, less than or equal to 1.8 w/w %, less than or equal to 1.6 w/w %, less than or equal to 1.4 w/w %, less than or equal to 1.2 w/w %, less than or equal to 1 w/w %, less than or equal to 0.8 w/w %, less than or equal to 0.6 w/w %, less than or equal to 0.4 w/w %, less than or equal to 0.2 w/w %, or less than or equal to 0.01 w/w %. Combinations of the above-referenced ranges are also possible (e.g., greater than or equal to 0.05 w/w % and less than or equal to 2 w/w %). Other ranges are also possible.

Non-limiting examples of suitable osmotic agents include phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

In some embodiments, the composition (e.g., comprising a polymeric material) does not comprise covalent crosslinking, as described in more detail below. In other embodiments, however, the composition comprises physical crosslinking (e.g., interpenetrating network, chain entanglement, and/or one or more bonds such as covalent, ionic, and/or hydrogen bonding). In a particular set of embodiments, no covalent crosslinking agents are used to form the polymeric material, the first water soluble polymer of the polymeric material, and/or the second water soluble polymer.

The first water soluble polymer may be present in the article (e.g., article 10 of FIG. 1A, article 12 of FIG. 1B) in any suitable amount. For example, in some embodiments, the first water soluble polymer is present in the article in an amount of greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, or greater than or equal to 90 w/w % at an equilibrium water content state. In some embodiments, the first water soluble polymer is present in the article in an amount of less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, or less than or equal to 25 w/w % at an equilibrium water content state. Combinations of the above-referenced ranges are also possible (e.g., greater than or equal to 20 w/w % and less than or equal to 95 w/w %). Other ranges are also possible.

In some embodiments, the first water soluble polymer comprises or is selected from the group consisting of poly (vinyl alcohol), poly(acrylic acid), polyethylene glycol, poly (vinyl pyrrolidone), poly(methacrylic sulfobetaine), poly (acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly (2-hydroxymethylmethacrylate), and combinations thereof. In an exemplary set of embodiments, the first water soluble polymer is poly(vinyl alcohol).

In some embodiments, the polymeric material comprises a mixture comprising the first water-soluble polymer and another (e.g., a third) water soluble polymer. In some embodiments, the third water soluble polymer comprises or is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof. The first and other (e.g., third) water soluble polymers may have different chemical compositions.

In some embodiments, the total weight of the first water soluble polymer and another (e.g., a third) water soluble polymer in the article is greater than or equal to 20 w/w %, greater than or equal to 25 w/w %, greater than or equal to 30 w/w %, greater than or equal to 35 w/w %, greater than or equal to 40 w/w %, greater than or equal to 45 w/w %, greater than or equal to 50 w/w %, greater than or equal to 55 w/w %, greater than or equal to 60 w/w %, greater than or equal to 65 w/w %, greater than or equal to 70 w/w %, greater than or equal to 75 w/w %, greater than or equal to 80 w/w %, greater than or equal to 85 w/w %, greater than or equal to 90 w/w %, greater than or equal to 95 w/w %, greater than or equal to 98 w/w %, or greater than or equal to 99 w/w % at an equilibrium water content state. In some embodiments, the total weight of the first water soluble polymer and another (e.g., a third) water soluble polymer in the article in an amount of less than or equal to 100 w/w %, less than or equal to 90 w/w %, less than or equal to 98 w/w %, less than or equal to 95 w/w %, less than or equal to 90 w/w %, less than or equal to 85 w/w %, less than or equal to 80 w/w %, less than or equal to 75 w/w %, less than or equal to 70 w/w %, less than or equal to 65 w/w %, less than or equal to 60 w/w %, less than or equal to 55 w/w %, less than or equal to 50 w/w %, less than or equal to 45 w/w %, less than or equal to 40 w/w %, less than or equal to 35 w/w %, less than or equal to 30 w/w %, or less than or equal to 25 w/w % at an equilibrium water content state. Combinations of the above-referenced ranges are also possible (e.g., greater than or equal to 20 w/w % and less than or equal to 100 w/w %). Other ranges are also possible.

In some embodiments, the ratio of the first water soluble polymer to the third water soluble polymer present in the article is less than or equal to 100:0, less than or equal to 99:1, less than or equal to 95:5, less than or equal to 90:10, less than or equal to 80:20, less than or equal to 70:30, less than or equal to 60:40, or less than or equal to 55:45. In some embodiments, the ratio of the first water soluble polymer to the third water soluble polymer present in the article is greater than or equal to 50:50, greater than or equal to 60:40, greater than or equal to 70:30, greater than or equal to 80:20, greater than or equal to 90:10, greater than or equal to 95:5, or greater than or equal to 99:1. Combinations of the above-referenced ranges are also possible (e.g., less than or equal to 100:0 and greater than or equal to 50:50). Other ranges are also possible.

As described above and herein, in some embodiments, the article (e.g., article 10 of FIG. 1A, article 12 of FIG. 1B) comprises a second water soluble polymer (e.g., second water soluble polymer 40) disposed within at least a portion of the plurality of pores (e.g., plurality of pores 30) of the polymeric material (e.g., polymeric material 20). In some embodiments, the second water soluble polymer comprises or is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof. In some embodiments, the second water soluble polymer is poly(acrylic acid). The second water soluble polymer may have a different chemical composition from that of the first (e.g., and optionally third) water soluble polymers.

The second water soluble polymer (e.g., second water soluble polymer 40) may be present in the article in any suitable amount. For example, in some embodiments, the second water soluble polymer is present in the article in an amount of greater than or equal to 0.05 w/w %, greater than or equal to 0.1 w/w %, greater or than or equal to 0.2 w/w %, greater than or equal to 0.5 w/w %, greater than or equal to 1.0 w/w %, greater than or equal to 2.0 w/w %, greater than or equal to 3.0 w/w %, greater than or equal to 4.0 w/w %, greater than or equal to 5.0 w/w %, greater than or equal to 10 w/w %, greater than or equal to 20 w/w %, greater than or equal to 30 w/w %, greater than or equal to 40 w/w %, greater than or equal to 50 w/w %, greater than or equal to 60 w/w %, greater than or equal to 70 w/w %, greater than or equal to 80 w/w %, or greater than or equal to 90 w/w % at an equilibrium water content state. In some embodiments, the second water soluble polymer 40 is present in the article in an amount of less than or equal to 95 w/w %, less than or equal to 90 w/w %, less than or equal to 80 w/w %, less than or equal to 70 w/w %, less than or equal to 60 w/w %, less than or equal to 50 w/w %, less than or equal to 40 w/w %, less than or equal to 30 w/w %, less than or equal to 20 w/w %, less than or equal to 10 w/w %, less than or equal to 5.0 w/w %, less than or equal to 4.0 w/w %, less than or equal to 3.0 w/w %, less than or equal to 2.0 w/w %, less than or equal to 1.0 w/w %, less than 0.5 w/w %, less than 0.2 w/w %, or less than 0.1 w/w % at an equilibrium water content state. In some embodiments, 0 w/w % of the second water soluble polymer is present. Combinations of the above-referenced ranges are also possible (e.g., greater than or equal to 0.05 w/w % and less than or equal to 95 w/w %). Other ranges are also possible.

In some embodiments, the water-soluble polymer (e.g., the first water soluble polymer, the second water soluble polymer, the third water soluble polymer) has a particular molecular weight. In some embodiments, the molecular weight of the water soluble polymer (e.g., each, independently, the first water soluble polymer, the second water soluble polymer, or the third water soluble polymer) may be greater than or equal to 40 kDa, greater than or equal to 50 kDa, greater than or equal to 75 kDa, greater than or equal to 100 kDa, greater than or equal to 125 kDa, greater than or equal to 150 kDa, greater than or equal to 175 kDa, greater than or equal to 200 kDa, greater than or equal to 250 kDa, greater than or equal to 300 kDa, greater than or equal to 350 kDa, greater than or equal to 400 kDa, greater than or equal to 450 kDa, greater than or equal to 500 kDa, greater than or equal to 600 kDa, greater than or equal to 700 kDa, greater than or equal to 800 kDa, greater than or equal to 900 kDa, greater than or equal to 1000 kDa, greater than or equal to 1500 kDa, greater than or equal to 2000 kDa, greater than or equal to 3000 kDa, or greater than or equal to 4000 kDa. In some embodiments, the molecular weight of the water soluble polymer (e.g., each, independently, the first water soluble polymer, the second water soluble polymer, or the third water soluble polymer) may be less than or equal to 5000 kDa, less than or equal to 4000 kDa, less than or equal to 3000 kDa, less than or equal to 2000 kDa, less than or equal to 1500 kDa, less than or equal to 1000 kDa, less than or equal to 900 kDa, less than or equal to 800 kDa, less than or equal to 700 kDa, less than or equal to 600 kDa, less than or equal to 500 kDa, less than or equal to 450 kDa, less than or equal to 400 kDa, less than or equal to 350 kDa, less than or equal to 300 kDa, less than or equal to 250 kDa, less than or equal to 200 kDa, less than or equal to 175 kDa, less than or equal to 150 kDa, less than or equal to 125 kDa, less than or equal to 100 kDa, less than or equal to 75 kDa, or less than or equal to 50 kDa. Combinations of the above-referenced ranges are also possible (e.g., a molecular weight of greater than or equal to 40 kDa and less than or equal to 5000 kDa). Other ranges are also possible.

In some embodiments, the articles (e.g., article 10 of FIG. 1A, article 12 of FIG. 1B) (and/or polymeric materials) described herein are, or are configured for use with, a medical device such as a catheter, a balloon, a shunt, a wound drain, an infusion port, a drug delivery device, a tube, a contraceptive device, a feminine hygiene device, an endoscope, a graft, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device. In some embodiments, the catheter is selected from the group consisting of central venous catheters, peripheral central catheters, midline catheters, peripheral catheters, tunneled catheters, dialysis access catheters, urinary catheters, neurological catheters, percutaneous transluminal angioplasty catheters and/or peritoneal catheters. Other suitable uses are described in more detail, below.

Figure 37A:
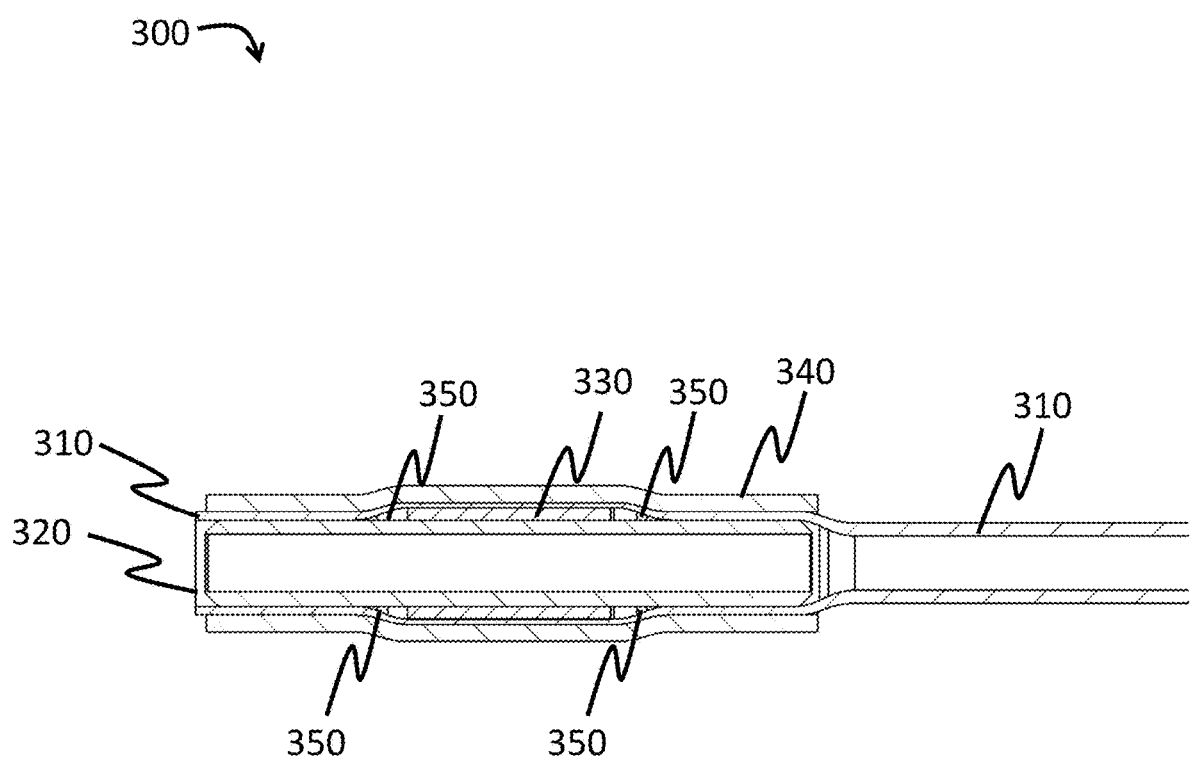
FIG. 37A is a cross-sectional schematic diagram of an exemplary article having a first component and a second component, according to one set of embodiments.
Figure 37B:
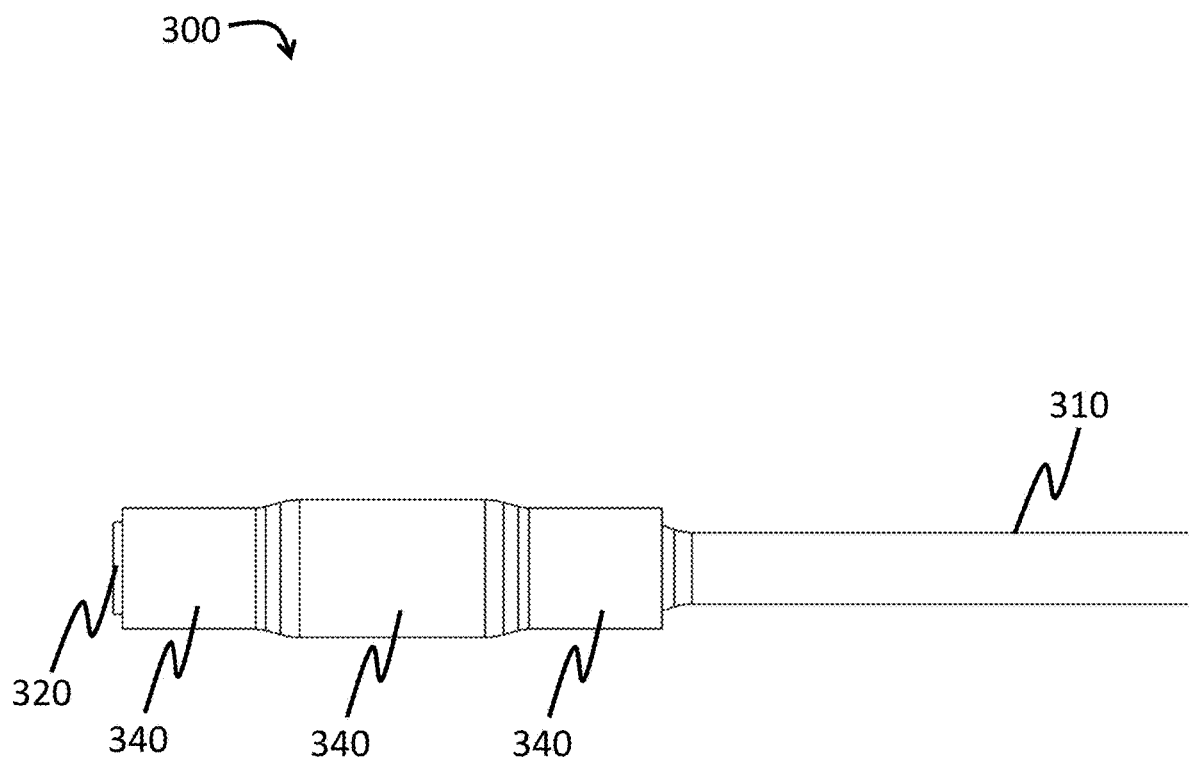
FIG. 37B is a side-view schematic diagram of an exemplary article having a first component and a second component, according to one set of embodiments.

In some embodiments, the article (e.g., article 10 of FIG. 1A, article 12 of FIG. 1B) comprises a first component comprising a polymeric material (e.g., comprises a water-soluble polymer) and a second component adjacent the first component. For example, in some cases, the second component is mechanically coupled to the first component. In some such embodiments, the second component may comprise a plurality of surface features configured to mechanically retain the second component within or on the first component. In some embodiments, as illustrated in FIGS. 37A-37B, article 300 comprises first component 310 (e.g., an article such as article 10 of FIG. 1A or article 12 of FIG. 1B) and second component 320 (e.g., an extension, a connector, a luer lock, a suture wing, a second article such as article 10 of FIG. 1A or article 12 of FIG. 1B), adjacent first component 310. In some embodiments, a first thermoplastic layer 330 is disposed between first component 310 and second component 320. In some embodiments, optional second thermoplastic layer 340 is adjacent (e.g., in contact with an external surface of) first component 310. In some cases, second component 320 may comprise plurality of surface features 350 associated with first component 310, such that the second component is mechanically retained to (e.g., within, on, adjacent) first component 310.

In some embodiments, the second component may be a connector (e.g., to a medical component and/or a medical device). In some embodiments, the second component may be selected from the group consisting of an extender, a connector, a luer lock, and a suture wing. In some embodiments, the second component may be another article, such as the articles described herein, comprising a polymeric material.

In some embodiments, the article (e.g., article 10 of FIG. 1A, article 12 of FIG. 1B) comprises a first thermoplastic layer disposed between the first component and the second component (e.g., to aid with mechanical retention between the first and second components). In some cases, a second thermoplastic layer may be in contact with an external surface of the first component. For instance, the second thermoplastic layer may cover both a portion of the second component and a portion of the first component. Each thermoplastic layer may comprise a suitable thermoplastic material. In some embodiments, the first thermoplastic material and/or second thermoplastic material each independently comprise or are selected from the group consisting of polyurethane elastomers, silicone elastomers, silicone-polyurethane copolymer, polyethylene, polypropylene, styrene isoprene butadiene copolymer, homopolymers and copolymers of vinyl acetate such as ethylene vinyl acetate copolymer, polyvinylchlorides, homopolymers and copolymers of acrylates and methacrylates, polyvinylpyrrolidone, 2-pyrrolidone, polyacrylonitrile butadiene, polycarbonates, polyamides, polyether block amide, fluoropolymers (including homopolymers and copolymers of polytetrafluoroethylene and polyvinyl fluoride), fluorinated ethylene propylene, polystyrenes, homopolymers and copolymers of styrene acrylonitrile, homopolymers and copolymers of styrene butadiene, cellulose acetate, homopolymers and copolymers of acrylonitrile butadiene styrene, polymethylpentene, polysulfones, polyesters, polyimides, polyisobutylene, polymethylstyrene, polyoxymethylene, and homopolymers and copolymers of poly(lactic acid), poly(glycolic acid), and poly(caprolactone). In some embodiments, the first thermoplastic material and/or the second thermoplastic material at least partially swells in water at 25° C.

In some embodiments, the second component is thermally bonded to the first component. In some embodiments, the second component is solvent-bonded to the first thermoplastic material. In some embodiments, the solvent may be selected based on the ability to solvate both the first component and/or the second component. Non-limiting examples of suitable solvents include: tetrahydrofuran, toluene, N,N-dimethylformamide, N,N-dimethylacetamide, chloroform, dichloromethane, ethyl acetate, acetone, acetonitrile, dimethyl sulfoxide, nitromethane, propylene carbonate, diethyl ether, 1,4-doxane, benzene, cyclohexane, hexane, cyclopentane, pentane, formic acid, n-butanol, isopropyl alcohol, ethanol, methanol, acetic acid, hexafluoroisopropanol, trifluoroacetic acid, water, and combinations thereof. In an exemplary embodiment, a water-swelling polyurethane is solvent bonded to a hydrophobic polyurethane using tetrahydrofuran.

In some embodiments, the second component has a Young's elastic modulus greater than a Young's elastic modulus of the first component in the dehydrated state and/or in the equilibrium water content state. In some embodiments, the second component has a Young's elastic modulus greater than a Young's elastic modulus of the first component in the equilibrium water content state, but less than a Young's elastic modulus of the first component in the dehydrated state.

In some embodiments, the second component comprises a plurality of surface features, such as protrusions or spikes. The surface features may be present at the interface between the first component and the second component so as to mechanically retain connection between the two components. In some embodiments, the plurality of surface features comprise rounded edges. In some embodiments, the plurality of surface features comprise rounded edges, sharp edges, blunt edges, flairs, bulges, and/or raised features. In some embodiments, the plurality of surface features comprise a plurality of barbs and/or bulges. Other surface features are also possible.

In some embodiments, the plurality of surface features may have a particular radius of curvature (e.g., at the surface adjacent the first component). For example, in some cases, at least a portion of the plurality of surface features have a radius of curvature of greater than or equal to 0.1, greater than or equal to 0.2, greater than or equal to 0.3, greater than or equal to 0.5 greater than or equal to 0.7 greater than or equal to 0.9, greater than or equal to 1, greater than or equal to 1.1, greater than or equal to 1.2, greater than or equal to 1.5, greater than or equal to 2, greater than or equal to 2.5, greater than or equal to 3, greater than or equal to 3.5, greater than or equal to 4, or greater than or equal to 4.5 times the radius of curvature of an inner surface of the article (e.g., the hollow portion of the article). In some embodiments, at least a portion of the plurality of surface features have a radius of curvature of less than or equal to 5, less than or equal to 4.5, less than or equal to 4, less than or equal to 3.5, less than or equal to 3, less than or equal to 2.5, less than or equal to 2, less than or equal to 1.5, less than or equal to 1.2, less than or equal to 1.1, less than or equal to 1, less than or equal to 0.9, less than or equal to 0.7, less than or equal to 0.5, less than or equal to 0.3, or less than or equal to 0.2 times the radius of curvature of an inner surface of the article (e.g., the hollow portion of the article). Combinations of the above-referenced ranges are also possible (e.g., greater than or equal to 0.1 and less than or equal to 5 times). Other ranges are also possible.

In some embodiments, the joint strength between the first component and the second component (e.g., at an interface between the first component and the second component) is greater than or equal to 10 N, greater than or equal to 15 N, greater than or equal to 20 N, greater than or equal to 25 N, greater than or equal to 30 N, greater than or equal to 40 N, greater than or equal to 50 N, greater than or equal to 60 N, greater than or equal to 70 N, or greater than or equal to 75 N. In some embodiments, the joint strength is less than or equal to 100 N, less than or equal to 75 N, less than or equal to 70 N, less than or equal to 60 N, less than or equal to 50 N, less than or equal to 40 N, less than or equal to 30 N, less than or equal to 25 N, less than or equal to 20 N, or less than or equal to 15 N. Combinations of the above-referenced ranges are also possible (e.g., greater than or equal to 10 N and less than or equal to 100 N). Other ranges are also possible. Joint strength may be determined as described in Example 26.

In some embodiments, an interface between the first component and the second component is fluidically sealed. For example, in some embodiments, the interface between the first component and the second component is configured to withstand an injection pressure (an injection of fluid through the first component and into the second component fluidically connected to the first component) of greater than or equal to 50 PSI, greater than or equal to 75 PSI, greater than or equal to 100 PSI, greater than or equal to 125 PSI, greater than or equal to 150 PSI, greater than or equal to 175 PSI, greater than or equal to 200 PSI, greater than or equal to 225 PSI, greater than or equal to 250 PSI, greater than or equal to 300 PSI, or greater than or equal to 350 PSI. In some embodiments, the interface between the first component and the second component is configured to withstand an injection pressure of less than or equal to 500 PSI, less than or equal to 400 PSI, less than or equal to 350 PSI, less than or equal to 300 PSI, less than or equal to 250 PSI, less than or equal to 225 PSI, less than or equal to 200 PSI, less than or equal to 175 PSI, less than or equal to 150 PSI, less than or equal to 125 PSI, less than or equal to 100 PSI, or less than or equal to 75 PSI. Combinations of the above-referenced ranges are also possible (e.g., greater than or equal to 50 PSI and less than or equal to 500 PSI). Other ranges are also possible.

As described herein, in some embodiments, the article (e.g., article 10 of FIG. 1A, article 12 of FIG. 1B) comprises at least a first thermoplastic layer disposed between the first component and the second component. In some embodiments, the second component is placed on or adjacent to the first component prior to sorption of a second water-soluble polymer. In some embodiments, the second component is placed on or adjacent to the first component after sorption of a second water-soluble polymer and after a re-extraction of the second water-soluble polymer with a solvent. In some embodiments, the article comprises a first component comprising a water-soluble polymer and a plurality of pores, a second component comprising a first thermoplastic material positioned within at least a portion of the plurality of pores, and a third component comprising a second thermoplastic material associated with (e.g., adjacent, directly adjacent, or on) the second component.

These materials can be made as tough, high strength materials having lubricious and biocompatible surfaces. Nanoporous and microporous solids are described herein that have a particularly high Young's modulus and tensile strength. A nanoporous material is a solid that contains interconnected pores of up to 100 nm in diameter. Processes for making hydrogels are also described. Hydrophilic polymers may be used to make these various porous solids so that a hydrophilic solid is obtained. The water content of a nanoporous or a microporous solid can be high, e.g., 50% w/w at EWC. The water content of a hydrogel may be higher, for example, up to 90% w/w in principle. The porous solid materials can be used to make various devices, including medical catheters and implants with significant reductions in adsorption and/or adhesion of biological components to their surfaces.

These or other porous materials may be processed to include polymers that are bulk-incorporated into pores of the solid. An embodiment of the material is a porous material comprising water soluble polymers entrapped in pores of the material. Polymers entrapped by this method have been observed to be present in the pores and to remain in the pores after repeated hydration and dehydration. The entrapped polymers provide a surface that is scratch-resistant and effectively permanent, with the incorporated polymer providing desirable properties beyond the outer surface of the material. In aqueous medium, hydrophilic polymers entrapped by this method are hydrated to extend beyond the surface to enhance biocompatibility and lubricity. Processes for making the material can include extrusion so that devices with a high aspect ratio may be created. An embodiment of a process for making the materials involves heating a mixture that comprises at least one water soluble polymer and a solvent to a temperature above the melting point of the polymer solution forming the mixture in a solvent-removing environment resulting in a crosslinked matrix and continuing to remove the solvent until the crosslinked matrix is a microporous or a nanoporous solid material. The crosslinking can take place while cooling the mixture and/or in the solvent-removing environment. Further polymers may be incorporated into pores of the material.

Disclosed herein are forming processes, including extrusion, to make a high strength porous solid. Guidance as to processes and parameters to make porous solids are disclosed, as well as the porous solids. Guidance for bulk incorporation of polymers into porous solids is disclosed. Porous solids are disclosed with good properties and the further inclusion of bulk incorporated polymers provides further improvements.

Various techniques for making solid plastic materials are known. These conventionally include processes that force a polymeric material through an opening under conditions where the polymeric material forms into a solid plastic as it passes through the opening. Typically, there is a heating phase to soften or melt the polymer, a shaping/forming phase wherein the polymer is in a flowable form and under some kind of constraint, and a cooling phase wherein the shaped/formed polymer is cooled to a temperature at which it retains its shape. The plastic may undergo some changes after it passes through the opening, such as shrinkage, solvent removal, or crosslinking but its shape is fixed when it solidifies. Thermoplastics can be remelted. Some thermoplastics form strong interchain and/or intra-chain bonds that are non-covalent crosslinks and are referred to as physical crosslinks to distinguish them from covalent bonds. Thermosets are formed irreversibly with covalent crosslinks.

Examples of forming processes are thermoforming, molding processes, and extrusion processes. Extrusion processes typically involve forcing a polymeric material through a shaped die under pressure. Pellets of polymer are commonly fed into a hopper that enters a screw extruder that compresses and melts the polymer as it is conveyed to the die. After passing through an opening in the die, the polymer rapidly cools and sets in a solid shape. Extrusion can also include a drawing process. Many complex shapes can be formed with extrusion processes, including tubes with one or more lumens, coatings, layered coatings, filaments, hollow profiled objects, objects with cross sections that are round, square polygonal, or complex, and copolymeric extrusions involving multiple polymers combined in the extruder or die. The term die is used broadly herein to encompass openings that polymers pass through in an extrusion process to form a solid, and includes dies that involve one or more of a mandrel, combinations of dies, port hole dies, dies with a plurality of openings that cooperate to make an extruded product, dies that cooperate with a core, dies that cooperate with core tubing, core wire, blown air or gas that serves as a core, or slit dies. A core is useful to provide a lumen for a continuously extruded product and may be used temporarily for a device with a hollow lumen or permanently in the case of a coated device, for example a coated wire. Almost any shape can be created with a die so long as the created shape has a continuous profile. The term continuous is a term of art that refers to theoretically producing indefinitely long material even through a semi-continuous, intermittent, or other processes can be used.

Extrusion processes conventionally involve heating a polymer and passing it out of a die while it is hot to be rapidly cooled so as to set the plastic shape. The choice of temperatures and conditions depends on factors such as the polymer's chemical composition and molecular weight, melting temperature (Tm), glass transition temperature (Tg), presence of crosslinks, and effects caused by solvents if they are present. Tm marks a transition between a crystalline or semi-crystalline phase to a liquid amorphous phase. Tg marks a temperature at which amorphous polymers undergo a transition from a rubbery, viscous liquid, to a brittle, glassy amorphous solid on cooling. Amorphous polymers have a Tg but do not have a specific melting point, Tm. A conventional extrusion process generally involves processing the polymer at a high temperature while it is in the extruder, with temperatures of more than 150° C. being typical.

Herein is disclosed a new process that provides for extrusion of high strength materials. Some embodiments of the process provide one or more of: removal of a solvent from a hydrophilic polymer-solvent mixture as the material is extruded, extruding at a cold temperature, extruding into a solvent-removing environment, and further removal of solvent for a period of time after extrusion. Further, an annealing phase and/or a bulk incorporation for further polymers phase may also be included.

Figure 1C:
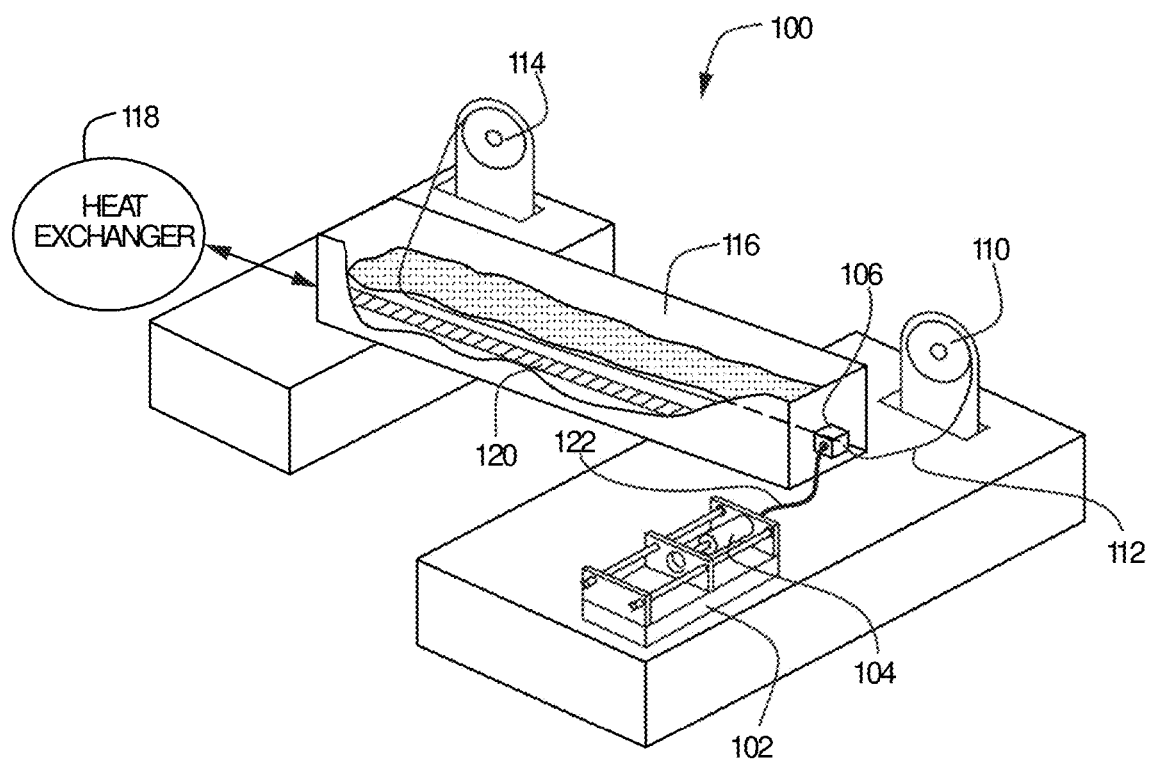
FIG. 1C is a schematic of an extrusion apparatus to form a continuous form with a cut-away view of a side of the bath.
Figure 1D:
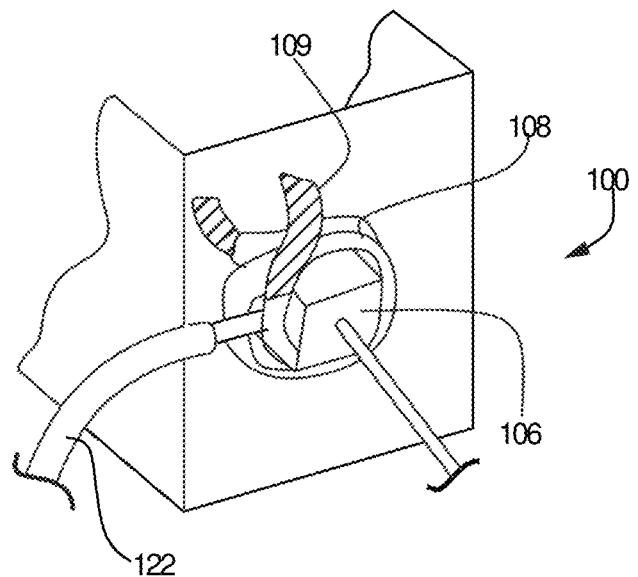
FIG. 1D is an enlarged view of a portion of the apparatus of FIG. 1C depicting the die head in perspective as viewed from the outside of the bath.
Figure 1E:
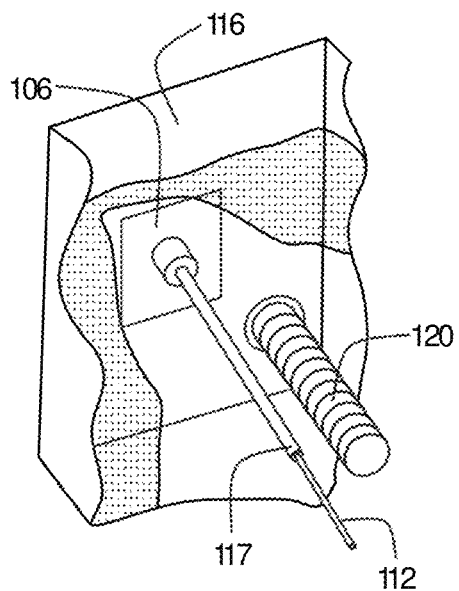
FIG. 1E is an enlarged view of a portion of the apparatus of FIG. 1C depicting the die head as disposed in the bath.

FIGS. 1C-1E depict an embodiment of an apparatus to make the porous solid materials. A device 100 as depicted includes a syringe pump 102 to accept at least one syringe 104, an optional heating jacket (not shown) to heat the syringes, die head 106, heating element 108 and power cables 109 for the same, providing heating as needed for die head 106 (detail not shown in FIG. 1C), dispensing spool 110 for core tubing 112, uptake spool 114 and motor (not shown) for core tubing, bath 116 for the extruded material 117, with the bath having temperature control for cooling or heating, depicted as heat exchanger 118 that comprises heat exchanging pipe 120 in bath 116. Die head 106 accepts the core tubing 110 which passes therethrough. Feed line 122 from the syringes to die head 106 provides a feed to device 100. A system for this embodiment may further include a weigh station, a jacketed vessel for heating and mixing solutions for loading into the syringes, and a solvent-removal environment for further drying of tubing removed from bath 116. The system may also have a heating station for annealing the tubing or other extrusion product with heat when desired. Core tubing made of PTFE as well as wires, air, gas, non-solvent liquid or other materials may be used for a core.

In use, by way of example, a polymer is heated in a suitable solvent in a jacketed vessel and placed into syringe 104. One or more polymers may be present and a radiopaque agent or other additive may be added. One or more syringes may be used with the same or different mixtures. The syringe(s) of the polymer are heated to a predetermined temperature, e.g., of no more than 80-95° C., and degassed before extrusion. Syringe 104 is mounted on syringe pump 102 with a wrap heater to maintain temperature during extrusion. Core 112 is looped through die head 106, e.g., a heated out-dwelling die head, which feeds into extrusion bath 116, and then attached to an uptake spool 114 that is driven by a motor. The temperature of the bath is controlled using heat exchanger 118, such as a chiller; extruded materials may be extruded at temperatures ranging from −30° C. to 75° C.; other temperatures may be used, and 0° C. is a generally useful temperature setting for extrusion. Artisans will immediately appreciate that all ranges and values between the explicitly stated bounds are contemplated, with, e.g., any of the following being available as an upper or lower limit: −30, −25, −20, −15, −10, −5, 0, 5, 10, 15, 20, 25, 30, 35, 40, 45, 50, 55, 60, 65, 70, 75° C. Uptake (e.g., puller) spool 114 motor speed can be controlled to adjust outer diameter gauge size around core 112. Adjusting die size, material feed rate, tubing core diameter, and puller speed play roles in adjusting final tubing gauge, e.g., in embodiments wherein a catheter is made. Polymer feed rates are adjustable, e.g., by control of syringe pump 102 in this embodiment. Connectors 122 join the one or more syringes to die head 106. Many pumps and other tools for controllably feeding a polymer solution are known. The apparatus and method can be adapted for a drawing process although alternative feed processes are available.

In some embodiments, a composition (e.g., a pre-polymer composition) may be provided (e.g., for extrusion) prior to formation of the polymeric material. In some embodiments, the composition comprises an aqueous solution. The aqueous solution can comprise an osmotic agent at a concentration of greater than or equal to 0.1 M and less than or equal to 8 M. The aqueous solution can comprise a radiopaque agent in an amount of greater than or equal to 0 w/w % and less than or equal to 40 w/w %. The composition can further comprise a water-soluble polymer having a molecular weight of greater than or equal to 40 kDa and less than or equal to 5000 kDa, and present in the solution in an amount greater than or equal to 10 w/w % and less than or equal to 50 w/w %.

In some embodiments, the composition forms a swellable polymeric material upon extrusion.

In some embodiments, the osmotic agent is present in the solution at a concentration of greater than or equal to 0.1 M, greater than or equal to 0.5 M, greater than or equal to 1 M, greater than or equal to 2 M, greater than or equal to 3 M, greater than or equal to 4 M, greater than or equal to 5 M, or greater than or equal to 6 M. In some embodiments, the osmotic agent is present in the solution at a concentration of less than or equal to 8 M, less than or equal to 6 M, less than or equal to 4 M, less than or equal to 2 M, less than or equal to 1 M, or less than or equal to 0.5 M. Combinations of the above-referenced ranges are also possible (e.g., greater than or equal to 0.1 M and less than or equal to 8 M). Osmotic agents are described in more detail herein.

In some embodiments, the radiopaque agent is present in the solution in an amount of greater than or equal to 0 w/w %, greater than or equal to 5 w/w %, greater than or equal to 10 w/w %, greater than or equal to 15 w/w %, greater than or equal to 20 w/w %, greater than or equal to 25 w/w %, greater than or equal to 30 w/w %, or greater than or equal to 35 w/w %. In some embodiments, the radiopaque agent is present in the solution in an amount less than or equal to 40 w/w %, less than or equal to 35 w/w %, less than or equal to 30 w/w %, less than or equal to 25 w/w %, less than or equal to 20 w/w %, less than or equal to 15 w/w %, less than or equal to 10 w/w %, or less than or equal to 5 w/w %. Combinations of the above-referenced ranges are also possible (e.g., greater than or equal to 0 w/w % and less than or equal to 40 w/w %). Other ranges are also possible. Radiopaque agents are described in more detail, below.

In some embodiments, the water-soluble polymer is present in the solution in an amount greater than or equal to 10 w/w %, greater than or equal to 13 w/w %, greater than or equal to 15 w/w %, greater than or equal to 20 w/w %, greater than or equal to 25 w/w %, greater than or equal to 30 w/w %, greater than or equal to 35 w/w %, greater than or equal to 40 w/w %, or greater than or equal to 45 w/w %. In some embodiments, the water-soluble polymer is present in the solution in an amount less than or equal to 50 w/w %, less than or equal to 45 w/w %, less than or equal to 40 w/w %, less than or equal to 35 w/w %, less than or equal to 30 w/w %, less than or equal to 25 w/w %, less than or equal to 20 w/w %, less than or equal to 15 w/w %, or less than or equal to 13 w/w %. Combinations of the above-referenced ranges are also possible (e.g., greater than or equal to 10 w/w % and less than or equal to 50 w/w %). In some embodiments, the water-soluble polymer is present in the solution in an amount greater than or equal to 13 w/w %.

In some embodiments, the method for forming the polymeric materials and/or articles described herein comprises providing a mixture comprising a first water soluble polymer and an osmotic agent (e.g., a salt) as described above. In some embodiments, the mixture is extruded. In some embodiments, the extruded mixture is extruded on a core material to form the polymeric material disposed on the core material. In some embodiments, the formed polymeric material is exposed to a non-solvent of the polymeric material. In some embodiments, a solution comprising a second water soluble polymer different that the first water soluble polymer and, optionally, an osmotic agent, is introduced to the polymeric material. In some embodiments, the polymeric material (e.g., after introducing the solution to the osmotic agent) is heated. In some embodiments, the solution is flowed against the polymeric material. In some embodiments, the polymeric material may be dried.

In an exemplary set of embodiments, the method for forming the polymeric materials and/or articles described herein comprises providing a mixture comprising a first water soluble polymer and an osmotic agent, wherein the first water soluble polymer is present in the mixture in an amount greater than or equal to 10 w/w % (e.g., greater than or equal to 13 w/w % and less than or equal to 50 w/w %) versus the total weight of the mixture, performing the steps of: extruding the mixture at a temperature greater than or equal to 65° C. (e.g., greater than or equal to 65° C. and less than or equal to 100° C.) at atmospheric pressure, on a core material to form the polymeric material disposed on the core material, exposing the polymeric material to a non-solvent of the polymeric material at a temperature less than or equal to 28° C. (e.g., less than or equal to 28° C. and greater than or equal to −20° C.) for greater than or equal to 1 hour (e.g., greater than or equal to 1 hour and less than or equal to 240 hours), introducing, to the polymeric material, a solution comprising a second water soluble polymer, different than the first water soluble polymer, and an osmotic agent (e.g., a salt), heating the polymeric material and the solution to a temperature of greater than or equal to 25° C. (e.g., greater than or equal to 25° C. and less than or equal to 65° C.), flowing the solution adjacent the polymeric material for greater than or equal to 3 hours (e.g., greater than or equal to 3 hours and less than or equal to 48 hours), and drying the polymeric material.

In some embodiments, the second water soluble polymer is positioned in at least one pore (or a plurality of pores) of the first water soluble polymer, as described herein.

In some embodiments, the non-solvent comprises alcohol. In some embodiments, the non-solvent is ethanol, methanol, propanol, butanol, pentanol, hexanol, heptanol, octanol, decanol, dodecanol, dimethyl sulfoxide, ethyl acetate, acetates, propionates, ethers, dimethyl formamide, dimethyl acetamide, acetone, acetonitrile, ethylene glycol, propylene glycol, glycerol air, vacuum or combinations thereof. Other non-solvents are also possible (e.g., a solvent having a high solubility to water but a lower solubility to the water-soluble polymer, as compared to the solubility in water).

In some embodiments, the step of extruding the mixture is performed under atmospheric pressure at a temperature of greater than or equal to 65° C., greater than or equal to 70° C., greater than or equal to 75° C., greater than or equal to 80° C., greater than or equal to 85° C., greater than or equal to 90° C., or greater than or equal to 95° C. In some embodiments, the step of extruding the mixture is performed under atmospheric pressure at a temperature of less than or equal to 100° C., less than or equal to 95° C., less than or equal to 90° C., less than or equal to 85° C., less than or equal to 80° C., less than or equal to 75° C., or less than or equal to 70° C. Combinations of the above-referenced ranges are also possible (e.g., greater than or equal to 65° C. and less than or equal to 100° C.). Other ranges are also possible. Those of ordinary skill in the art would understand, based upon the teachings of this specification, that additional pressures (e.g., greater than atmospheric pressure, less than atmospheric pressure) and/or temperatures are also possible.

In some embodiments, the step of exposing the polymeric material to a non-solvent of the polymeric material is performed at a temperature less than or equal to 28° C., less than or equal to 25° C., less than or equal to 20° C., less than or equal to 15° C., less than or equal to 10° C., less than or equal to 5° C., less than or equal to 0° C., less than or equal to −5° C., less than or equal to −10° C., or less than or equal to −15° C. In some embodiments, the step of exposing the polymeric material to a non-solvent of the polymeric material is performed at a temperature greater than or equal to −20° C., greater than or equal to −15° C., greater than or equal to −10° C., greater than or equal to −5° C., greater than or equal to 0° C., greater than or equal to 5° C., greater than or equal to 10° C., greater than or equal to 15° C., greater than or equal to 20° C., or greater than or equal to 25° C. Combinations of the above-referenced ranges are also possible (e.g., less than or equal to 28° C. and greater than or equal to −20° C.). Other ranges are also possible.

In some embodiments, the step of exposing the polymeric material to the non-solvent of the polymeric material is performed (e.g., at a temperature less than or equal to 28° C. and greater than or equal to −20° C.) for greater than or equal to 1 hour, greater than or equal to 2 hours, greater than or equal to 4 hours, greater than or equal to 6 hours, greater than or equal to 8 hours, greater than or equal to 10 hours, greater than or equal to 15 hours, greater than or equal to 20 hours, greater than or equal to 30 hours, greater than or equal to 40 hours, greater than or equal to 50 hours, greater than or equal to 60 hours, greater than or equal to 80 hours, greater than or equal to 100 hours, greater than or equal to 120 hours, greater than or equal to 140 hours, greater than or equal to 160 hours, greater than or equal to 180 hours, greater than or equal to 200 hours, or greater than or equal to 220 hours. In some embodiments, the step of exposing the polymeric material to the non-solvent of the polymeric material is performed for less than or equal to 240 hours, less than or equal to 220 hours, less than or equal to 200 hours, less than or equal to 180 hours, less than or equal to 160 hours, less than or equal to 140 hours, less than or equal to 120 hours, less than or equal to 100 hours, less than or equal to 80 hours, less than or equal to 60 hours, less than or equal to 50 hours, less than or equal to 40 hours, less than or equal to 30 hours, less than or equal to 20 hours, less than or equal to 15 hours, less than or equal to 10 hours, less than or equal to 8 hours, less than or equal to 6 hours, less than or equal to 4 hours, or less than or equal to 2 hours. Combinations of the above-referenced ranges are also possible (e.g., greater than or equal to 1 hour and less than or equal to 240 hours). Other ranges are also possible.

In some embodiments, the step of introducing to the polymeric material, a solution comprising a second water soluble polymer, different than the first water soluble polymer, and an optional osmotic agent (e.g., a salt) comprises heating the polymeric material and the solution to a temperature of greater than or equal to 25° C., greater than or equal to 30° C., greater than or equal to 35° C., greater than or equal to 40° C., greater than or equal to 45° C., greater than or equal to 50° C., greater than or equal to 55° C., or reater than or equal to 60° C. In some embodiments, the polymeric material and the solution are heated to a temperature less than or equal to 65° C., less than or equal to 60° C., less than or equal to 55° C., less than or equal to 50° C., less than or equal to 45° C., less than or equal to 40° C., less than or equal to 35° C., or less than or equal to 30° C. Combinations of the above-referenced ranges are also possible (e.g., greater than or equal to 25° C. and less than or equal to 65° C.). Other ranges are also possible.

In some cases, the solution may be flowed adjacent (e.g., directly adjacent) the polymeric material for a particular amount of time. In some embodiments, the solution is flowed adjacent the polymeric material for greater than or equal to 3 hours, greater than or equal to 5 hours, greater than or equal to 6 hours, greater than or equal to 8 hours, greater than or equal to 10 hours, greater than or equal to 12 hours, greater than or equal to 16 hours, greater than or equal to 20 hours, greater than or equal to 24 hours, greater than or equal to 28 hours, greater than or equal to 32 hours, greater than or equal to 36 hours, greater than or equal to 40 hours, or greater than or equal to 44 hours. In some embodiments, the solution is flowed adjacent the polymeric material for less than or equal to 48 hours, less than or equal to 44 hours, less than or equal to 40 hours, less than or equal to 36 hours, less than or equal to 32 hours, less than or equal to 28 hours, less than or equal to 24 hours, less than or equal to 20 hours, less than or equal to 16 hours, less than or equal to 12 hours, less than or equal to 10 hours, less than or equal to 8 hours, less than or equal to 6 hours, or less than or equal to 5 hours. Combinations of the above-referenced ranges are also possible (e.g., greater than or equal to 3 hours and less than or equal to 48 hours). Other ranges are also possible. Combinations of the above-referenced temperatures and times are also possible.

In some embodiments, the method comprises annealing the polymeric material to a temperature of greater than or equal to 80° C. (e.g., greater than or equal to 80° C. and less than or equal to 250° C.) for greater than or equal to 60 minutes (e.g., greater than or equal to 60 minutes and less than or equal to 480 minutes). In some embodiments, the polymeric material is annealed at a temperature of greater than or equal to 80° C., greater than or equal to 90° C., greater than or equal to 100° C., greater than or equal to 120° C., greater than or equal to 140° C., greater than or equal to 160° C., greater than or equal to 180° C., greater than or equal to 200° C., greater than or equal to 220° C., or greater than or equal to 240° C. In some embodiments, the polymeric material is annealed at a temperature of less than or equal to 250° C., less than or equal to 240° C., less than or equal to 220° C., less than or equal to 200° C., less than or equal to 180° C., less than or equal to 160° C., less than or equal to 140° C., less than or equal to 120° C., less than or equal to 100° C., or less than or equal to 90° C. Combinations of the above-referenced ranges are also possible (e.g., greater than or equal to 80° C. and less than or equal to 250° C.). Other ranges are also possible.

In some embodiments, the polymeric material is annealed for greater than or equal to 60 minutes, greater than or equal to 80 minutes, greater than or equal to 100 minutes, greater than or equal to 120 minutes, greater than or equal to 160 minutes, greater than or equal to 200 minutes, greater than or equal to 240 minutes, greater than or equal to 280 minutes, greater than or equal to 320 minutes, greater than or equal to 360 minutes, greater than or equal to 400 minutes, or greater than or equal to 440 minutes. In some embodiments, the polymeric material is annealed for less than or equal to 480 minutes, less than or equal to 440 minutes, less than or equal to 400 minutes, less than or equal to 360 minutes, less than or equal to 320 minutes, less than or equal to 280 minutes, less than or equal to 240 minutes, less than or equal to 200 minutes, less than or equal to 160 minutes, less than or equal to 120 minutes, less than or equal to 100 minutes, or less than or equal to 80 minutes. Combinations of the above-referenced ranges are also possible (e.g., greater than or equal to 60 minutes and less than or equal to 480 minutes). Other ranges are also possible. Combinations of the above-referenced temperatures and times are also possible.

In some embodiments, the core material may be air, water, a non-solvent liquid, a solid, or a gas. In some cases, the core material may be removed after formation of the polymeric material on the core material. The core material may be physically removed and/or dissolved, in some cases.

In an exemplary embodiment, the method comprises, with a mixture (e.g., a solution as described above and herein) comprising at least one water soluble polymer, a salt, and water, wherein the at least one water soluble polymer is present in the mixture in an amount greater than or equal to 13 wt % versus the total weight of the mixture, performing the steps of: heating the mixture to a temperature greater than or equal to 65° C., after heating the mixture, cooling the mixture to a temperature at least 20° C. cooler than a melting point of the mixture and mechanically shaping the mixture. In some embodiments, after cooling the mixture, the mixture may be extruded at a temperature greater than or equal to 65° C. on a core material to form the polymeric material disposed on the core material. The method may involve exposing the polymeric material to non-solvent of the polymeric material at a temperature less than or equal to 28° C. for greater than or equal to 4 hours and removing at least a portion of the core material from the polymeric material.

In some embodiments, the step of cooling the mixture comprises cooling to a temperature at least 20° C., at least 25° C., at least 30° C., at least 35° C., at least 40° C., at least 45° C., at least 50° C., at least 60° C., at least 70° C., at least 80° C., or at least 90° C. cooler than a melting point of the mixture. In some embodiments, the step of cooling the mixture comprises cooling to a temperature of less than or equal to 100° C., less than or equal to 90° C., less than or equal to 80° C., less than or equal to 70° C., less than or equal to 60° C., less than or equal to 50° C., less than or equal to 45° C., less than or equal to 40° C., less than or equal to 35° C., less than or equal to 30° C., or less than or equal to 25° C. lower than a melting point of the mixture. Combinations of the above-referenced ranges are also possible (e.g., at least 20° C. and less than or equal to 100° C. lower). Other ranges are also possible. The mixture may be cooled for any suitable amount of time.

In some embodiments, the mixture may be mechanically shaped. In some embodiments, the composition (e.g., prior to extrusion i.e. the mixture) may be mechanically shaped by kneading, rolling, cutting, and combinations thereof.

In some embodiments, the method comprises mixing the mixture at an agitation speed of greater than or equal to 200 RPM (e.g., greater than or equal to 200 RPM and less than or equal to 5000 RPM). In some embodiments, the agitation speed is greater than or equal to 200 RPM, greater than or equal to 400 RPM, greater than or equal to 600 RPM, greater than or equal to 800 RPM, greater than or equal to 1000 RPM, greater than or equal to 1500 RPM, greater than or equal to 2000 RPM, greater than or equal to 2500 RPM, greater than or equal to 3000 RPM, greater than or equal to 3500 RPM, greater than or equal to 4000 RPM, or greater than or equal to 4500 RPM. In some embodiments, the agitation speed is less than or equal to 5000 RPM, less than or equal to 4500 RPM, less than or equal to 4000 RPM, less than or equal to 3500 RPM, less than or equal to 3000 RPM, less than or equal to 2500 RPM, less than or equal to 2000 RPM, less than or equal to 1500 RPM, less than or equal to 1000 RPM, less than or equal to 800 RPM, less than or equal to 600 RPM, or less than or equal to 400 RPM. Combinations of the above-referenced ranges are also possible (e.g., greater than or equal to 200 RPM and less than or equal to 5000 RPM, greater than or equal to 1000 RPM and less than or equal to 5000 RPM). Other ranges are also possible.

In some embodiments, the method comprises mixing the mixture at an agitation speed of greater than or equal to 200 RPM (e.g., greater than or equal to 1000 RPM) and at a temperature greater than or equal to 80° C.

In some embodiments, the mixture is mixed at a temperature of greater than or equal to 80° C., greater than or equal to 90° C., greater than or equal to 100° C., greater than or equal to 120° C., greater than or equal to 140° C., greater than or equal to 160° C., greater than or equal to 180° C., greater than or equal to 200° C., greater than or equal to 220° C., or greater than or equal to 240° C. In some embodiments, the mixture is mixed at a temperature of less than or equal to 250° C., less than or equal to 240° C., less than or equal to 220° C., less than or equal to 200° C., less than or equal to 180° C., less than or equal to 160° C., less than or equal to 140° C., less than or equal to 120° C., less than or equal to 100° C., or less than or equal to 90° C. Combinations of the above-referenced ranges are also possible (e.g., greater than or equal to 80° C. and less than or equal to 250° C.). Other ranges are also possible.

In some embodiments, the method comprises sorption of a second water-soluble polymer into the polymeric material, as described above and herein.

In some embodiments, the polymeric materials and/or articles described herein may be exposed to a humectant. In some embodiments, the humectant is a non-ionic surfactant (i.e. a surfactant having a net uncharged hydrophilic head and a hydrophobic tail comprising a carbon chain) or a zwitterionic surfactant. In some embodiments, the humectant is a non-ionic surfactant selected from the group consisting of poloxamer, triacetin, α-hydroxy acids, polyethylene glycol, polypropylene glycol, ethylene glycol, propylene glycol, hexylene glycol, butylene glycol, glycerol, sorbitol, mannitol, xylitol, maltitol, and combinations thereof.

aqueous solution and an average of 1.86 mm and 2.01 mm outer diameter for PVA-PAA and PVP-Iodine. These 6F catheters were made with PVA. Tensile strengths for several of the formulations were evaluated at equilibrium water content (EWC), and showed an increased strength as compared to the ISO-10555 standard requirements could be readily obtained. These samples not only met but exceeded ISO standards (see Table 1). They were flexible, e.g., a sample 30 cm in length could easily bent 90° by hand without kinking.

TABLE 1

| Sample | Avg. max tensile load [N] | % diff. ISO | Elongation at break | Young's modulus [N/mm²] (MPa) | max stress [N/mm²] (MPa) |
|---|---|---|---|---|---|
| PVA (5F), at EWC | 13.20 | +27.6% | 354% | 27.5 | 74.5 |
| PVA-PAA (6F), at EWC | 10.80 | +7.6% | 270% | 7.6 | 33.2 |
| PVP-Iodine (6F), at EWC | 11.35 | +12.6% | 268% | 12.57 | 24.4 |
| Fukumori (aGF-10), tested dry | Not reported | N/A | 6.3% | 8.9 | 180.6 |

Figure 3:
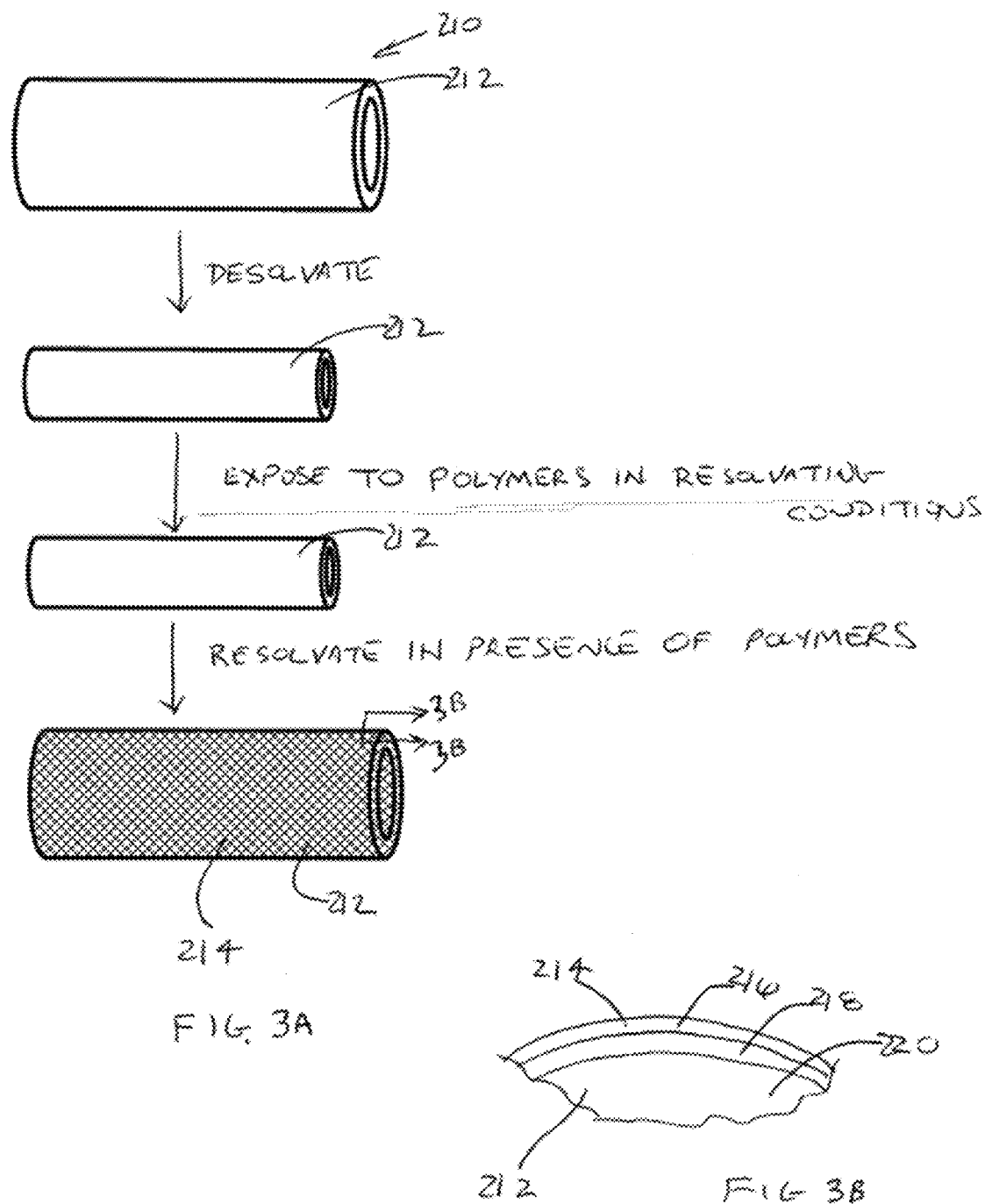
FIG. 3A is a schematic of a process of bulk incorporation of a polymer into a porous solid.
FIG. 3B is a cross-section of a portion of a tube taken along line 3B-3B of FIG. 3A.

A porous solid (e.g., made by the apparatus of FIGS. 1C-1E) may be annealed. Further, a porous solid, with or without prior annealing, may be processed to further include bulk incorporated polymers. In FIG. 3A, material 210 comprising porous solid matrix 212 is desolvated, exposed to a mixture comprising polymers that are in a resolvating solvent, and resolvated in the mixture to form material 212 with bulk incorporated polymers 214. A cross section of matrix 212 (FIG. 3B) reveals an outermost zone 216 wherein pores of matrix 212 are filled, an intermediate zone 218 wherein there is a lesser density of polymers in the pores, with less filling and/or fewer of the pores being occupied, and an inner zone 220 wherein polymers have not penetrated. The matrix can be solvated and/or desolvated prior to exposure to the mixture, provided that it is desolvated when exposed to the mixture so that water soluble polymers can be moved into the matrix.

Figure 4:
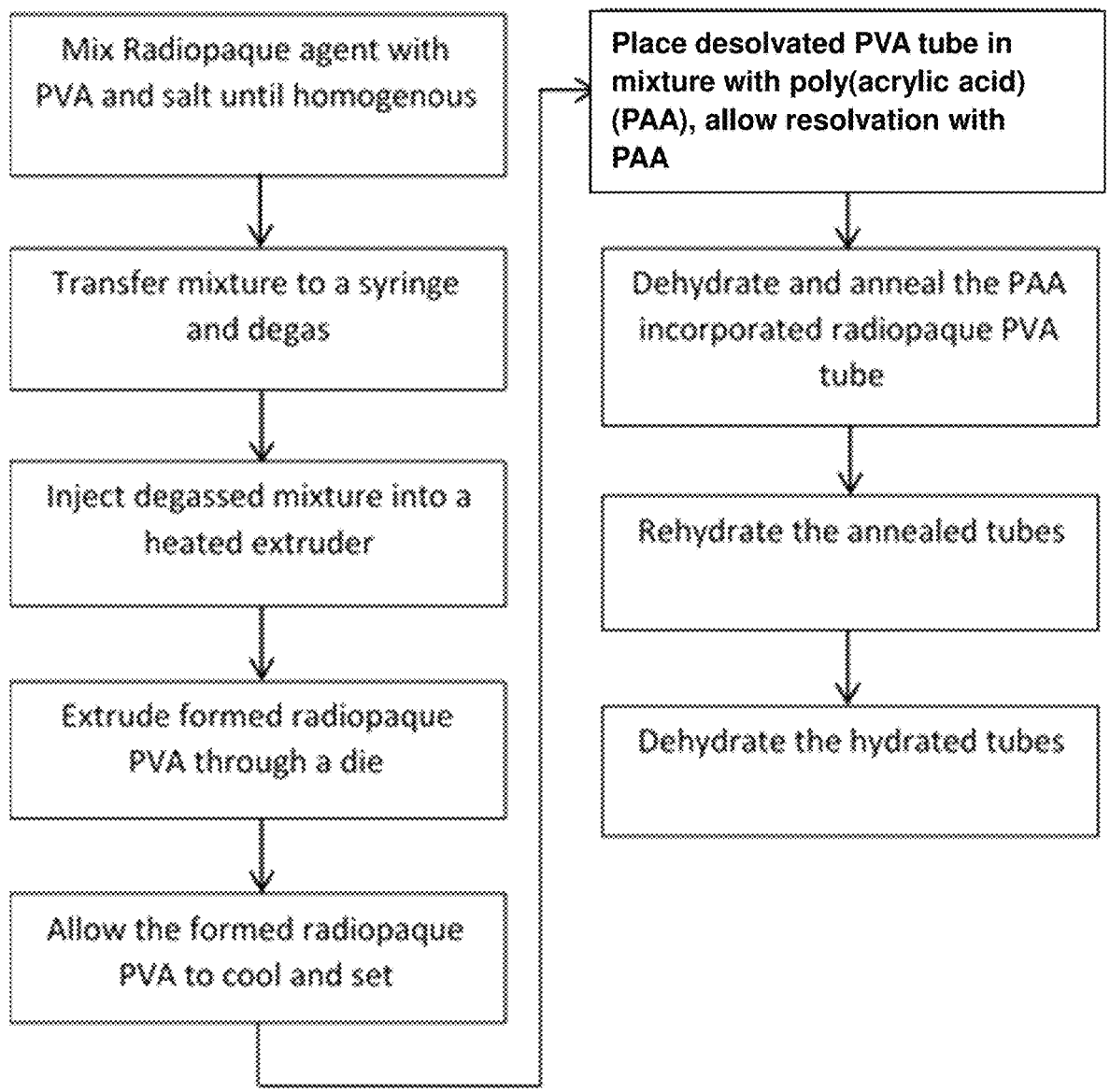
FIG. 4 is a process flow chart for an embodiment of bulk incorporating a surface polymer into a porous solid and includes an extrusion process for making the porous solid.

An exemplary flow chart for a process for making a porous solid including bulk incorporated polymers is presented in FIG. 4. In this process, a radiopaque (RO) agent is included in an extrusion process. The heated hydrophilic polymer solution refers to the polymers that are bulk incorporated into pores of the extruded porous solid.

Artisans reading this disclosure will be able to adapt its principles in light of what is known about extrusion or other forming arts to make alternative processes and devices that achieve the same end products as described herein. A scaled-up embodiment of this process may be adapted for use with, for example, a multi-zone screw extruder, with the solvent mixture provided via a suitable injector or a hopper and the zones controlled to provide a cold extrusion. Features such as the syringe pump can be replaced by a suitably metered and controlled liquid or solid polymer feed system.

The system for making porous materials has been used to make various products of porous solids, for example 6F catheters with the properties shown in Table 1. Samples were made using 13% w/w 85 kDa PVA with either 0.1% w/w 450 k PAA or 1% w/w 20 k PVP-iodine. In all cases, samples were extruded into chilled ethanol between 0° and 15° C., soaked in ethanol overnight, then dried. The chilled ethanol was never at a temperature that allowed for freezing of the samples. Samples were then annealed in glycerol at 120° C. between 6 and 17 hours, then rehydrated prior to testing. The samples were made with an average outer diameter of 1.59 mm (5F) after a few days of hydration in The tensile results in Table 1 were obtained from one batch of samples. The minimum strength required by ISO 10555-1:2013 is 2.25 for catheters with an OD between 1.14 and 1.82 mm and 3.37 lbs (15 N) for catheters large than 1.82 mm. Average strength of samples created using the finalized casting process (approximately 12 F) resulted in samples with tensile strength 164% greater than the required minimum tensile strength. Catheters and the like can be graded using the French nomenclature, which refers to an inner diameter in French (F) Fukumori et al. (2013), Open J. Organic Polymer Materials 3:110-116 reported a freeze-thaw process of making poly(vinyl alcohol) (PVA) materials with a Young's modulus of 181 MPa with a Young's modulus of about 5 MP or more requiring at least about 3 cycles in the samples they tested. The process of making these gels required multiple freeze-thaw cycles. The resultant materials were tested in a dry condition and are not comparable to strengths measured at EWC. Fukumori et al. reported that the crystalline content of the materials increased with the number of freeze-thaw cycles and attributed the strength of the materials to large crystals being formed as the freeze-thaw cycles progressed, with the larger crystals forming superior crosslinks that increased the Tg of the materials. The nature of these processes produces a dried material. Moreover, as discussed below, a freeze-thaw process produces macropores.

In contrast, processes herein are free of freeze-thaw processes and/or free of a freezing process and/or free of a thawing process. Further the processes can be used to make solid porous materials that have little or no swelling, e.g., 0%-100% w/w swelling at EWC, even in an absence of covalent crosslinking agents Artisans will immediately appreciate that all ranges and values between the explicitly stated bounds are contemplated, with, e.g., any of the following being available as an upper or lower limit: 0, 5, 10, 15, 20, 25, 30, 40, 50, 60, 70, 80, 90, 95, 100% w/w, with swelling measured as % swelling=100×(Total weight at EWC−dry weight)/dry weight, with the dry weight being the weight of the material without water.

Figure 5:
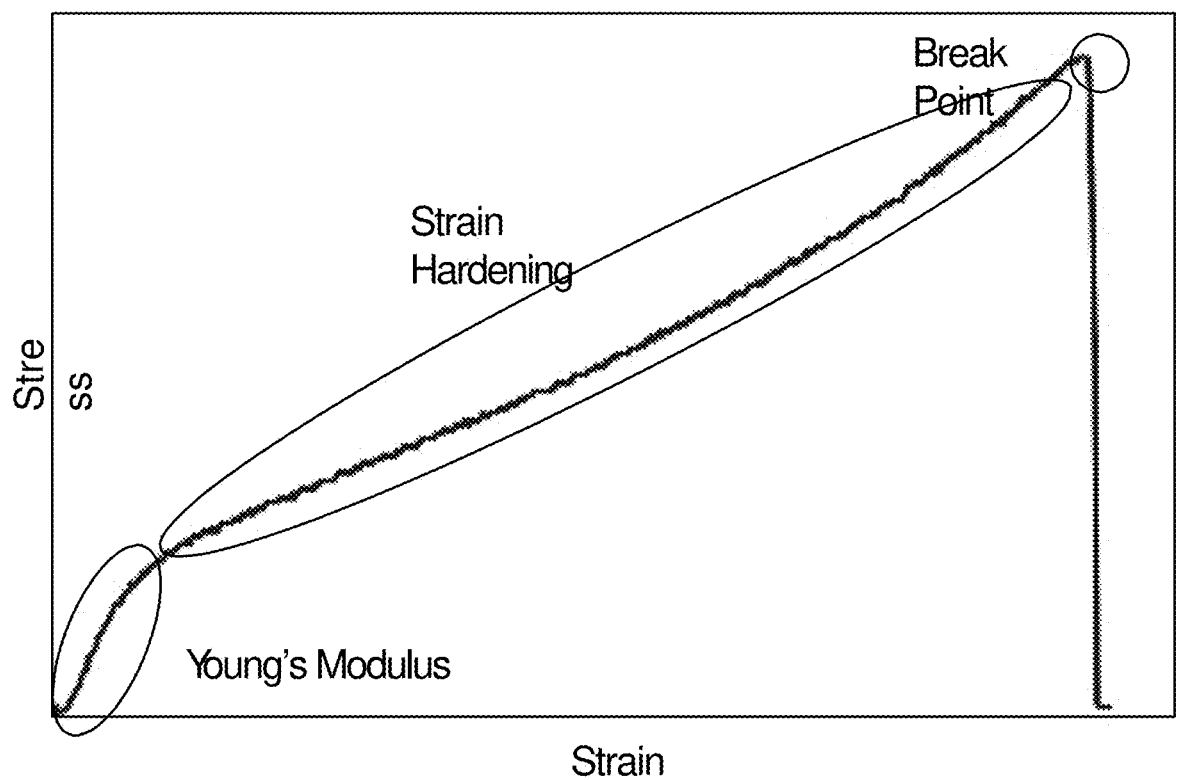
FIG. 5 is a plot depicting a stress-strain curve of a polymeric material.
Figure 6:
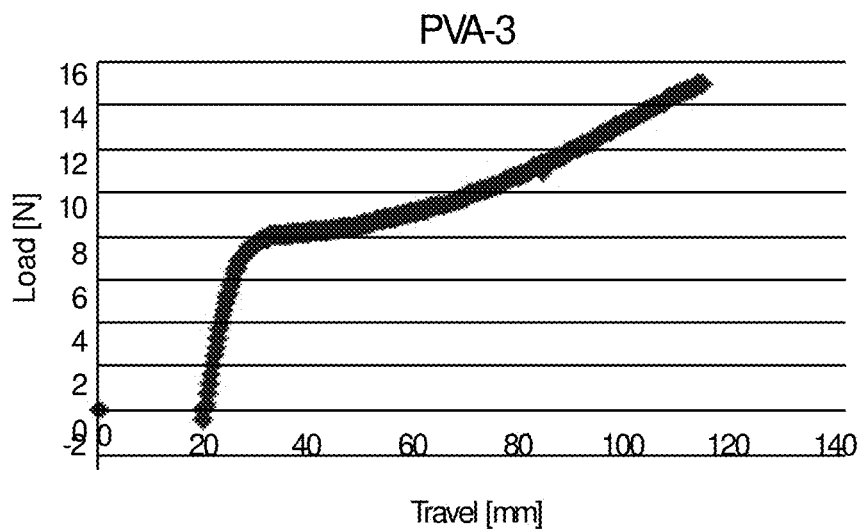
FIG. 6 is a plot of tensile test data for a porous solid made with the apparatus of FIGS. 1C-1E.

FIG. 5 shows the different zones of a polymeric material stress-strain curve. There are three major zones: Young's Modulus, strain hardening, and break point. Young's Modulus is defined as the slope (change of stress/change of strain) of the linear elasticity of a material. Strain hardening is defined as the strengthening of a material due to deformation. Break point is the point of maximum elongation. Tensile load and travel were plotted for a PVA (5F) sample as shown in FIG. 6. The shape of the load curve was representative of other samples which underwent tensile testing. The sharp initial slope and eventual leveling out as elongation occurs may indicate viscoelastic properties of the extruded PVA, where the material strain hardens and eventually undergoes strain softening until break. This particular sample exhibited a max tensile load of 14.9 N, with a travel of 115 mm (454% elongation). Other samples made with the same process to have an average diameter of 2.03 (6.4 F) have an average maximum tensile strength of 24.6 N (5.52 lbs.). This substantial increase in tensile strength accompanying such a slight increase in cross-sectional area indicates that catheters made of these materials will greatly surpass ISO 10555 minimum standards.

Figure 7:
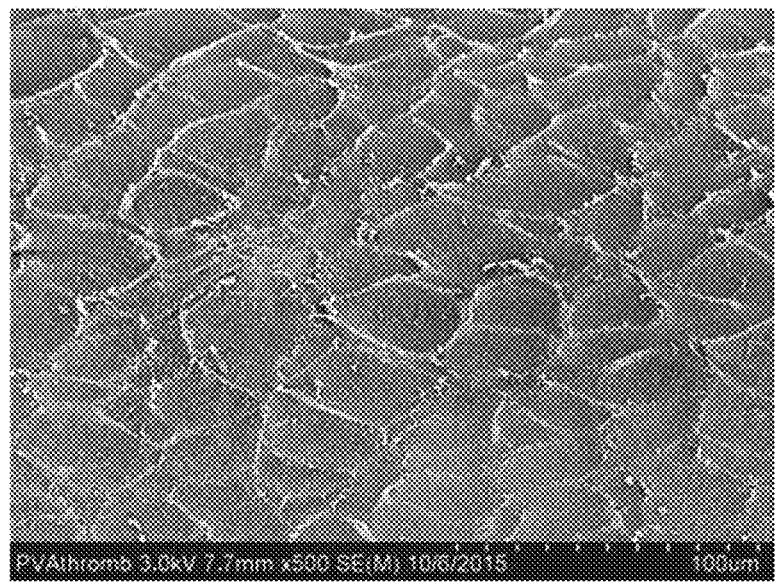
FIG. 7 is a scanning electron micrograph (SEM) of a surface of a porous solid.
Figure 8:
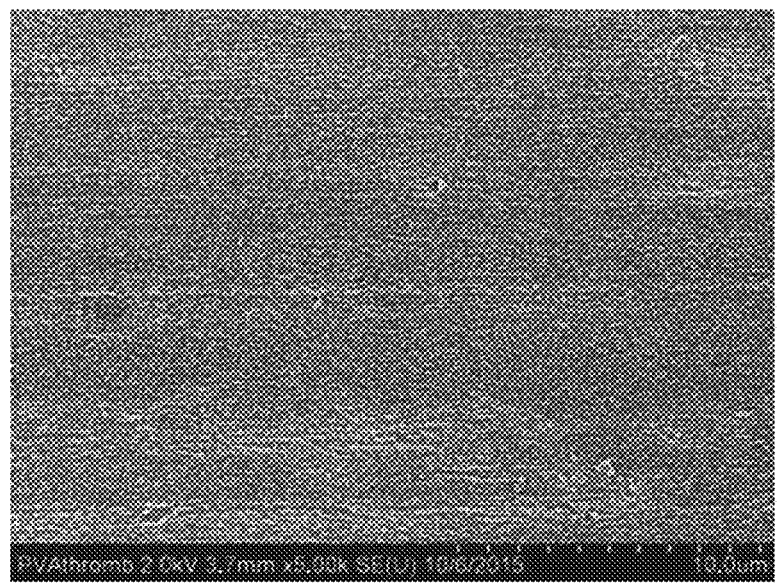
FIG. 8 is a SEM of a cross-section of the porous solid of FIG. 7.

The extruded samples have a horizontal chain orientation and alignment along the length of samples (in direction of extrusion), as supported by the SEM of a nanoporous material provided in FIG. 7. A polymeric chain orientation produced by the extrusion process. FIG. 8 is a SEM image of cross-section of the same material prepared according to Example 1A indicating pore sizes of 100 nm or less. For instance, in FIG. 8 it can be seen that there is a 1 μm scale bar subdivided into 10 segments of 100 nm each. Pores of 10 nm or more are visualizable at this resolution but none are visible. The micrograph has various large strands of polymer that indicate a certain degree of roughness at the microscopic scale but the surface below the strands is smooth and lacks open areas that indicate pores.

The results in strength, radiopacity, and qualitative observations on surface finish and symmetry of the samples are very good. The sample surfaces were substantially, but not entirely, free of imperfections. No severe lines, bumps or other imperfections were observed, a result obtained with extrusion that is superior to the same ingredients when used to make casted samples which contained severe parting lines. Extrusion processes were observed to be efficient and useful for creating tough, flexible, high tensile strength tubing with high aspect ratios that are not possible using conventional molds. Drawing processes that are similar to the extrusion may also be employed.

Example 1A describes a general process for extruding a porous solid. Surprisingly, the process was effective. A cold extrusion process was created, with the die being kept on the extrusion side in the bath at only 13° C. The polymer is hydrophilic and viscous at reduced temperatures. The cold extrusion was effective at making very strong materials with other good properties including flexibility, smoothness, lack of defects, and consistent pore sizes. A mixture of a polymer in a solvent, with PVA in water being used in Example 1A, was used to achieve the extrusion. And extruding into a solvent-removing environment, which was an alcohol bath in this example, contributed to the desirable properties. In general, it is useful to have a combination of one or more of: extrusion of a hydrophilic polymer in a solvent; a cold extrusion, and extrusion into a bath that quickly removes solvent from the extrudate. Further, additional solvent-removing and/or annealing processes provide further utility for making desirable porous solids.

The process of Example 1A produced a nanoporous solid. Requirements for a nanoporous material include high polymer concentrations of more than about 10% w/w in the polymer-solvent mixture with high levels of crosslinking. Artisans will immediately appreciate that all ranges and values between the explicitly stated bounds are contemplated, with, e.g., any of the following being available as an upper or lower limit: 10, 12, 15, 16, 17, 18, 19, 20, 25, 30, 35, 40, 45, 50, 55, 60, 70, 80, 90, 95, 99% w/w of the polymer in the total weight of the polymer-solvent mixture. The polymer is to be substantially solvated, meaning it is a true solution or at least half the polymer is dissolved and the rest is at least suspended. The solvation of the polymer contributes to the alignment of the polymer chains in an extrusion and to crosslinking among the polymers. Without being bound to a particular theory, it is likely that high concentration of the starting polymer-solvent mixture can help with this. And the probable chain alignment of the material as it passes through a die is thought to promote more intrapolymer versus interpolymer crosslinking. An extrudate or an otherwise formed mixture entering a desolvating environment, whether gas or liquid, is thought to further collapse pore structure before the densely concentrated polymer has completely crosslinked, thereby improving chain proximity and promoting additional crosslink density. Depositing the extruded or otherwise formed material directly into a solvent removing environment is helpful. Further solvent-removal can be continued to collapse the material until reaching a desired end point in structure and/or properties. An annealing process can further contribute to strength.

Frozen methods, on the other hand, rely on increased strengthening by forcing super-concentrated microregions to also achieve chain proximity and improve crosslink density, but retain a macro porosity due to the presence of ice crystals in the total gel structure. Desolvation creates forced super-concentrated microregions but these do not create macropores. In contrast, a pre-established gel prior to a dehydration or freezing is by nature of that process formed with macropores. Further, the work of the inventors indicates that such nanoporous solids have greater strength than macroporous materials.

Hydrogels can also be made by using a lower polymer concentration in the polymer-solvent mixture, generally less than 10% w/w of polymer in the polymer-solvent mixture. Artisans will immediately appreciate that all ranges and values between the explicitly stated bounds are contemplated, with, e.g., any of the following being available as an upper or lower limit: 2, 5, 7, 8, 9, 10% w/w of the polymer in the total weight of the polymer-solvent mixture. Further, or alternatively, the polymer-solvent mixture is not extruded into a solvent removing environment.

Microporous materials may be made with process conditions intermediate to nanoporous solids and hydrogels. One embodiment is to prepare a material using conditions comparable to making a nanoporous material but to stop solvent removal before solvent removal reaches a nanoporous solid structure.

Extrusion of hydrophilic polymers, including the PVA of Example 1A, in a solvent is helpful to make high strength materials. Use of a solvent in an extrusion starting material is, at the least, uncommon. Typically, an extrusion uses a solid material that has been heated to a flowable temperature and then extruded, and later cooled by a variety of methods. For instance, it is believed that an extrusion of a pure PVA is possible. But such an extrusion would lack the polymeric structure that is needed to make porous solids and would instead behave like a conventional plastic. According to a theory of operation, a pure PVA extrusion would lack the quality of hydrogen bonding that takes place in an aqueous ionic solvent state. A temperature suitable for preparing the PVA to be flowable in an extrusion would create a poorly cohesive material at the die head so that a continuous shape does not form. It was difficult to make extruded PVAs to form high aspect shapes, e.g., tubes, and to use them in an extrusion process. Viscosities of PVA and other hydrophilic polymers are high, and difficult to get into solution. It was observed that a narrow working band of temperature was particularly useful, e.g., 85-95° C. Below about 85° C., PVA failed to truly melt, and thus did not become completely amorphous for extrusion. Above about 95° C., losses to boiling and evaporation made the process ineffective. These temperature ranges could be offset by increasing pressure above atmospheric, but a pressurized system is challenging to use and to scale. The processes are usefully performed at a temperature below a boiling point of the polymer-solvent materials.

The cohesive strength of the flowing polymer-solvent mixture was weak when exiting the die. The use of a core to support the mixture at the die is useful to hold the shape at the die. This condition is in contrast to a typical core extrusion used as a coating process, e.g., for coating wires for a mobile telephone charger. A typical process that avoids use of a solvent or a significant solvent concentration has a relatively higher cohesive strength that it exits the die that is readily capable of holding a tube, and do not relying on active bonding such as the hydrogen bonding in hydrophilic polymers that form the solid material in a coherent shape as it moves out of the die.

Passing the formed polymer-solvent mixture into solvent removal environment was useful. In Example 1A, for instance, using a cold ethanol bath is atypical relative to a conventional extrusion. Most extrusions do not use bath temperatures at or below room temperature. Moreover, the use of a solvent removing bath is atypical relative to conventional processes the bath or other solvent removing environment helps solidify the extruded material sufficiently that it remains stable and concentric on the core, otherwise the melt would run into a tear drop shape. It would also be destroyed in the attempt to collect it at the end of the extrusion as it would still be molten. Conventional baths containing water would cause the PVA or similar hydrophilic polymer material to lose shape due to swelling, dissolution, or both. Example 1B is directed to molding processes that involve preparation of a polymer-solvent mixture that is formed in a mold and then processed into a solvent-removing environment. These processes do not have the advantages of alignment of chains observed in an extrusion. However, a suitably controlled temperature and solvent removal can yield materials with a high strength and controlled pore structure.

Figure 9:
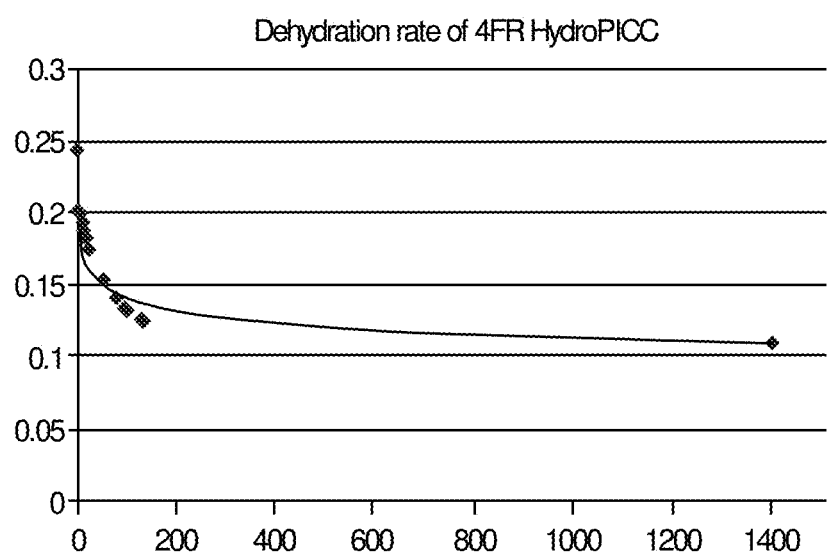
FIG. 9 is a plot of data for dehydration of a porous solid catheter, with the y-axis being weight and the x-axis being time in minutes.

Example 2 demonstrated the process was effective when it incorporated a radiopaque additive, with barium sulfate being the material used in this instance. In Example 3, the porous materials, when exposed to air at ambient conditions, lost water (FIG. 9) but retained their desirable properties and can be effectively transported/stored in sealed packages or in solution or left in ambient conditions for a reasonable storage duration or as may be needed after being unpackaged by a user for an end-use. Example 4, demonstrates strength (modulus and ultimate break) increased as the hydrophilic polymer (PVA) molecular weight was increased from 140 k to 190k (Table 3). Bismuth subcarbonate was used as a radiopaque agent. In the same Example, an increase in a concentration of the polymer in the polymer mixture used for extrusion showed an increase in strength for the highest concentration relative to the lower concentration (Table 5 and FIGS. 10-11).

The porous solids are highly lubricious and can be used in a hydrated state and can be conveniently bonded to other materials. In the case of a catheter, for instance, extensions, luer locks, suture wings, and the like are useful. Example 5 demonstrates that conventional processes are effective in bonding other materials to the porous materials. Examples 6 and 7 showed that the porous solids were suitable for radiopaque medical devices and had good burst strengths in pressure tests. Contact drop testing (Example 8) showed that various porous solids were hydrophilic (PVA tested). SEM images (FIGS. 15A-15B, Example 8) are images of a nanoporous solid. Example 9 is directed to a nanoporous solid (FIGS. 16A-16D).

Observations of the tested samples indicated that, without being limited to a particular theory, crosslinks within the material provided by a first hydrophilic polymer (PVA) were increased by interaction with the chains of a second polymer (PAA or PEG) until the second polymer began to form domains with itself in the material. This is likely due to the ability to incorporate higher molecular weight species of the second polymer (PAA or PEG) providing additional material strength. The results generally indicate that copolymer extrusion is useful in ranges of the second polymer from 0.1% to 10% w/w or no more than 10% w/w of the first polymer, with no more than 5% w/w also being useful. Artisans will immediately appreciate that all ranges and values between the explicitly stated bounds are contemplated, with, e.g., any of the following being available as an upper or lower limit: 0.1, 0.2, 0.4, 0.5, 0.8, 1, 2, 3, 4, 5, 6, 8, 10% w/w.

Figure 17A:
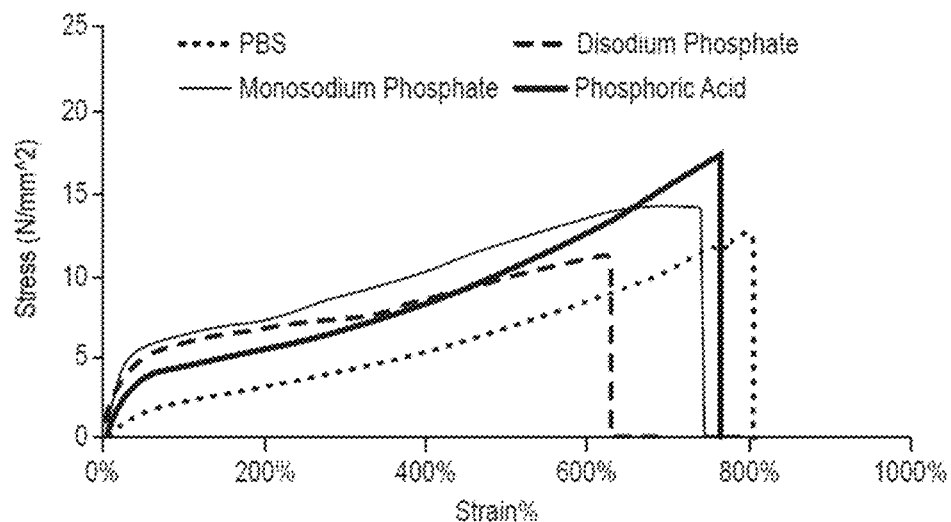
FIGS. 17A-17B are plots of tensile test data for samples generated as described in Example 10.
Figure 17B:
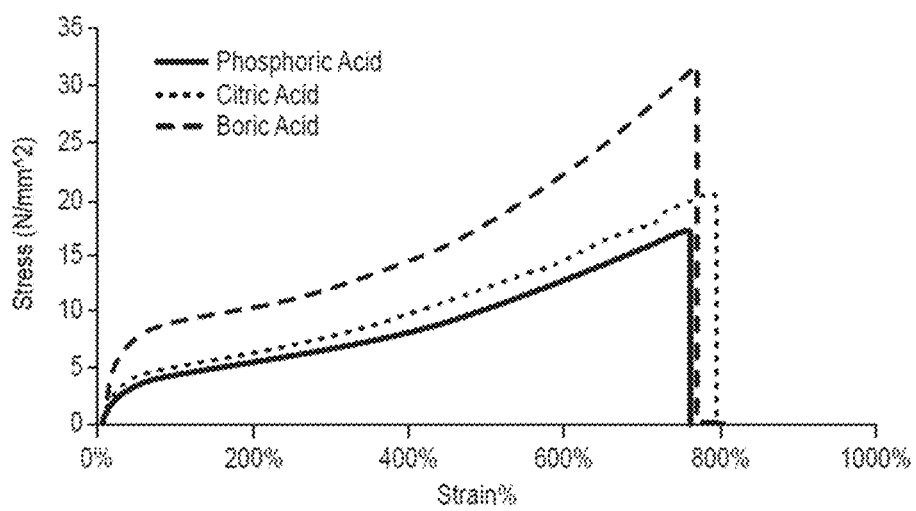

The effects of various salts on properties of the porous solids were assessed as described in Example 10 (FIGS. 17A-17B). Salts were useful to manipulate the strength of the materials. Without being limited to a particular theory, it is likely the salts were part of the physical crosslinking, in effect acting as small molecular weight crosslinkers between the polymer chains. Monosodium phosphate resulted in the highest Young's Modulus and phosphoric acid produced the highest tensile. Boric acid increased both Young's Modulus and maximum tensile stress, whereas citric acid and phosphoric acid were comparable to each other. Boric acid forms high strength crosslinks but is not a covalent crosslinker.

Figures 12A, 12B, 12C, 12D, 12E, 12F:
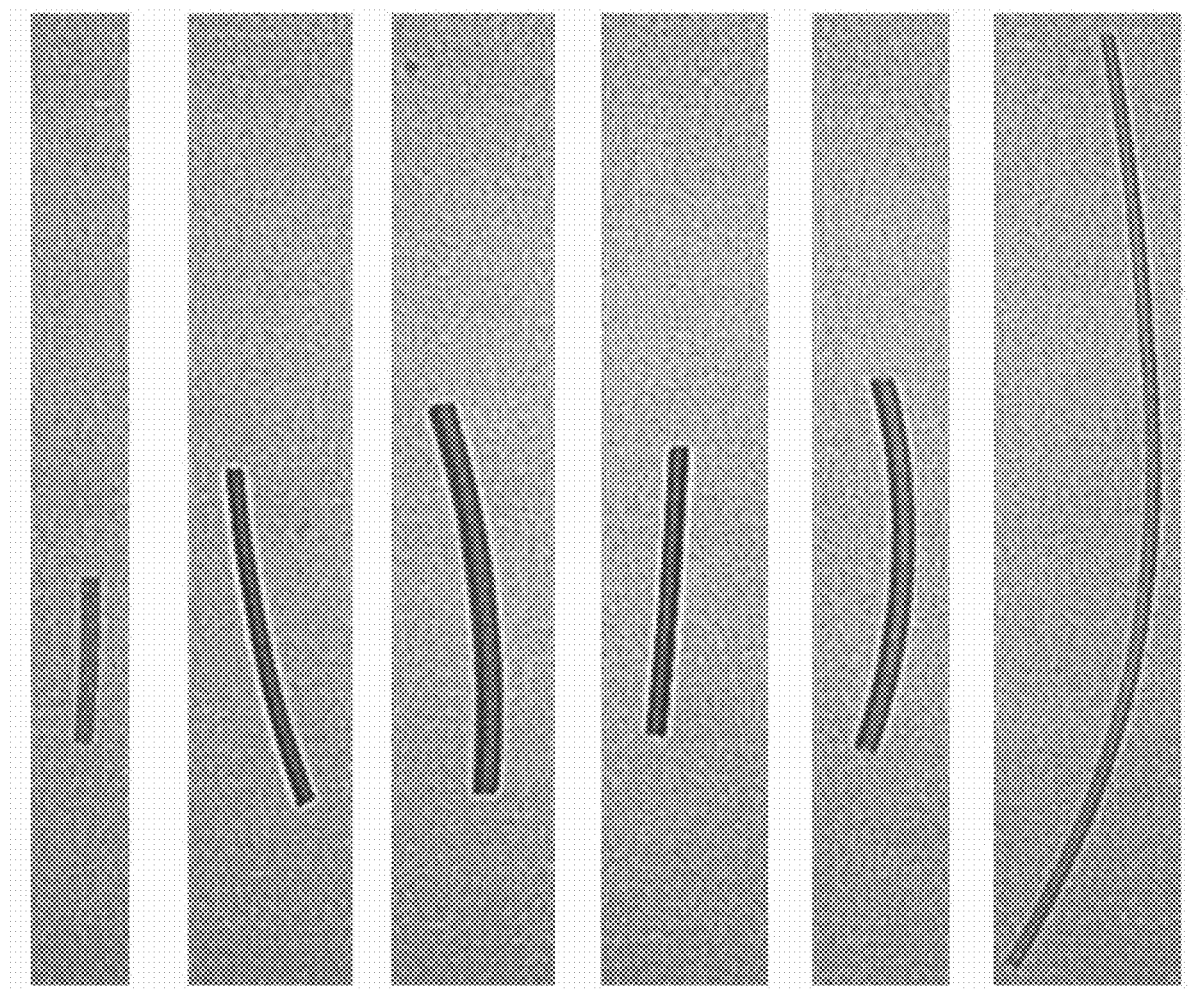
FIGS. 12A-12F are photographs of porous solids that incorporate a radiopaque agent: 12A, control (Bard POWERPICC), 12B, 5.7% bismuth subcarbonate by weight, not annealed, 12C, 12.1% bismuth subcarbonate by weight, not annealed, 12D, 12.1% bismuth subcarbonate by weight, annealed, 12E, 5.7% bismuth subcarbonate by weight, annealed, 12F, 4.2% bismuth subcarbonate by weight.
Figure 18A:
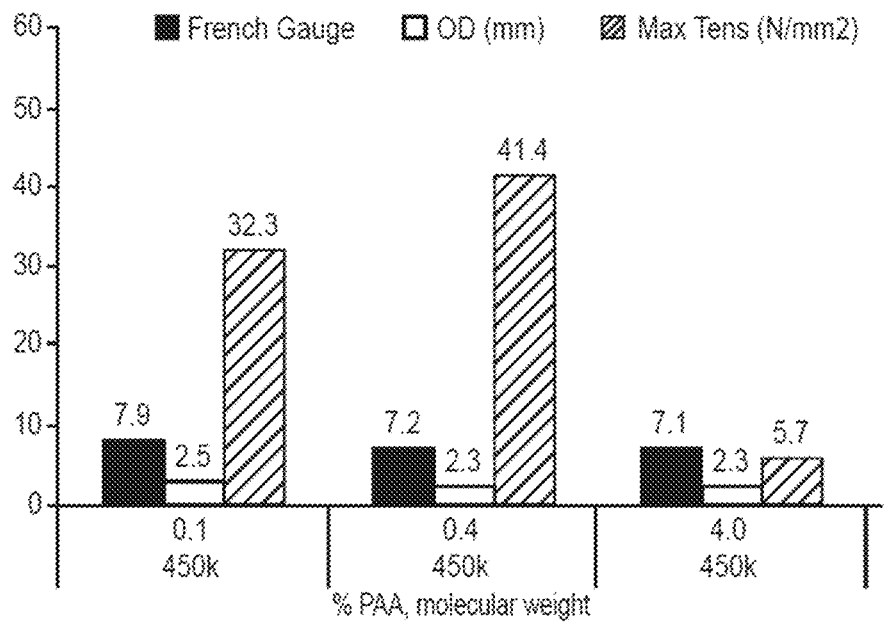
FIGS. 18A-18B are plots of tensile data for various blends of polymers described in Example 11, with data being shown in $N/mm^2$.

Further tensile tests were performed for coextrudates with a concentration of a first hydrophilic polymer and a relatively lower concentration of a second hydrophilic partner, Example 11. FIG. 18A depicts tensile test for a PVA mixture having a low concentration of 450 kDa PAA (0.1, 0.4, or 4.0% w/w PAA, 16% w/w PVA, percentages are polymer w/w concentration in solvent). The 0.1-0.4% w/w PAA concentrations had a higher strength and support the conclusion described for Examples 9 and 10, above. A higher molecular weight (MW) PAA (3 million Da) was tested (FIG. 18B) but generally had only about half the strength of the lower MW PAA. The decrease in tensile strength with increased PAA molecular weight may be due to decreased bonding and/or tangling interactions between PVA and PAA due to the longer 3 million MW chains. No significant differences in strength were observed when three different MWs of PEGs were blended with PVA (8 k, 20 k, 35 k PEGs, FIGS. 19 and 20A-20C, Example 12). Porous plastics made of PVA without a radiopaque agent were superior to control catheters in regards to non-thrombogenicity (Example 13, FIGS. 21A-12B).

Embodiments for polymer blends include at least one first hydrophilic polymer and at least one second hydrophilic polymer in a solvent that is extruded as described herein. Examples include combinations of one or more of PVA, PAA, PEG, PVP, polyalkylene glycols, a hydrophilic polymer, and combinations thereof. Examples of concentrations include the at least one second hydrophilic polymer being present at 1 parts to 10,000 parts of the first hydrophilic polymer. Artisans will immediately appreciate that all ranges and values between the explicitly stated bounds are contemplated, with, e.g., any of the following being available as an upper or lower limit: 1, 2, 10, 100, 1000, 1500, 2000, 2500, 3000, 4000, 5000, 6000, 7000, 8000, 9000, 10000 parts. Examples of concentrations of polymers in a polymer-solvent mixture include a first polymer present at a first concentration and one or more further polymers present at a second concentration, with the first polymer concentration and the further polymer concentration being independently selected from 0.1-99%, e.g., 0.1, 0.2, 0.3, 0.4, 0.5, 0.6, 1, 2, 3, 4, 5, 6, 7, 8, 9, 10, 11, 12, 13, 14, 15, 16, 17, 18, 19, 20, 25, 30, 33, 35, 40, 45, 50 55, 60, 65, 70, 75, 80, 85, 90, 95% w/w. Further, non-hydrophilic polymers and/or non-hydrophilic blocks in block polymers, may be present, with concentrations of such polymers and/or such blocks generally being less than about 10% w/w, e.g., 0.1, 0.2, 1, 2, 3, 4, 5, 6, 7, 8, 9, 10% w/w.

Example 14 describes bulk incorporation of water soluble polymers into a porous solid. A porous solid with RO agent was extruded as in Example 1A, desolvated by drying, soaked in an aqueous solution of polyacrylic acid (PAA), and allowed to rehydrate for 24 hours at which time it was at EWC in the aqueous solution. The sample was annealed, rinsed, and placed into deionized water. Samples conditioned to incorporate water soluble polymers have been observed to undergo many cycles of hydration and dehydration without observable effects (data not shown).

Figures 22A, 22B, 22C:
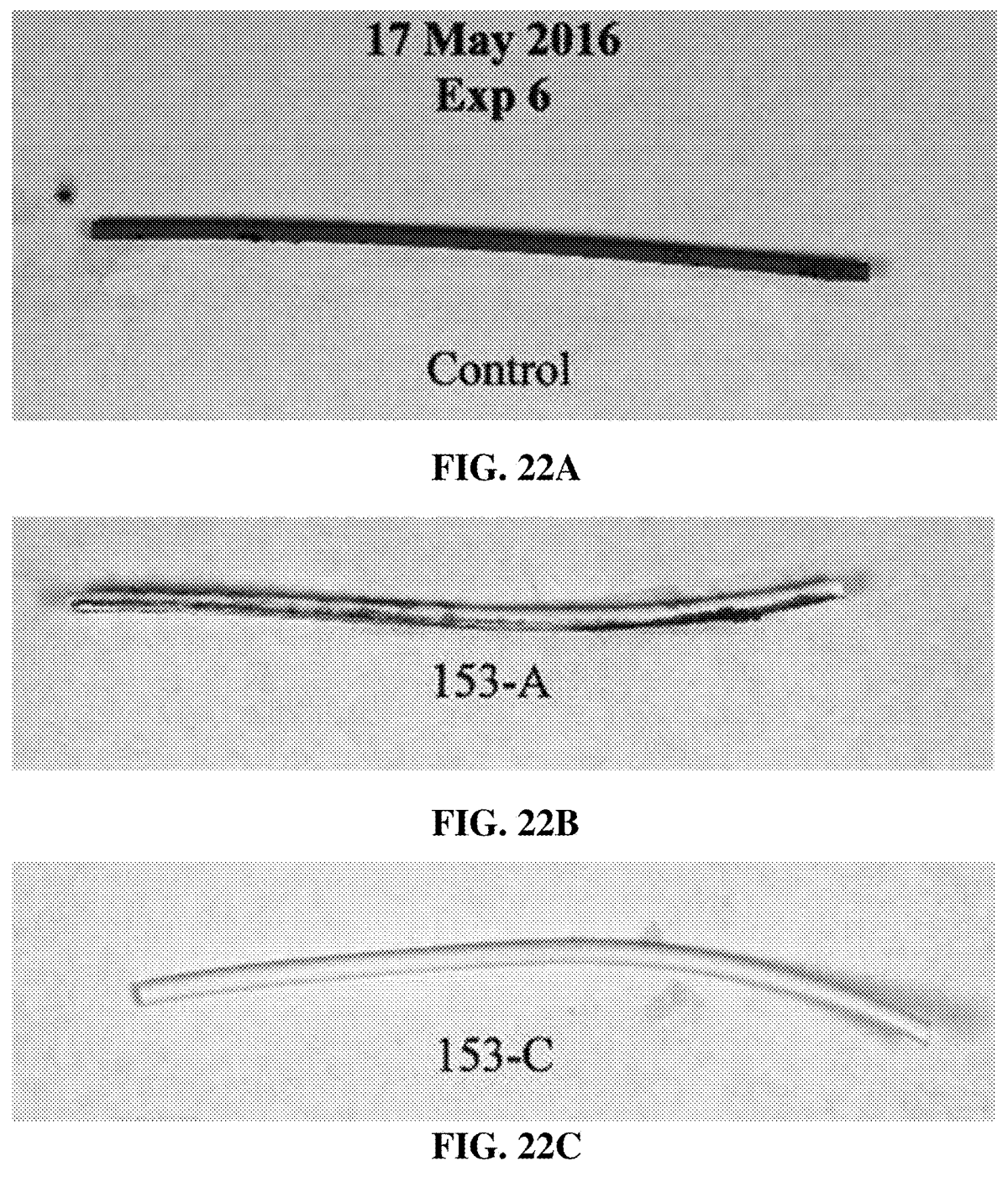

Samples made with this process were tested for thrombogenicity, for example, as described in Example 15. The porous solid tubing (PVA) with the bulk incorporated water-soluble polymer (PAA) showed an 89 percent reduction in platelet attachment compared to the standard polyurethane control. Also notable is the lower standard deviation assessed for the overall results, showing improved consistency and demonstrating durability of the bulk incorporated polymer. Without being bound to a particular theory, it appears that the porous solid tubing without the bulk incorporated PAA (sample 153-A) had higher gamma counts due to the radiopaque agent. The significant reduction in thrombogenicity in the porous solid PVA tubing including the RO agent were prepared with the bulk-incorporated surface polymer (PAA) (sample 153-C) supports durable modification at the surface via the bulk incorporation process described in Example 14. FIG. 22 is an example photograph of a tested sample of Example 15.

Figure 23:
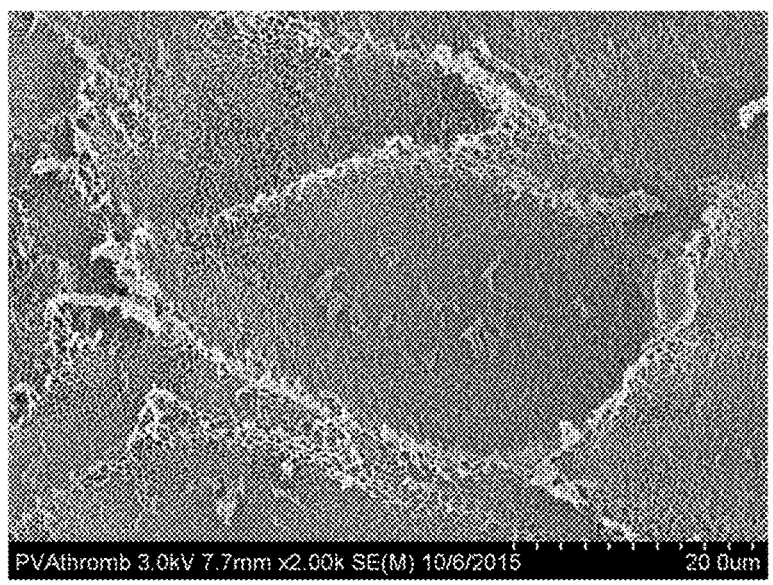
FIG. 23 is a scanning electron microscopy (SEM) micrograph of a surface of the porous solid of PVA with RO agent of FIG. 7 at 2000× magnification.
Figure 24A:
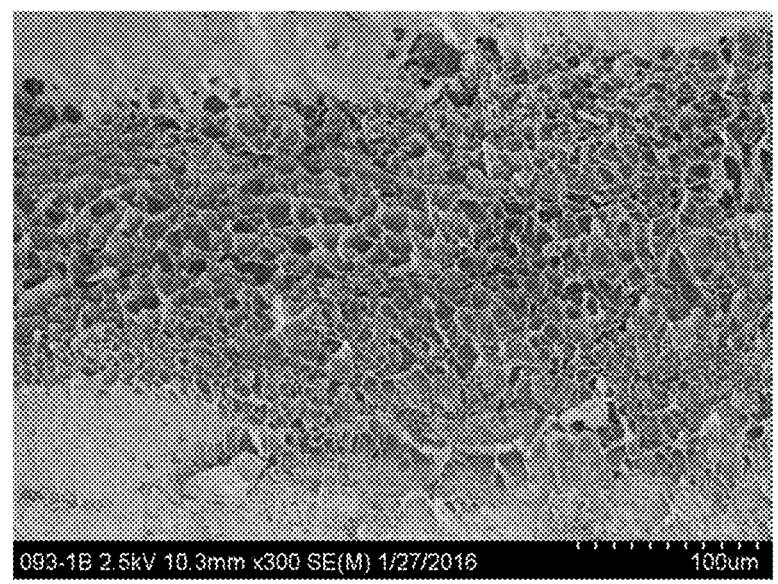
FIGS. 24A-24B are SEM micrographs of representative samples containing a porous solid of PVA with RO agent, with the solid including bulk incorporated surface bound water-soluble polymer at 300× magnification (24A) or 2500× magnification (24B).
Figure 24B:
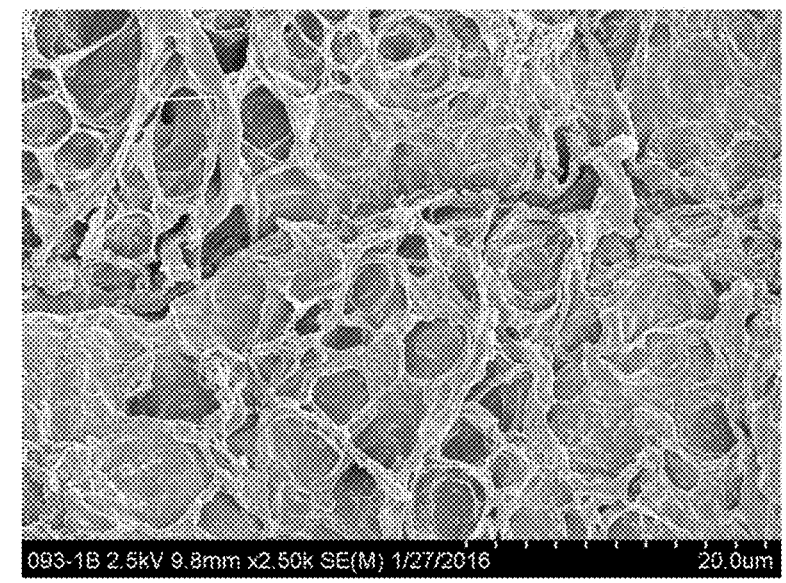

FIGS. 23 and 24 (Example 16) are SEM images of surfaces of a porous solid (PVA) made with an RO agent that is without (FIG. 24) or with (FIGS. 24A-24B) a bulk incorporated polymer. FIG. 23 is a higher magnification image of the sample shown in FIG. 7. The conditioning with the water-soluble polymer resulted in surfaces with different morphologies.

Figure 25A:
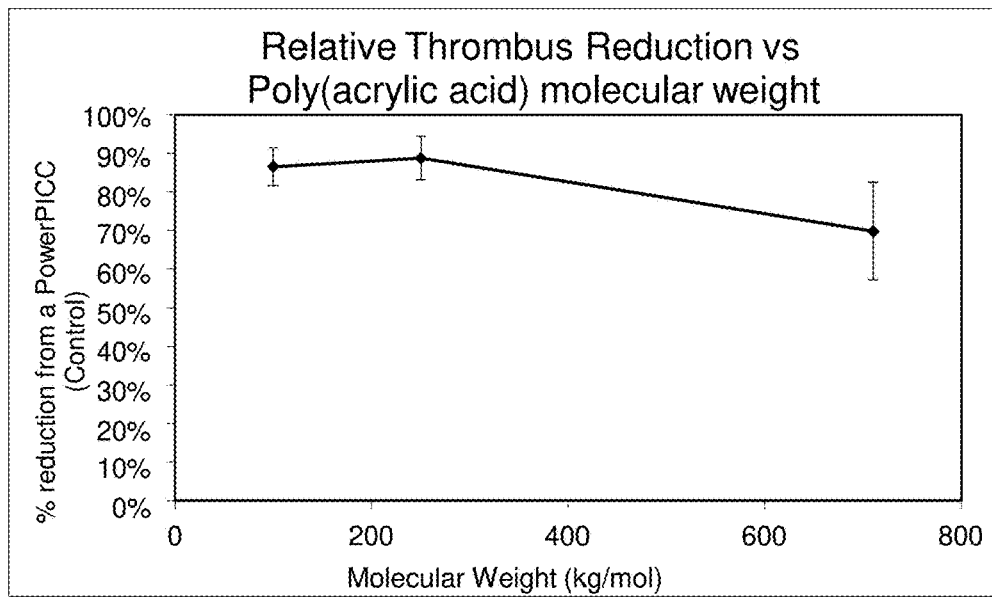
FIG. 25A is a plot of results of Example 17 depicting thrombus accumulation on samples of porous tubes compared to a conventional catheter control, with the porous solids having bulk incorporated surface bound water-soluble polymers of various molecular weight.
Figure 25B:
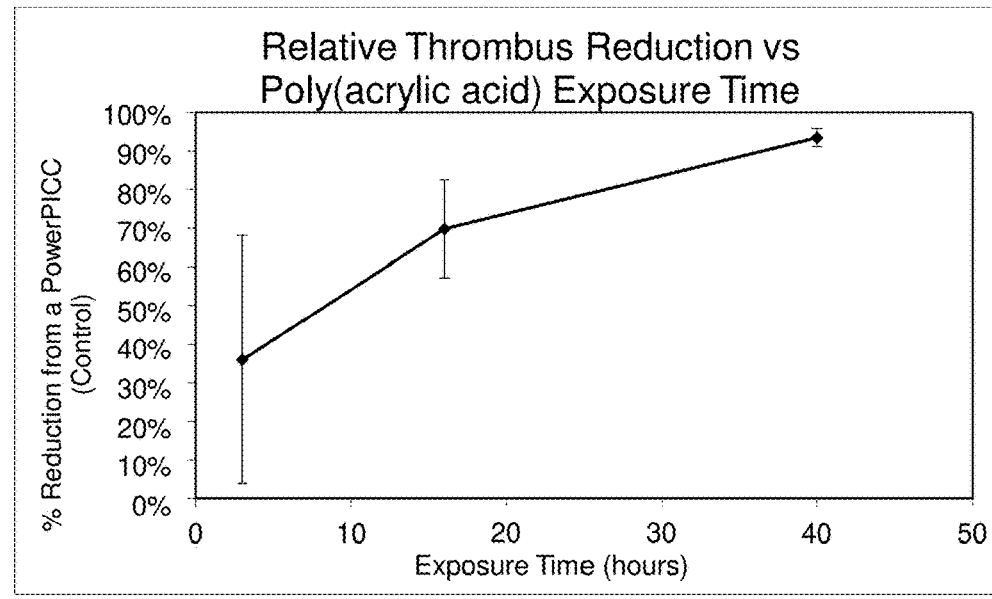
FIG. 25B is a plot of results of Example 18 depicting thrombus accumulation on samples of porous solids having bulk incorporated surface bound water-soluble polymer, with accumulation being shown over time.
Figure 25C:
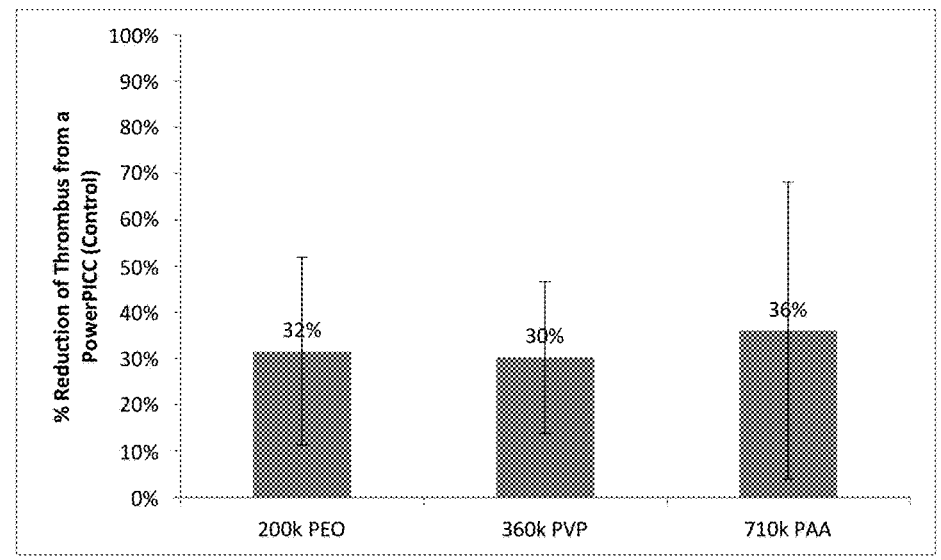
FIG. 25C is a plot of results of Example 19 depicting thrombus accumulation on samples of porous solids having bulk incorporated surface bound water-soluble polymer of various molecular weights and backbone compositions as compared to a conventional catheter control.

Example 17 (FIG. 25A) describes testing the non-thrombogenicity of porous solids (PVA) with bulk incorporated water-soluble polymer (PAA) of varying molecular weights (100-710 KDa). No significant difference was observed. The improved non-thrombogenic properties of the porous solids with a bulk incorporated water-soluble polymer were measured at several time points, as per Example 18. It was observed that the improvement relative to the control increased as the length of the test was increased (FIG. 25B). Various bulk incorporated water-soluble polymers were tested in Example 19. It was observed (FIG. 25C) that all of the incorporated water-soluble polymers were effective in reducing thrombogenicity.

Porous solids that bulk incorporate various water-soluble polymers were prepared and visualized (FIGS. 26-32), for example as described in Example 20. SEM evaluations showed successful surface modification through the presence of different water soluble hydrophilic polymers using bulk incorporation techniques.

Example 21 describes bulk incorporation of another water soluble polymer, poly(sulfobetaine methacrylate) (pSBMA) into a porous solid tube. Fourier transform infrared spectroscopy (FTIR) measurements indicated successful incorporation of the pSBMA.

Example 22 describes a test to show that water soluble polymers were incorporated into a porous solid such that there was little loss of water soluble polymer upon exposure to physiological solution. Physiological saline was flowed across the sample for 24 hours while the sample was exposed directly to the mechanical pump head equaling 500,000 compressions at a flow rate of 11 mL/s with about 24% w/w loss of the bulk incorporated polymer. Embodiments include porous matrices conditioned with water soluble polymers that lose no more than 20-90% w/w of the water-soluble polymer under comparable conditions; Artisans will immediately appreciate that all ranges and values between the explicitly stated bounds are contemplated, e.g., 20, 25, 30, 33, 40, 50, 60, 70, 80, 90% w/w. This test is indicative of a durable incorporation of the bulk polymer. It is evident that water soluble polymers that were merely adsorbed would not show this high degree of durability. The porous matrix was hydrophilic and the incorporated polymers were not processed in conditions that would promote formation of a coating with covalent or other crosslinks.

Figure 35A:
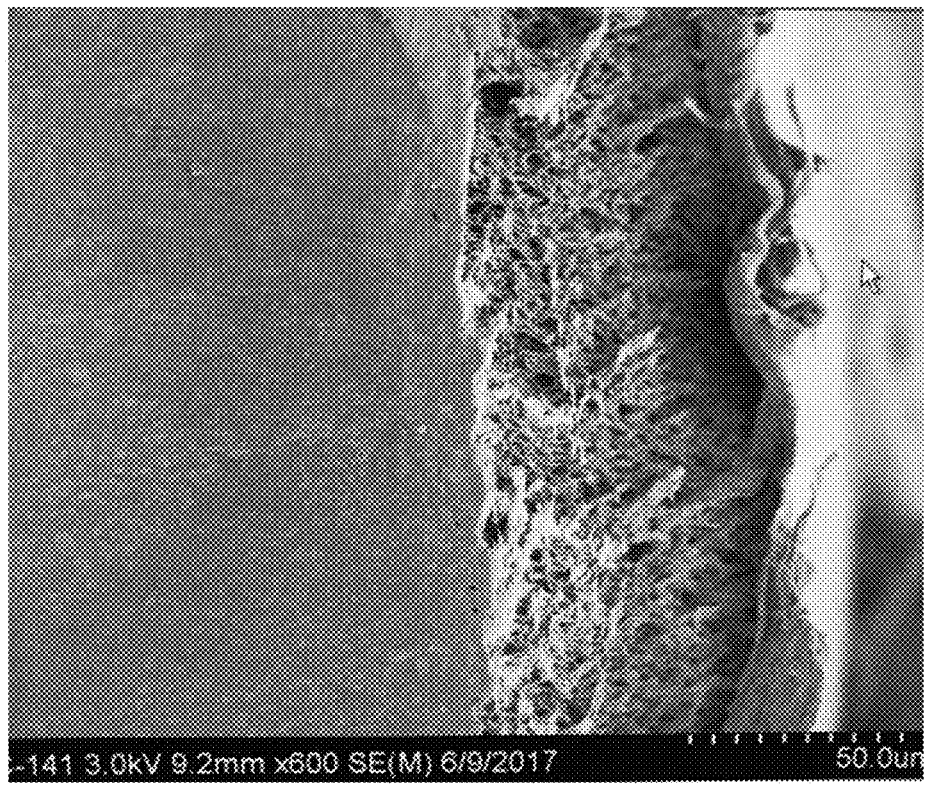
FIGS. 35A-35B are SEM micrographs of a cross section of a porous solid with (35A) or without (35B) and bulk incorporated water-soluble polymer as per Example 23.
Figure 35B:
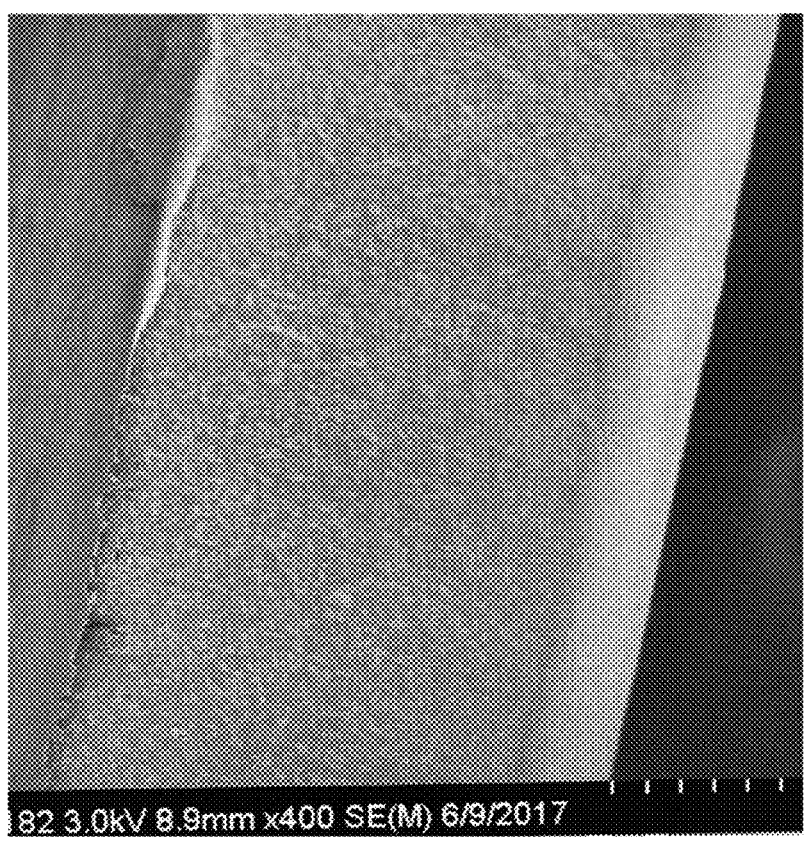

Samples were exposed to water soluble polymer with (FIG. 35A) or without (FIG. 35B) being desolvated prior to exposure to the mixture with the polymer (Example 23). The morphologies are different, with the sample made without bulk incorporated polymers being smooth, in contrast to the many features visible on the conditioned sample, which is consistent with other images taken of samples with a bulk incorporation. FIG. 35A shows a cross sectional view of the surface of the sample that was a PVA tube that had been exposed to the PAA solution after desolvation. The threads along the surface are indicative of a PAA bulk incorporated into the solid porous PVA tube, similar to results shown in Example 20. In FIG. 35A, an outer zone is visible that extends from the surface to a distance of about 10-30 μm into the porous matrix; this zone appears solid in the micrograph and is an area where the bulk incorporated polymers apparently completely fill the pores. FIG. 35B shows PAA is unable to be bulk incorporated after a PVA tube has been annealed but not desolvated when exposed to the conditioning mixture; as apparent in FIG. 35B, no threads are observed on the surface. This test confirms the presence of a water-soluble polymer (PAA) at the surface using bulk incorporation techniques described. Even though one set of samples (FIG. 35B) was made as a porous hydrophilic matrix that was annealed, exposed to water soluble polymers, and then annealed again, the samples did not have the morphology that is typical of morphologies seen with bulk incorporation, e.g., as in FIG. 35A. Therefore, to make a material with bulk incorporated polymers, it is not enough to merely coat or otherwise expose the samples to water soluble polymers and then have an annealing step or the like.

Example 24 presents physical properties for samples with and without bulk incorporated polymers. The maximum load, Young's modulus, tensile strength, and elongation were significantly different for samples with water soluble polymer bulk incorporation as compared to non-conditioned samples. Without being bound to a particular theory, it appears that the bulk incorporated polymers interpenetrated pores of the porous solid matrix and prevented their collapse during subsequent annealing. As a result, the materials with bulk incorporated polymer had less tensile strength, less modulus, and were more subject to elongation. Embodiments include materials with physical properties altered as a result of conditioning with water soluble polymers. In fact, these physical properties were observed to decrease, which is in opposition to typical processes of coating or other surface alterations wherein the changes have minimal impact on such physical properties or are intended to improve them.

The bulk incorporated materials may present a monolayer at the surface. The term monolayer means a layer that is a single molecule thick. The monolayer does not rely on cohesion between the molecules of the monolayer to remain stably present at the surface. At least one water soluble polymer forms the monolayer. In contrast, even a thin polymer coating that is cross-linked to itself has a thickness corresponding to the thickness of the network formed by the cross-linked polymers. For example, it may be possible to create a cross-linked PVA coating on a surface but such a coating relies on interconnections between molecules of the PVA and necessarily forms a crosslinked network. Accordingly, embodiments include a water-soluble polymer present on a surface of a porous solid without covalent bonding to the surface and without the polymer being part of a network.

The bulk incorporated polymers are durably incorporated. In contrast, a layer of water soluble materials merely adsorbed to an underlying material, e.g., applied by dip coating or spraying, can be essentially removed from a hydrophilic substrate in most or all circumstances meaning at least 90% w/w of the materials can be separated from the underlying material in aqueous solution, e.g., 90° C. for 24 hours in physiological saline. Covalently bonded materials will not be removed under these conditions and some physically crosslinked networks of water soluble polymers might not be removed but such networks are not preferable compared to a bulk incorporated polymer; for instance, they would likely be more thrombogenic or less durable. Covalent bonding involves use of chemically reactive moieties that can be avoided by bulk incorporation processes.

Processing Systems and Parameters to Make Porous Materials

Processes are provided herein to create biocompatible porous solids such as microporous or nanoporous solid materials that possess low protein adsorption properties and provide a basis for non-biofouling devices. Modification of starting polymer concentration, molecular weight, solvent removal, forming processes, and hardening/annealing processes may be utilized to provide surface properties with reduced protein adsorption and other properties. Some embodiments include creation of various continuous shapes through extrusion of a polymeric mixture. The mixture may be further hardened and annealed. These processes may be used to create a tough and highly lubricious material. Embodiments include polymeric mixtures extruded into shapes possessing single or multiple lumens, of varied diameters and wall thickness.

An embodiment of a process for making a nanoporous solid material comprises heating a mixture that comprises a polymer and a solvent (a polymeric mixture), extruding the mixture into a solvent-removing environment, and removing the solvent from the crosslinked matrix until a nanoporous solid material is formed. One or more of these actions may be combined, depending on the process. Further, cooling the mixture as it passes out of the die is useful. Without being bound to a specific theory of operation, it appears that crosslinking the polymer during passage through the die initially forms a porous matrix that is not a true nanoporous solid material because, although it has spaces between polymer strands, it does not have a pore-structure. As the solvent is removed under appropriate conditions, the crosslinked structure becomes a nanoporous solid. The crosslinking starts when the polymeric mixture is extruded through a die, and as the mixture is cooled. The crosslinking may continue while the solvent is removed. The transition to form the nanoporous material takes place as the solvent is removed and, in general, is believed to be completed or essentially completed (meaning 90% or more) at this stage. The resultant material may be further processed by annealing with or without a presence of further solvents, or plasticizers. This process, and the other extrusion or other formation processes and/or materials set forth herein, including bulk incorporation processes, may be free of one or more of: covalent crosslinking agents, agents that promote covalent crosslinks, radiation that crosslinks polymer chains, freezing, thawing, freeze-thaw cycles, more than one freeze-thaw cycle, ice-crystal formation, foaming agents, surfactants, hydrophobic polymers, hydrophobic polymer segments, reinforcing materials, wires, braids, non-porous solids, and fibers.

The porous materials may be made by an extrusion process comprises passing a polymeric mixture through a die into a cooling environment. The cooling environment may further be a solvent-removing environment. It is a dehydrating environment when the solvent is water. The die may have a core that passes through it so that the polymeric mixture may be formed around the core. Further solvent-removal environments and/or annealing environments may be used.

The extrusion process for a polymer-solvent mixture may be performed as a cold extrusion. The term cold extrusion refers to a process that involves passing a polymer-solvent mixture through a die and does not require heating the polymer-solvent mixture above its boiling point during the entire process of preparing the polymer-solvent mixture and extruding it. Accordingly, in a cold extrusion, the die head is kept below a boiling point of the polymer-solvent mixture. Although many solvents may be used, water is often a useful solvent in which case the die head is kept at 100° C. or less, although colder temperatures may be useful, as discussed above.

The term polymeric mixture refers to a polymer that is in solution, dissolved, or suspended in a solvent. A solvent may be, e.g., water, aqueous solution, or an organic solvent. Heating the polymeric mixture may comprise heating the mixture to a temperature above the melting point of the polymer. In general, the solution transitions from a cloudy to a clear state when it reaches the melt point. An aqueous solution contains water, for instance from 10-100% (w/w or v/v) of the liquid being water; Artisans will immediately appreciate that all ranges and values between the explicitly stated bounds are contemplated, e.g., 10, 20, 30, 40, 50 60, 70, 80, or 90% or at least one of the same.

Extrusion is a useful process for forming the materials. Other forming processes may be used, for example, molding, casting, or thermal forming polymer-solvent mixtures. In general, a polymer-solvent mixture is prepared without boiling and formed into a shape that is exposed to solvent-removal conditions that are controlled to make a nanoporous or microporous material using the guidance provided herein.

An annealing process may be included. Hydrogels that are not microporous or nanoporous materials can also be made.

The heated polymeric mixture may be molded or otherwise formed as it is cooled or molded/formed and immediately cooled. Formed is a broad term that refers to passing the material from an amorphous melted state into an end-user product or an intermediate shape for further processing. Forming encompasses casting, layering, coating, injection molding, drawing, and extrusion. The forming can be done using an injection molding set up, where the mold consists of a material with thermoconductive properties allowing it to be heated easily to enhance the flow of the injected polymeric mixture, and to be cooled rapidly in a cooling environment. In other embodiments, the molding process can be accomplished by extrusion of the polymeric mixture through a die to form continuous material.

Cooling the polymeric mixture may comprise, e.g., cooling an extruded material, as in the case of passing the polymeric material through a die. An embodiment for cooling is a liquid bath at a temperature at least 20° C. cooler than the polymeric mixture boiling point or alternatively below the polymeric mixture Tm, e.g., 20, 30, 40, 50, 60, 70, 80, 90, 100, 110° C. below the boiling point or polymeric Tm, or alternatively the bath or other environment being at a temperature from −50 to 30° C.; Artisans will immediately appreciate that all ranges and values between the explicitly stated bounds are contemplated, with, e.g., any of the following being available as an upper or lower limit: −50, −45, −25, −20, −10, −5, −4, 0, 15, 20, 25, 30° C. The cooling may be performed in a solvent removing environment. Freezing temperatures may be avoided. Without being bound to a particular theory of operation, the polymer chains are cooled to the point of promoting intermolecular hydrogen binding and immobilizing chain movement. This may occur at temperatures as high as 30° C., or higher if time is allowed. The bath may be aqueous, and, by adjustment with salt or other osmotic agents, may be provided at an osmotic value to perform solvent removal on aqueous materials that are at a relatively lower osmotic value through osmotic pressure and diffusion. The bath may also be other solvents that freeze at temperatures lower than water, so that temperatures below 0° C. may be used without freezing the solvent or materials. In the event that hydrophilic copolymers are used in conjunction with PVA, for instance, temperatures higher than 20° C. may be used as crosslinking and chain immobilization will occur at much higher temperatures.

A solvent-removing environment refers to an environment that significantly accelerates removal of a solvent as compared to drying at ambient conditions. Such an environment may be non-heating, meaning it is not above ambient temperature, e.g., not above 20° C. Such an environment may be a vacuum, e.g., a vacuum chamber, a salt bath, or a bath that removes the solvent in the polymeric mixture. For instance, an aqueous polymeric mixture may be introduced into an ethanol bath, with the ethanol replacing the water. The ethanol may subsequently be removed. A salt bath may be, e.g., a high salt concentration bath (1 M to 6 M). A time of processing in a solvent-removing environment and/or a cooling process may be independently chosen to be from 1 to 240 hours; Artisans will immediately appreciate that all ranges and values between the explicitly stated bounds are contemplated, with, e.g., any of the following being available as an upper or lower limit: 1, 2, 5, 10, 24 hours, 1, 2, 5, 7, 10 days. Salts may be salts that dissociate to make single, double, or triply charged ions.

One or a plurality of solvent-removing environments may be used, or one environment may be adjusted with respect to temperature. Thus, a cooling bath may be used followed by solvent removal in an oven or vacuum oven. A washing step may be performed before or after cooling or solvent removal, e.g., by soaking in a series of solvents of varying concentrations, varying salt solutions, varying proportions of ethanol or other solvents.

An embodiment is an extruded material that has been through a solvent-removal process comprising exposure to a salt bath, the material being is soaked in a series of diH20 baths (new baths or exchanged) for a period of time (e.g., 2-48 hours, 4-24 hours) to remove excess salt from the cast material or end-user device. The material is removed from the wash step and dehydrated to remove excess water. Dehydration can be done using, e.g., temperatures ranging from 20-60° C. Dehydration is generally performed at 37° C. for greater than 24 hours.

An embodiment is a polymeric mixture that has been extruded or otherwise formed that is then exposed to a high salt concentration bath (1 M to 6 M) for an inversely correlated period of time; high salt reduces the time required for soaking; for instance, it is soaked for 16-24 hours in a 6 M solution of NaCl. After soaking, the material is rinsed free of salt solution. The material is now toughened and can be removed from any mold pieces carried over from the initial formation. Alternatively, after a salt or other bath, the material is soaked in water baths and dehydrated to remove excess water. Dehydration can be done using temps ranging from 20-60° C. Dehydration may be performed at 37° C. for greater than 4 hours, greater than 24 hours, or in a range from 4 to 150 hours; Artisans will immediately appreciate that all ranges and values between the explicitly stated bounds are contemplated, with, e.g., any of the following being available as an upper or lower limit: 4, 6, 8, 10, 12, 16, 24, 48, 72, 96, 120, 144, 150 hours. For instance, dehydration at 40° C. for 6-24 hours has been observed to be useful.

In another embodiment, NaCl is incorporated into the starting polymeric solution at concentrations ranging from 0.1 to 3 M of the final polymeric mixture volume. A polymer is dissolved in a heated solution under agitation, then brought above its melt point. To this solution, dry NaCl is added slowly under agitation until completely dissolved. The slightly hazy solution is then drawn into a feed for the purpose of creating a shape, either through injection molding, casting, extrusion and/or drawing. A quench is performed at the end of each process to rapidly reduce the temperature and form a solid material. In this embodiment, no additional salt soak is required. After material hardening, if necessary, the material is removed from any molding process parts and rinsed in water to remove salt and dehydrated.

The term annealing, as used in the context of a semi-crystalline polymer or a solid porous material refers to a heat treatment at an annealing temperature comparable to the melting temperature of the polymer or the polymers in the relevant material. This temperature is usually less than and is within about 0-15% of the melting temperature on an absolute temperature scale. Plasticizers or other additive materials may affect the melting temperature, usually by depressing it. For a pure PVA, for instance, the annealing temperature will be within about 10% of the melting point of the PVA; with other materials present, the annealing temperature will typically be lower. A theory of operation is that the annealing is a process that is a relaxation of stress combined with increase in the size of crystalline regions in the material being annealed. Unlike metals, annealing increases the strength of the annealed material. Annealing may be performed in one or more of: in air or in a gas or in an absence of oxygen or an absence of water, e.g., in nitrogen, in vacuum nitrogen, under argon, with oxygen scavengers, and so forth. For example, experiments have been made with annealing dehydrated PVA nanoporous materials. Annealing is utilized to increase crystallinity in the PVA network, further reducing pore sizes of the PVA network and to reduce adsorption properties of the final gel surface. Annealing can be done at temperatures ranging from, e.g., 100-200° C.; in a preferred embodiment, this step is performed submerging the dehydrated gel into a bath of mineral oil. Bulk incorporation of a polymer into a porous solid may also include an annealing process as already described above for a porous solid. Annealing may be performed after exposure of the desolvated porous solid to the mixture that has the polymers that are to be bulk incorporated. The Tg of the material may be raised or lowered dependent on the residual solvent content and/or presence of the bulk incorporated second hydrophilic polymer. As already described, the annealing process conditions may thus be adapted as to depend on temperature, time, ramp rate, and cooling rates of the substrate.

Annealing may be performed in a gas or a liquid at ambient, elevated, or low (vacuum) pressure. The liquid may be a low molecular weight polymer (up to 2000 Da) or other material (e.g., mineral oil). Examples of low molecular weight polymers are: silicone oils, glycerin, polyols, and polyethylene glycols of less than 500 Da. A useful embodiment is annealing in a bath of glycerin at, e.g., 140° C. for 1-3 hours; glycerin acts to further reduce fouling properties of the gel through interaction and neutralization of the free hydroxyl end groups of the PVA network. The annealed nanoporous material is allowed to cool, removed from the annealing bath and rinsed free of bath medium using a series of extended soaks. The product is then dehydrated to prepare for terminal sterilization.

Various types of dies may be used, e.g., longitudinal, angular, transverse and spiral extrusion heads, as well as single-polymer extrusion heads used for extruding a single polymer and multi layers extrusion heads used for simultaneous extrusion of a plurality of polymer layers or other layers. Continuous operation heads may be used, as well as cyclical. Various materials may be incorporated into, or as, a layer: for example, a reinforcing material, a fiber, a wire, a braided material, braided wire, braided plastic fibers, and so forth. Similarly, such materials may be excluded. Moreover, the porous solid may be made with a certain property, e.g., Young's modulus, tensile strength, solids content, polymer composition, porous structure, or solvent content that is known and thus measurable exclusive of various other materials. Accordingly, embodiments include materials disclosed herein that are described in terms of the materials' properties without regard to various other incorporated materials. For instance, a nanoporous solid has a certain Young's modulus that is known even if the material has a reinforcing wire that contributes further strength.

A core may be used with an extrusion die. The core may be air, water, a liquid, a solid, a non-solvent or a gas. Artisans reading this disclosure will appreciate that various extrusion processes using these various kinds of cores may be use. Cores made of polytetrafluoroethylene tubing (PTFE) are useful. In some embodiments, a core is a wire.

Multi lumen tubing has multiple channels running through its profile. These extrusions can be custom engineered to meet device designs. Multi Lumen tubing has a variable Outer Diameter (OD), numerous custom Inner Diameters (ID's), and various wall thicknesses. This tubing is available in a number shapes; circular, oval, triangular, square, and crescent. These lumens can be used for guidewires, fluids, gases, wires, and various other needs. The number of lumens in multi lumen tubing is only limited by the size of the OD. In some embodiments, OD's are as large as 0.5 in., ID's can be as small as 0.002 in., and web and wall thicknesses can be as thin as 0.002 in. Tight tolerances can be maintained to +/−. 0005 in. Artisans will immediately appreciate that all ranges and values between the explicitly stated bounds are contemplated, with, e.g., any of the following being available as an upper or lower limit for an OD and/or ID: 0.002, 0.003, 0.004, 0.007, 0.01, 0.02, 0.03, 0.04, 0.05, 0.1, 0.2, 0.3, 0.4, and 0.5 in. Tolerances may be, e.g., from 0.0005 to 0.1 in.; Artisans will immediately appreciate that all ranges and values between the explicitly stated bounds are contemplated, with, e.g., any of the following being available as an upper or lower limit: 0.0005, 0.001, 0.002, 0.003, 0.006, 0.01, 0.02, 0.03, 0.06, 0.8, 0.9, 1 in.

Braid reinforced tubing can be made in various configurations. For instance, it is possible to braid using round or flat, single or double ended wires as small as 0.001 in. Various materials can be used to make the braided reinforced tubing including stainless steel, beryllium copper, and silver, as well as monofilament polymers. The braid can be wound with various pics per inch over many thermoplastic substrates such as nylons or polyurethanes. The benefits of braided catheter shaft are its high torque-ability and kink resistance. By changing several factors during the braiding process, the characteristics of the tube can be altered to fit performance requirements. After braiding is complete, a second extrusion may be applied on top of the braided tube to encapsulate the braid and provide a smooth finish. Walls as thin as 0.007 in. can be achieved when a braid reinforced tube is required.

Porous, Microporous, and Nanoporous Materials

Porous solid is a term used broadly herein to refer to materials having a solid phase containing open spaces and is used to describe true porous materials and also hydrogels having an open matrix structure. Some terms related to porosity are used somewhat loosely in scientific literature such that it is helpful to provide certain definitions herein. The term nanoporous material or nanoporous solid is used herein to specifically refer to a solid made with interconnected pores having a pore size of up to about 100 nm diameter. The term diameter is broad and encompasses pores of any shape, as is customary in these arts. The term microporous solid or microporous material is similarly used herein to specifically refer to a solid made with interconnected pores having a pore size of up to about 10 μm diameter. These nano- or micro-porous materials are characterized by an interconnected porous structure.

Some hydrogels, which artisans sometimes refer to as hydrogel sponges, are also true porous materials that have a continuous and solid network material filled through voids, with the voids being the pores. However, an open matrix structure found in many hydrogels is not a true porous structure and, in general, while it is convenient to refer to them as porous materials, or to use analogies to pores when characterizing diffusive or other properties, such hydrogels are not nanoporous or microporous solids as those terms are used herein. The spaces between strands of an open matrix hydrogel, and the strands of the matrix are not interconnected pores. Hydrogels are crosslinked gels that have solid-like properties without being a true solid although it is convenient herein and generally in these arts to refer to them as a solid because they are crosslinked, insoluble in solvent, and have significant mechanical strength. Hydrogels may have a high-water content, e.g., 25% w/w at EWC or more. Artisans in the hydrogel arts sometimes use the term porous, to characterize a net molecular weight cut off or to refer to spacing between strands of an open hydrogel matrix, in which case the hydrogel does not have a true porous structure and is not a nanoporous or a microporous material as those terms are used herein. The definitions of nanoporous material and microporous material as used herein also contrast with a convention that is sometimes followed wherein microporous substances are described as having pore diameters of less than 2 nm, macroporous substances have pore diameters of greater than 50 nm, and a mesoporous category lies in the middle.

The extrusion process for making the inventive materials has some advantages. The extrusion has been observed to align the polymers to a parallel orientation that contributes to high tensile strength. Having been extruded and stretched, the polymer molecules become aligned in the direction of the tube or fiber. Any tendency to return to a random orientation is prevented by the strong intermolecular forces between the molecules. Further, extrusion provides for creation of materials or devices with a high aspect ratio as compared to injection molding or other molding processes. Moreover, extrusion provides good control of dimensions such that wall thickness, placement of the lumen or lumens can be controlled. The use of high concentrations of polymers, above their melt point, in a solvent was useful for enabling extrusion. It is significant that attempts by others to use similar polymers to make high strength materials used other techniques that do not allow for extrusion, that are less efficient, and often unsuited for making actual end-user products.

For example, poly(vinyl alcohol) (PVA) was used herein to make nanoporous materials with excellent properties, especially as compared to conventionally used PVA medical materials. In fact, PVA has been used extensively throughout the medical device industry with a well-established track record of biocompatibility. PVA is a linear molecule with an extensive history as a biocompatible biomaterial. PVA hydrogels and membranes have been developed for biomedical applications such as contact lenses, artificial pancreases, hemodialysis, and synthetic vitreous humor, as well as for implantable medical materials to replace cartilage and meniscus tissues. It is an attractive material for these applications because of its biocompatibility and low protein adsorption properties resulting in low cell adhesion compared with other hydrogels.

Others have tried to improve the properties of PVA for biomedical purposes. For instance, others have experimented with a freeze/thaw process. And techniques for formation of hydrogels from PVA such as "salting out" gelation have been shown to form useful polymer hydrogels using different molecular weights and concentrations. Manipulation of Flory interactions has also been studied in the formation of PVA gels through the combination of two solutions (see U.S. Pat. Nos. 7,845,670, 8,637,063, 7,619,009) for the use of PVA as an injectable in situ forming gel for repairing intervertebral disks. In general, prior processes for fabricating tough PVA materials were studied in U.S. Pat. No. 8,541,484. Methods for doing so without the use of radiation or chemical crosslinkers have also been previously studied, as shown in U.S. Pat. No. 6,231,605. None of this PVA-related work by others has resulted in the inventions that are set forth herein. Some of these other materials were useful in regards to tensile strength but were nonetheless macroporous in nature.

In contrast, processes herein provide high strength materials with a true porous structure and other useful characteristics such as an unexpectedly good combination of biocompatibility and mechanical properties. Embodiments of porous solid materials are provided that have a combination of structural features independently chosen from pore sizes, tensile strength, Young's modulus, solids concentration, crosslinking type and degree, internal alignment, hydrophilicity, and composition for the materials and further, optionally, independently selecting end-user devices or intermediate materials having a desired aspect ratio for molded shapes, a lumen, a plurality of lumens, tubes with concentrically placed lumens or a range of tolerance of thickness, or a particular medical device: each of these are further detailed herein.

Embodiments include nanoporous materials with pore diameters of 100 nm or less, or within a range of 10-100 nm; Artisans will immediately appreciate that all ranges and values between the explicitly stated bounds are contemplated, with, e.g., any of the following being available as an upper or lower limit: 1, 2, 3, 4, 5, 10, 20, 50, 60, 70 80, 90, 100 nm.

Embodiments include nanoporous materials or microporous materials with a tensile strength at break of at least about 50 MPa or from 1-300 MPa measured at EWC. Artisans will immediately appreciate that all ranges and values between the explicitly stated bounds are contemplated, with, e.g., any of the following being available as an upper or lower limit: 10, 20, 30, 40, 50, 60, 70, 100, 200, 300 MPa.

Embodiments include nanoporous materials or microporous materials with a Young's modulus strength of at least about 1 MPa or from 1-100 MPa measured at EWC. Artisans will immediately appreciate that all ranges and values between the explicitly stated bounds are contemplated, with, e.g., any of the following being available as an upper or lower limit: 5, 10, 15, 20, 25, 30, 35, 40, 50, 60, 70, 80, 90, 100 MPa.

Embodiments include nanoporous materials or microporous materials or hydrogels with an elongation at break of at least about 100% or from 50-1500% measured at EWC. Artisans will immediately appreciate that all ranges and values between the explicitly stated bounds are contemplated, with, e.g., any of the following being available as an upper or lower limit: 50, 60, 70, 80, 90, 100, 200, 300, 400, 450, or 500%.

Embodiments include nanoporous materials or microporous materials or hydrogels with a solids content of at least 20% or solids from 20-90% w/w measured at EWC; Artisans will immediately appreciate that all ranges and values between the explicitly stated bounds are contemplated, with, e.g., any of the following being available as an upper or lower limit: 5, 10, 25, 30, 35, 40, 45, 50, 55, 60, 65, 70, 80, 90% w/w percent solids. Percent solids are measured by comparing a total weight at EWC to dry weight.

The tensile strength, modulus, and elongation values may be mixed-and-matched in combinations within the ranges as guided by this disclosure.

Embodiments include nanoporous materials or microporous materials or hydrogels with physical crosslinks or covalent crosslinks or a combination thereof. Physical crosslinks are non-covalent, e.g., physical crosslinks are ionic bonds, hydrogen bonds, electrostatic bonds, Van Der Waals forces, or hydrophobic packing. The materials may be made free of covalent crosslinks, covalent crosslinkers and chemical products thereof. Chemicals can be added during processing to create covalent crosslinks, as is known in the arts of polymerization. Alternatively, the processes and materials may be free of the same.

Embodiments include nanoporous materials or microporous materials or hydrogels with an internal alignment of the polymeric structure. Alignment may be visualized using SEM images in sections taken along the direction of extrusion, i.e., longitudinally for a tube. Alignment refers to a majority horizontal chain orientation and along the length of samples (in direction of extrusion).

Embodiments include nanoporous materials or microporous materials or hydrogels with a hydrophilic surface and/or material. Materials made from polymers that are water soluble are hydrophilic. A water-soluble polymer is a polymer that is soluble in water at a concentration of at least 1 g/100 ml at 20° C. Water soluble polymers are hydrophilic. A surface is hydrophilic if a contact angle for a water droplet on the surface is less than 90 degrees (the contact angle is defined as the angle passing through the drop interior). Embodiments include hydrophilic surfaces with a contact angle from 90 to 0 degrees; Artisans will immediately appreciate that all ranges and values between the explicitly stated bounds are contemplated, with, e.g., any of the following being available as an upper or lower limit: 90, 80, 70, 60, 50, 40, 30, 20, 10, 5, 2, 0 degrees. A matrix of a material is hydrophilic relative to a solvent when the matrix is hydrophilic and a droplet of the solvent on the surface is less than 90 degrees.

Materials for use in the process and/or biomaterials may include polymers. Hydrophilic polymers are useful, e.g., one or more polymers may be selected from polyvinyl alcohol (PVA), polyvinylpyrrolidone (PVP), polyethylene glycol (PEG), polyacrylic acid (PAA), polyacrylamide, hydroxypropyl methacrylamide, polyoxazolines, polyphosphates, polyphosphazenes, poly(vinyl acetate), polypropylene glycol, Poly(N-isopropylacrylamide) (PNIPAM), polysaccharides, sulfonated hydrophilic polymers (e.g., sulfonated polyphenylene oxide, Nafion®, sulfobetaine methacrylate) and variations of the same with an added iodine (e.g., PVA-I, PVP-I), or variations with further pendent groups, copolymers of the same, and combinations of the same. Two or more hydrophilic polymers may be intermixed together to form a nanoporous material. The molecular weight of the polymer can affect the properties of the biomaterial. A higher molecular weight tends to increase strength, decrease pore size, and decrease protein adsorption. Accordingly, embodiments include a polymer or a hydrophilic polymer having a molecular weight of 40 k to 5000 k daltons; Artisans will immediately appreciate that all ranges and values between the explicitly stated bounds are contemplated, with, e.g., any of the following being available as an upper or lower limit: 40 k, 50 k, 100 k, 125 k, 150 k, 250 k, 400 k, 500 k, 600 k 750 k, 800, 900 k, 1 million, 1.5 million, 2 million, 2.5 million, 3 million molecular weight.

The term PEG refers to all polyethylene oxides regardless of molecular weight or whether or not the polymers are terminated with a hydroxyl. Similarly, the terms PVA, PVP, and PAA are used without limitation as to terminal chemical moieties or MW ranges. References to polymers described herein include all forms of the polymers including linear polymers, branched polymers, underivatized polymers, and derivatized polymers. A branched polymer has a linear backbone and at least one branch and is thus a term that encompasses star, brush, comb, and combinations thereof. A derivatized polymer has a backbone that comprises the indicated repeating unit and one or more substitutions or pendant groups collectively referred to as derivatizing moieties. A substitution refers to a replacement of one atom with another. A pendant group is a chemical moiety attached to the polymer and may be the same or a different moiety as the polymer repeating unit. Accordingly, a reference to a polymer encompasses highly derivatized polymers and also polymers no more than 0.01-20% w/w derivatizing moieties, calculated as the total MW of such moieties compared to the total weight of the polymer. Artisans will immediately appreciate that all ranges and values between the explicitly stated bounds are contemplated, with, e.g., any of the following being available as an upper or lower limit: 0.01, 0.05, 0.1, 0.2, 0.3, 0.5, 1, 2, 3, 4, 5, 6, 7, 8, 9, 10, 15, 20% w/w.

A porous solid may be formed as a monolithic material, as a layer on another material, device, or surface, as a plurality of layers, or as one or more layers of a nanoporous material or a material that comprises a nanoporous material. Thus, for example, a plurality of layers may be extruded, with the layers being independently chosen to form one or more of: a nanoporous material, a microporous material, a hydrogel, a single-polymer material, a material having two or more polymers, and a non-nanoporous material.

The process of making the material can also affect the material properties, including the concentration of polymer in the polymeric mixture passed through a die. Starting PVA or other hydrophilic polymer concentrations may range from, e.g., 5 to 70% weight-volume (w/w) in water; generally, about 10-30% (w/w) is preferable; Artisans will immediately appreciate that all ranges and values between the explicitly stated bounds are contemplated, with, e.g., any of the following being available as an upper or lower limit: 5, 10, 15, 20, 25, 30, 35, 40, 45, 50, 55, 60, 65, 70 percent.

Processes set forth herein may be truncated at a point before polymers crosslink and are processed to become a true nanoporous material, or otherwise adapted to avoid a nanoporous structure. In general, such materials have a lesser strength and toughness and lower solids content. Such materials are generally hydrogels when hydrophilic polymers are used at relatively low solids content. Accordingly, such materials, and even hydrogels, are contemplated herein, and materials may be made that are of somewhat lesser characteristics as compared to the nanoporous materials but, nonetheless, are superior to conventional processes and materials that use the same polymers. Similarly, and as a generalization, a microporous solid would have properties that approach those of the nanoporous materials and would have a strength better than those of a hydrogel.

Artisans are accustomed to quantifying pore size distributions in materials. Nanoporous, microporous, and microporous materials are disclosed herein and control of the pore sizes of such material is demonstrated. Embodiments thus include materials that have a particular quantity or distribution of pore sizes. These can be measured at a surface, in a depth from the surface in a cross-sectional sample, or for the bulk of the material. For instance, the material pore sizes on a surface, at a depth from a surface, or in a bulk may have a percentage from 50-100% of pore diameters that fall within a range, or above or below a certain value, from 1 nm to 20 µm; Artisans will immediately appreciate that all ranges and values between the explicitly stated bounds are contemplated, e.g., 10, 20, 30, 40, 50, 60, 65, 70, 75, 80, 90, 95, 98, 99, 99.9 or 100% and 1, 10, 20, 30, 40, 50, 100, 200, 400, 500, 1000, 2000, 3000, 5000, 10000, 15000, or 20000 nm. Examples of quantitation relative to a depth are at a depth of e.g., at least, or in a range of, 1-5000 µm; Artisans will immediately appreciate that all ranges and values between the explicitly stated bounds are contemplated: 1, 2, 3, 4, 5, 10, 20, 50, 100, 250, 500, 750, 1000, 2000, 3000, 4000, or 5000 µm. For example, a surface may have a certain percentage of pores that are no more than a certain diameter or a depth or depth range may have a certain percentage of pores that are no more than a certain diameter.

Embodiments include a process for making a polymeric material comprising heating a mixture that comprises a water-soluble polymer and a solvent to a temperature above the melting point of the polymer, extruding the mixture, and cooling the mixture while removing the solvent and/or cooling the mixture while it crosslinks. When a plurality of polymers is present in a solvent, either with or without other additives, a melting point of the combined polymers in the solvent can be readily determined by the artisan, for instance by observing the mixture as it is heated and it passes from a cloudy to a markedly more translucent appearance. Further, after, or as part of, a formation process that uses the mixture, some or all of the solvent may be removed from the mixture while the cooling takes place. Embodiments include removing at least 50% w/w of the solvent in less than 60 minutes (or less than 1, 2, 5, or 10 minutes). Embodiments include removing at least 90% w/w (or at least 70% w/w or at least 80% w/w) of the solvent in less than 60 minutes (or less than 1, 2, 5, 10, or 30 minutes).

Bulk Incorporation of Polymers into a Porous Solid

A porous material may be exposed to a mixture comprising solvated polymers (for bulk incorporated polymers) to draw them into the pores when the porous matrix is desolvated. The solvent of the mixture has an affinity for the matrix and is drawn in as the matrix imbibes the solvent. The solvent in the mixture with the bulk incorporated polymers can be chosen to have an affinity for the matrix so that it is imbibed into the desolvated matrix but does not have to be the same as the solvent in the matrix. In general, a hydrophilic solvent in the mixture will be imbibed into a hydrophilic porous matrix that is at least partially desolvated and contains a hydrophilic solvent, and an artisan can adjust the various solvents as needed to create suitable conditions when the goal of bulk incorporation is intended.

A hydrophilic solvent is a solvent that is freely miscible with water or is present at a concentration in the mixture wherein it is freely miscible with water, at 20° C.

Desolvated means that the matrix is free of solvents, e.g., completely dry, or is below an EWC of the matrix relative to the solvent it contains. If the solvent in the matrix is not water, the EWC can be calculated for the material based on measurements in the solvent, i.e., the term EWC can be used for solvents that are not water in the appropriate context. For instance, a hydrophilic matrix might be solvated in an aqueous solution of an alcohol and would have an EWC for that solvent. Embodiments include an amount of desolvation of a porous solid from 1-100, Artisans will immediately appreciate that all ranges and values between the explicitly stated bounds are contemplated: 1, 5, 10, 15, 20, 33, 40, 50, 60, 70, 80, 90, 95, 99, 100% w/w referring to the total weight of solvent that can be removed.

Without being bound to a particular theory, it is believed that porous materials can be desolvated (dehydrated in the case of water being the solvent in the porous material) and exposed to polymers in a solution that resolvates the porous material so that the polymers are drawn into the pores. The polymers then form physical bonds with the matrix material that defines the pores and are, for practical purposes, permanently incorporated into the bulk of the materials, both by at least partially filling the pores and by physical bonding with the matrix. Alternatively, or additionally, the polymers have a hydrodynamic radius that causes the polymer to present a diameter that exceeds the pores' opening diameter so that the polymer is permanently incorporated into the pores of the material, especially when the material is to be used in water or physiological solution. In general, if the bulk-incorporated polymer is solvated in a polymer that wets the pores of the porous solid, the polymer can be drawn into pores of the matrix as it is resolvated. When a hydrophilic porous matrix is below an EWC of the matrix, the mixture that contains the polymers for bulk incorporation is drawn in because the solvent for the polymers is matched to the matrix material, e.g., wets the pores of the material. For instance, a hydrophilic solvent will normally wet the pores of a hydrophilic matrix.

A material that comprises a porous matrix of polymers joined by noncovalent bonds is a preferred embodiment, since these materials can be made with a high degree of control over pore sizes and material properties, including a choice of nanoporous, microporous, or other characteristic pore sizes. The matrix may comprise physically crosslinked water-soluble polymers that define the pores. A solids concentration of these water-soluble polymers may be at least 33% w/w of the matrix at an equilibrium water content (EWC) of the matrix, although other concentrations may also be used.

Accordingly, an embodiment of a process of incorporating polymers in a porous material comprises providing a material comprising a porous, hydrophilic matrix that comprises one or more water soluble polymers (also referred to herein as matrix polymers) crosslinked with each other to form the matrix. The material with the matrix is exposed to a mixture comprising one or more polymers (also referred to as bulk incorporated polymers, preferably with the polymers being water soluble, with the mixture also being referred to as a conditioning mixture or bulk incorporating mixture) solvated in a solvent, wherein the matrix is below the EWC before being exposed to the mixture and is hydrophilic relative to the solvent. The material, before exposure to the mixture with the bulk incorporated polymers, is desolvated.

In general, bulk incorporation processes were observed to create an outer zone wherein the pores were filled, an intermediate zone where most of the pores were filled or are mostly filled, and an inner zone where there was little or no penetration of the polymers, see FIG. 35A. Bulk incorporation not only modifies pores at a surface but also below the surface, e.g., at least, or in a range of, 1-5000 µm; Artisans will immediately appreciate that all ranges and values between the explicitly stated bounds are contemplated, e.g., 1, 2, 3, 4, 5, 10, 20, 30, 40, 50, 75, 100, 250, 500, 750, 1000, 2000, 3000, 4000, or 5000 µm. The percentage of pores that have polymer may be assayed as already described and penetration graded by a cut-off of a percentage, e.g., a first zone having 100% filling of pores, a second zone with 50% pores filled, a third zone with 0% pores filled.

Bulk incorporation processes are preferably made with porous matrices that are made of water soluble polymers and may be made without hydrophobic domains in the polymers, e.g., a matrix made only of PVA. The polymers may form the matrix with physical crosslinks. Accordingly, embodiments include materials comprising matrices that are free of hydrophobic domains or that are made with water soluble polymers that are free of hydrophobic domains or that are free of any polymer that is not water soluble. Some hydrophobic domains can be tolerated, however, when making a hydrophilic matrix with water soluble polymers having physical crosslinks without disrupting the matrix formed thereby. Embodiments of the invention include a hydrophobic content of polymers that form a porous matrix of 0, 1, 2, 3, 4, 5, 7, 8, 9, 10, 11, 12, or 15% w/w.

A porous matrix consisting essentially of water soluble polymers refers to a content of up to 3% w/w of the polymers that crosslink to form the matrix. RO agents such as salts are not polymers that crosslink to form the matrix. A porous matrix consisting essentially of physically crosslinked polymers refers to a matrix that is free of agents that make covalent bonds between the polymers, or has a small amount of such agents so that no more than about 6% of the polymers (referring to polymer number) are crosslinked to each other with such agents, e.g., wherein a stoichiometric ratio of polymer number to a bifunctional crosslinker is at least 100:3. A matrix that is essentially free of covalent bonds similarly is made with polymers crosslinked with no more than about 6% of the polymers (by number) are not covalently crosslinked. The number of covalent bonds in a matrix may similarly be limited to a stoichiometric ratio of 100:3 to 100:100, e.g., 100 to any of 3, 5, 10, 15, 20, 25, 30, 40, 50, 60, 70, 80, 90, or 100 by number. For instance, hydrogels made by free radical polymerization typically have 100% of the polymers attached to each other by covalent bonds, which is a 100:100 stoichiometric ratio of polymers: covalent bonds.

As stated elsewhere, a porous solid can be made with a controlled pore diameter range and may be made to provide a matrix has no pores larger than a particular diameter. Diameters may be measured in an appropriate context, e.g., at EWC in distilled water. Embodiments thus include polymers entrapped in a porous matrix that is free of pores that are larger than 1-5000 μm; Artisans will immediately appreciate that all ranges and values between the explicitly stated bounds are contemplated, e.g., 1, 2, 3, 4, 5, 10, 15, 20, 25, 30, 50, 100, 200, 250, 300, 400, 500, 750, 1000, 2000, 3000, 4000, or 5000 μm.

A porous solid can have other materials present as described elsewhere herein, e.g., radiopaque (RO) agents that are additional to the matrix but are not part of the matrix. RO agents typically contribute little to the crosslinking that provides the strength of the matrix. Similarly, other materials can be present in the matrix without being part of the matrix, e.g., wires and reinforcing materials. It can be appreciated that a matrix made with physical crosslinks is one type of matrix that can be made with materials that define pores that have diameters and is in contrast to hydrogels having polymer strands that are generally separated from each other and are connected in a mesh network structure, e.g., as typically formed using free radical polymerization or by reaction of monomers/polymers that are in solution. Such mesh networks would generally not be expected to stably incorporate polymers in their pores without covalent bonding using a polymer-imbibing process. Porous materials are described in detail herein and these may be freely chosen, as guided by the disclosure herein, for use with bulk incorporated polymers. The porous material may be chosen with bulk properties as described herein.

The bulk incorporated polymers may be polymers described elsewhere herein for porous solids. Examples are water-soluble polymers. The water soluble polymers may be, for example, polyvinyl alcohol (PVA), polyvinylpyrrolidone (PVP), polyethylene glycol (PEG), polyacrylic acid (PAA), polyacrylamide, hydroxypropyl methacrylamide, polyoxazolines, polyphosphates, polyphosphazenes, poly (vinyl acetate), polypropylene glycol, Poly(N-isopropylacrylamide) (PNIPAM), polysaccharides, sulfonated hydrophilic polymers (e.g., sulfonated polyphenylene oxide, Nafion®, sulfobetaine methacrylate) and variations of the same with an added iodine (e.g., PVA-I, PVP-I), or variations with further pendent groups, copolymers of the same, and combinations of the same. The mixture may comprise one or more polymers, meaning polymers of different chemical compositions, such as PVA and PEG. The term "a polymer" refers to one or more polymers.

The solubility of a water-soluble polymer for a porous matrix or for bulk incorporation may be chosen as, e.g., at least 1, 2, 5, or 10 g/100 ml in water at 20° C. Polymers may be chosen to be linear or branched. Embodiments include a polymer or a hydrophilic polymer having a molecular weight of, e.g., 40 k to 5000 k Daltons; Artisans will immediately appreciate that all ranges and values between the explicitly stated bounds are contemplated, with, e.g., any of the following being available as an upper or lower limit: 40 k, 50 k, 100 k, 125 k, 150 k, 250 k, 400 k, 500 k, 600 k 750 k, 800, 900 k, 1 million, 1.5 million, 2 million, 2.5 million, 3 million molecular weight. The molecular weight of the polymer can be chosen in light of the pore sizes available in the porous solid. Nanoporous or microporous materials are preferred.

The bulk incorporated polymers may be chosen to be the same as polymers that form the porous matrix, to be the same as at least one of the polymers that make up the matrix, or to be different.

The bulk incorporated polymer concentrations in the mixture may be, referring to the mixture at the start of the process, any concentration wherein the polymers go into solution, bearing in mind that polymer that is not in solution, or other non-solvated materials, are not destined to enter pores. In some embodiments, concentrations are 1-50% w/w; Artisans will immediately appreciate that all ranges and values between the explicitly stated bounds are contemplated, e.g., 1, 2, 3, 4, 5, 10, 15, 20, 25, 30, 33, 35, 40, 50% w/w.

Solvent for the mixture is chosen as appropriate to solvate the polymer and to provide a solvent that will be imbibed by the porous solid. Hydrophilic solvents are generally preferable for a hydrophilic matrix. Solvents may be water, organic, or aqueous, or free of the same, e.g., free of organic solvent. In some embodiments, concentrations of water are 0-99, e.g., 0, 5, 10, 15, 20, 25, 30, 40, 50, 60, 70, 80, 90, 95, or 99 w/w %.

A temperature of the conditioning mixture is not to exceed a melting temperature of the porous solid matrix. Temperatures ranges may be, for example, from 10-100° C., e.g., 10, 20, 30, 37, 40, 50, 60, 70, 80, or 90° C.

Exposure times are preferably for a duration of time required for a porous solid to reach EWC in the mixture. Duration of time may comprise, in some embodiments, 2, 4, 6, 8, 10, 12, 16, 20, 24, and 48 hours. Agitation and temperature may be manipulated to affect a time of exposure, e.g., to accelerate achieving EWC or to control viscosity of the mixture. Salt and/or osmotic content may be adjusted as helpful, e.g., for solubility, viscosity, and/or EWC.

The Examples provide guidance in regards to salt concentration for a conditioning mixture. Examples of salt concentration are from 0.1 to 2% w/w. In general, a single charge cation with a smaller atomic radius has a greater penetration into a depth of a porous solid, whereas a larger cation reduces penetration. Examples of salts are those with a single cation, divalent cation, or other cation, e.g., a salt of sodium, potassium, lithium, copper, quaternary ammonium (NR4+, where R is a hydrogen, alkyl, or aryl group), magnesium, calcium, copper, iron, or zinc. In general, a physiological pH using a buffer was useful for the mixture. A pH may be adjusted to increase or decrease penetration into a matrix, and the solvent may include or omit buffering salts. Examples of pH are from 4-10, e.g., 4, 5, 6, 7, 8, 9, or 10.

A viscosity of a conditioning mixture, referring to a water-soluble polymer and solvent, is affected by: pH (higher pH, higher viscosity), polymer concentration and/or molecular weight, and polymer branching, with increases in any of these generally leading to a higher viscosity. In general, a higher viscosity reduces penetration of the bulk incorporating polymers into a porous solid. An embodiment is a porous material comprising water soluble polymers entrapped in pores of a porous matrix. The matrix may comprise physically crosslinked water-soluble polymers that are crosslinked with each other to form the matrix and define the pores. The matrix may have features as disclosed herein, e.g., polymer content, weight percentage of polymers, strength, Young's modulus, degree of coverage, pore sizes, and so forth.

Surface coverage of the water-soluble polymers in a porous matrix may be complete. Complete coverage under SEM conditions wherein no pores of the underlying surface are visible indicates coverage at EWC. A degree of coverage may be less than 100%, e.g., from 50-100%; Artisans will immediately appreciate that all ranges and values between the explicitly stated bounds are contemplated, e.g., 50, 60, 70, 80, 90, 95, 98, 99, 99.9, or 100%.

Bulk incorporation can decrease physical properties of a porous solid, as described above in Example 24. Embodiments thus include a porous solid, e.g., one as disclosed herein, with a Young's modulus and/or tensile strength that is from 1-20% less as a result of being conditioned with a water-soluble polymer as compared to the same material that has not been conditioned with a water-soluble polymer; Artisans will immediately appreciate that all ranges and values between the explicitly stated bounds are contemplated, e.g., 1, 2, 3, 4, 5, 7, 9, 10, 12, 15, or 20%. Example 22 provided a test for exposure of a material for stable incorporation of a water-soluble polymer. A test for incorporation of water soluble polymers to be stable is: Immersion of the test article in physiologically representative fluid (i.e. PBS) at body temp conditions in a circulating peristaltic loop with the test article placed directly in the head of the pump at a flow rate of 10-12 mL/s for 24 hrs at 150 rpm, approximating 500,000 mechanical sample compressions with a volume flux rate of 0.1225 $cm^3*s^{-1}*cm^{-2}$. While testing revealed as much as a 25% loss, other test criteria may be used, e.g., a loss of 0-50% w/w, e.g., 1, 5, 10, 15, 20, 25, 30, 40, 50% w/w. Or other tests may be posed, e.g., a loss of 0-5% w/w e.g., 1, 2, 3, 4, or 5% w/w at 1-52 weeks of static exposure to an excess of PBS, e.g., 1, 2, 3, 4, 5, 10, 20, 30, 40, 50, or 52 weeks.

Products

Products, including end-user or intermediate products, or materials, may be made that have an aspect ratio as desired, e.g., at least 3:1, referring to materials set forth herein including nanoporous materials, microporous materials, and hydrogels. The aspect ratio increases as the device increases in length and decreases in width. Artisans will immediately appreciate that all ranges and values between the explicitly stated bounds are contemplated, with, e.g., any of the following being available as an upper or lower limit: 3:1, 4:1, 5:1, 6:1, 7:1, 8:1, 9:1, 10:1, 50:1, 100:1, 1000:1. A high aspect ratio is highly advantageous for certain devices, e.g., many types of catheters. In principle, a thin tube could be continuously extruded without limitation as to length. Such devices include, e.g., tubes, rods, cylinders, and cross-sections with square, polygonal, or round profiles. One or more lumens may be provided in any of the same. The devices may be made of a single material, essentially a single material, or with a plurality of materials including the various layers already discussed, or a reinforcing material, a fiber, a wire, a braided material, braided wire, braided plastic fibers.

The extrusion process, in particular, provides for concentric placement of a lumen; concentric is in contrast to eccentric meaning the lumen is off-center. In the case of a plurality of lumens, the lumens may be placed so that the lumens are symmetrically placed: the symmetry is in contrast to an eccentric placement of the lumens that is a result of a poorly controlled process. Embodiments include the aforementioned devices with an aspect ratio of at least 3:1 with lumens that are positioned without eccentricity or one lumen that is concentric with the longitudinal axis of the device.

The porous solids such as the nanoporous materials, microporous materials, and strong hydrogels may be used to make catheters or medical fibers. These may be made with bulk incorporated polymers and may have the various features described for the same. Examples of catheters are central venous, peripheral central, midline, peripheral, tunneled, dialysis access, urinary, neurological, peritoneal, intra-aortic balloon pump, diagnostic, interventional, drug delivery, etc.), shunts, wound drains (external including ventricular, ventriculoperitoneal, and lumboperitoneal), and infusion ports. The porous solids may be used to make implantable devices, including fully implantable and percutaneously implanted, either permanent or temporary. The porous solid materials may be used to make blood-contacting devices or devices that contact bodily fluids, including ex vivo and/or in vivo devices, and including blood contacting implants. Examples of such devices drug delivery devices (e.g., insulin pump), tubing, contraceptive devices, feminine hygiene, endoscopes, grafts (including small diameter<6 mm), pacemakers, implantable cardioverter-defibrillators, cardiac resynchronization devices, cardiovascular device leads, ventricular assist devices, catheters (including cochlear implants, endotracheal tubes, tracheostomy tubes, drug delivery ports and tubing, implantable sensors (intravascular, transdermal, intracranial), ventilator pumps, and ophthalmic devices including drug delivery systems. Catheters can comprise a tubular nanoporous material with a fastener to cooperate with other devices, e.g., luer fasteners or fittings. Radiopaque agents may be added to the materials, fibers, or devices. The term radiopaque agent refers to agents commonly used in the medical device industry to add radiopacity to materials, e.g., barium sulfate, bismuth, or tungsten. RO agents may be incorporated at, e.g., from 5-50% w/w pf the total solids weight, e.g., 5, 10, 20, 30, 40, or 50%.

Medical fibers made with porous solid materials include applications such as sutures, yarns, medical textiles, braids, mesh, knitted or woven mesh, nonwoven fabrics, and devices based on the same. The fibers are strong and pliable. Materials may be made with these fibers so that they are resistant to fatigue and abrasion.

In an exemplary embodiment, the method comprises administering, into an external orifice of a subject, a polymeric material comprising a water-soluble polymer and having an aspect ratio of greater than or equal to 3:1, wherein administration of the article (e.g., article 10 of FIG. 1A, article 12 of FIG. 1B) does not comprise the use of a sheath introducer. The polymeric material is substantially non-thrombogenic, the polymeric material has a water content of less than 5 w/w % and greater than or equal to 0.1 w/w % in the dehydrated state, and the polymeric material is configured to swell in an amount greater than or equal to 5 w/w % and less than or equal to 50 w/w % from a dehydrated state to an equilibrium water content state in less than or equal to 60 minutes.

Further Definitions

The term medically acceptable refers to a material that is highly purified to be free of contaminants and is nontoxic. The term consists essentially of, as used in the context of a biomaterial or medical device, refers to a material or device that has no more than 3% w/w of other materials or components and said 3% does not make the device unsuited to intended medical uses. Equilibrium water content (EWC) is a term that refers to the water content of a material when the wet weight of the material has become constant, and before the material degrades. In general, materials with a high solids content have been observed to be at equilibrium water content at 24-48 hours. For purposes of measuring EWC, distilled water is used unless otherwise specified.

The term w/v refers to weight per volume e.g., g/L or mg/mL. The terms biomaterial and biomedical material are used interchangeably herein and encompass biomedically acceptable materials directed to a use in the biomedical arts, for example, as implants, catheters, blood-contacting materials, tissue-contacting materials, diagnostic assays, medical kits, tissue sample processing, or other medical purposes. Moreover, while the materials are suited for biomedical uses, they are not limited to the same and may be created as general-purpose materials. A physiological saline refers to a phosphate buffered solution with a pH of 7-7.4 and a human physiological osmolarity at 37° C.

The term molecular weight (MW) is measured in g/mol. The MW of a polymer refers to a weight average MW unless otherwise stated. When the polymer is part of a porous solid, the term MW refers to the polymer before it is crosslinked. When a distance between crosslinks is specified, it is the weight average MW between crosslinks unless otherwise indicated. The abbreviation k stands for thousand, M stands for million, and G stands for billion such that 50 k MW refers to 50,000 MW. Daltons is also a unit of MW and likewise refers to a weight average when used for a polymer.

Publications, journal articles, patents and patent applications referenced herein are hereby incorporated herein for all purposes, with the instant specification controlling in case of conflict. Features of embodiments set forth herein may be mixed and matched as guided by the need to make an operable process or product.

As used herein, the term "therapeutic agent" or also referred to as a "drug" refers to an agent that is administered to a subject to treat a disease, disorder, or other clinically recognized condition, or for prophylactic purposes, and has a clinically significant effect on the body of the subject to treat and/or prevent the disease, disorder, or condition.

As used herein, when a component is referred to as being "adjacent" another component, it can be directly adjacent to (e.g., in contact with) the component, or one or more intervening components also may be present. A component that is "directly adjacent" another component means that no intervening component(s) is present.

A "subject" refers to any animal such as a mammal (e.g., a human). Non-limiting examples of subjects include a human, a non-human primate, a cow, a horse, a pig, a sheep, a goat, a dog, a cat or a rodent such as a mouse, a rat, a hamster, a bird, a fish, or a guinea pig. Generally, the invention is directed toward use with humans. In some embodiments, a subject may demonstrate health benefits, e.g., upon administration of the self-righting article.

As used herein, a "fluid" is given its ordinary meaning, i.e., a liquid or a gas. A fluid cannot maintain a defined shape and will flow during an observable time frame to fill the container in which it is put. Thus, the fluid may have any suitable viscosity that permits flow. If two or more fluids are present, each fluid may be independently selected among essentially any fluids (liquids, gases, and the like) by those of ordinary skill in the art.

EXAMPLES

The following examples are intended to illustrate some embodiments described herein, including some aspects of the present invention, but do not exemplify the full scope of the invention.

Example 1A: Extrusion of a PVA Porous Solid

The examples use the apparatus of FIG. 1 when an extrusion is described unless otherwise indicated. A 17% by weight PVA solution was prepared using 100 ml deionized water and 20 g PVA (Mw=85 kDa, Sigma-Aldrich). Water was heated to until water just began to boil (100° C.) and then dry PVA was added slowly (over approximately 5-10 minutes) to the water while mixing moderately (mixer speed of approximately 40). Heating was stopped just as or before boiling began to prevent boiling (i.e. a process that is free of boiling). Once all PVA was added and the solution began to thicken, heat was decreased to approximately 90° C. and the stir speed was increased to high so insure that the polymer completely dissolved and was fully blended. The PVA solution was stirred for approximately 2 hours. Upon completion, the solution was thick and slightly opaque. Solution was poured into a 20 cc syringe and degassed in an oven at 90° C.; heating/degassing does not typically exceed 2 hours.

The polymer sample was extruded into a bath of 13° C. ethanol (Fisher, 190 proof) using a PTFE monofilament (e.g., core) puller speed of 7 (ARDUINO specific motor moving software, 84 mm diameter puller wheel). Once the sample was extruded, it was left undisturbed in the cold ethanol for approximately 30 minutes before it was moved. The sample was then moved into a separate container of ethanol and placed in a freezer at −25° C. for 24 hours. The core (e.g., the monofilament) was then removed from the sample by clamping the edge of the monofilament with tongs and slowly sliding the sample off. A mandrel slightly smaller than the inner diameter (0.033 in.) of the sample was inserted into the sample and the sample was dried flat in an incubator at 50° C. for approximately 3 hours. After complete drying, samples were annealed by submerging in 120° C. glycerol (Sigma-Aldrich) in a closed container for 24±4 hours in oven. After annealing, samples were removed from glycerol and rinsed gently with deionized water. Samples were then transferred to a fresh container of deionized water to rehydrate for approximately 24 hours. Samples can be dehydrated and rehydrated without negative effects or changes to the porous solid being observed. This process produced a catheter comprising a nanoporous solid material.

Example 1B: Molded PVA

PVA gels were prepared by weighing out 10 g of 85 k MW PVA (88% hydrolyzed) and adding to 100 mL of diH2O under agitation, heated to 80° C. The PVA was added slowly and allowed to mix before elevating the temperature to 90° C. The PVA solution was agitated until clarity was achieved. Approximately 5 mL of PVA solution was drawn into a syringe and degassed to remove entrapped air. The PVA solution was injected into a preheated mold at 60° C., then rapidly cooled using a refrigerated cooling source. PVA gels were then removed intact on mandrels from the mold.

The PVA gels were quenched in a 6 M solution of NaCl. The PVA gels were allowed to soak overnight in the salt solution (16-24 hrs), then removed. The hardened gels were then removed from the mandrels in their hydrated state to remove excess salt and soaked for an additional 24 hrs in diH$_2$O. Gels were then dehydrated to remove any residual water by drying for 24 hours at 25° C.

Some of the gels were then annealed by submerging them in mineral oil and heating to 140° C. for 1 hour. Gels were completely flushed and submerged in the oil to ensure no portion was exposed. Gels were allowed to cool, rinsed with 20 mL of diH$_2$O, and then set to rehydrate in an additional 20 mL of diH$_2$O at 37° C. Other samples of the gels were annealed by submergence in glycerin and heating to 120-130° C. for 3-24 hours. Gels were completely flushed and submerged in the glycerin to ensure no portion was left exposed to air. Gels were allowed to cool, rinsed with 20 mL of diH$_2$O, and then set to rehydrate in an additional 20 mL of diH$_2$O at 37° C.

Example 2: Extrusion of PVA-Barium

A PVA-barium polymer solution was prepared using 100 ml of deionized water, 16 grams of 85 kDa PVA (Sigma-Aldrich) and 4 g of barium sulfate (Sigma-Aldrich). Water was heated until it just began to boil (100° C.); dry barium sulfate was first added slowly and mixed until clumps were no long observed. Dry PVA was then added slowly (over approximately 5 minutes) to the water while mixing moderately. Once all PVA was added and the solution began to thicken, heat was decreased to approximately 90° C. and stir speed was increased to high to insure that the polymer completely dissolved and was fully blended. The PVA-barium solution was stirred vigorously for approximately 2 hours. Upon completion, the solution was thick and white. The solution was poured into a 20 cc syringe and degassed in an oven at 90° C.; heating during degassing does not typically exceed 2 hours.

Once the sample was extruded according to methods similar to those described in Example 1, it was left undisturbed in the cold ethanol for approximately 30 minutes before it was moved. Sample sizes after exiting the die of the extruder into the ethanol bath approximated 3 mm OD and remained solid yet pliable. The sample was then moved into a separate container of ethanol and placed in the freezer set at −25° C. for 24 hours to allow for complete dehydration into a stable opaque smooth white tube. The sample did not freeze. The monofilament (e.g., the core) was then removed from the sample by clamping the edge of the monofilament with tongs, and slowly sliding the sample off. A mandrel slightly smaller than the inner diameter of the sample was inserted into the sample and the sample was dried flat in an incubator at 50° C. for approximately 3 hours. After complete drying, samples were annealed by submerging in 120° C. glycerol (Sigma-Aldrich) in a closed container for 24±4 hours in oven. A stiff, opaque smooth tube was produced.

After annealing, samples were removed from glycerol and rinsed gently with deionized water. Samples were then transferred to a fresh container of deionized water to rehydrate for approximately 24 hours. Samples can be dehydrated and rehydrated without negative effects or changes being observed.

Example 3: Rehydration/Dehydration Rates of PVA Porous Material

A percent loss of 55% was observed in PVA samples made as described in Example 1A as 3.5 French catheters over a 23-hour period. A plot of the weight loss over time in ambient air are show below in Table 2 and FIG. 9.

TABLE 2

Weight loss over time of PVA sample in ambient conditions

| time (min) | weight (g) |
|---|---|
| 0.1 | 0.2043 |
| 1 | 0.2026 |
| 2 | 0.2021 |
| 3 | 0.2015 |
| 4 | 0.2003 |
| 5 | 0.199 |
| 10 | 0.1931 |
| 15 | 0.1872 |
| 20 | 0.1824 |
| 25 | 0.1745 |
| 55 | 0.1533 |
| 80 | 0.1409 |
| 95 | 0.1345 |
| 100 | 0.1323 |
| 130 | 0.1256 |
| 135 | 0.1248 |
| 1405 | 0.1094 |

Example 4: Tensile Testing Example

Samples of PVA extrusions were made by heating a slurry of 17.6 g of bismuth subcarbonate and 100 g of 6.2 g/L of monosodium phosphate solution to 95° C. jacketed reaction vessel and allowed to heat to temperature. To this, 25.8 g of PVA (Mowiol 28-99, Mw 145 kDa or Sekisui Selvol 165, aka 67-99, Mw 186 kDa) was added over 5 min time period while mixing at 70% Run setting (D.I.T. CV2 Mixer). Polymer was mixed for 1 to 1.5 hours at 70% Run setting. Polymer was degassed at 90° C. for less than 2 hours. Polymer then extruded into 5° C. to 10° C. in 190 proof ethanol and stored at ambient conditions for at least 30 minutes.

The polymer was dried for 3 hours at 55° C. and annealed for 1.5 hours at 140° C. in a forced convection oven. The samples were then rehydrated for 2 hours in 1×PBS in 37° C. After anneal and rehydration the extruded samples had an OD of 1.55 mm and 1.46 mm for the PVA 28-99 and PVA 67-99 respectively, and an ID of 0.69 mm and 0.76 mm for the PVA 28-99 and PVA 67-99 respectively.

Tensile strength (Stress) was measured in Newtons on a Mark 10 Tensile Tester (Model DC4060) with a 100 N digital force gauge (Model #M5-1006). Using calipers (Mark 10 Model #500-474) to measure the outer diameter and a pin gauge set to measure inner diameter, a cross sectional area was determined for the samples. PVA 67-99 indicates nominal viscosity (as a 4% solution in water) of 67 cPs with greater than 99% hydrolysis. PVA 28-99 indicates nominal viscosity (as a 4% solution in water) of 28 cPs with greater than 99% hydrolysis. The viscosity of the PVA is positively correlated to the molecular weight of the polymer.

Figure 10:
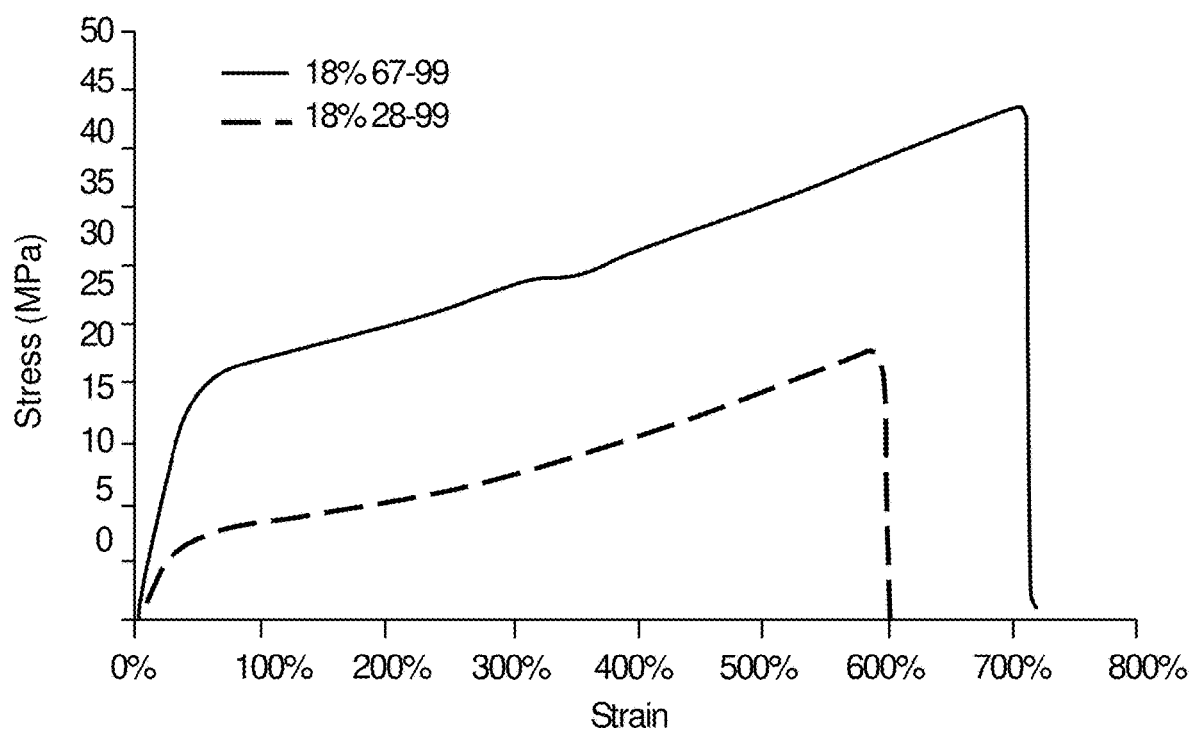
FIG. 10 is a plot of tensile test data for a porous solid made according to Example 4, with the higher molecular weight polymer (PVA 67-99) providing a greater modulus and tensile strength than the lower molecular weight polymer (PVA 28-99).

Table 3 and FIG. 10 show an increase of Young's Modulus as well as maximum tensile stress with an increase of PVA viscosity.

TABLE 3

Stress-Strain characteristics of PVA 28-99 vs PVA 67-99

|  | PVA 28-99 | PVA 67-99 |
|---|---|---|
| Bismuth Subcarbonate (w/w % solids) | 40% | 40% |
| % w/w PVA in Batch | 18% | 18% |
| Outer Diameter (mm) | 1.55 | 1.46 |
| Inner Diameter (mm) | 0.69 | 0.76 |
| Cross Sectional Area (mm$^2$) | 1.52 | 1.22 |
| Max Stress (N/mm$^2$) | 22.7 | 43.4 |
| Modulus (MPa) | 20.6 | 49.1 |
| Maximum Elongation | 595% | 705% |

Samples of 18% PVA extrusions were made by heating a slurry of 17.6 g of bismuth subcarbonate and 100 g of 6.2 g/L of monosodium phosphate solution to 95° C. jacketed reaction vessel and allowed to heat to temperature. To this, 25.8 g of PVA (MOWIOL 28-99) was added over 5 min time period while mixing at 70% Run setting (D.I.T. CV2 Mixer).

Samples of 22% PVA extrusions were made by heating a slurry of 23.3 g of bismuth subcarbonate and 100 g of 6.2 g/L of monosodium phosphate solution to 95° C. jacketed reaction vessel and allowed to heat to temperature. To this, 35.0 g of PVA (MOWIOL 28-99) was added over 5 min time period while mixing at 70% Run setting (D.I.T. CV2 Mixer).

Samples of 26% PVA extrusions were made by heating a slurry of 35.4 g of bismuth subcarbonate and 115.9 g of 6.2 g/L of monosodium phosphate solution to 95° C. jacketed reaction vessel and allowed to heat to temperature. To this, 53.2 g of PVA (MOWIOL 28-99) was added over 5 min time period while mixing at 70% Run setting (D.I.T. CV2 Mixer).

Each set of polymer was mixed for 1.5 to 2 hours at 70% Run setting. Polymer was degassed at 90° C. for less than 2 hours. Polymer then extruded into 5° C. to 10° C. in 190 proof ethanol and store at ambient conditions for at least 30 minutes.

The polymer was dried for 24 hours in a vacuum oven at 40° C. and annealed for 1 hour in silicone oil at 140. The samples were rinsed with 190 proof ethanol 3 times then rehydrated for 2 hours in 1×PBS in 37° C. Various preparations are described in Table 4 and shown in Table 5.

TABLE 4

First preparation

|  | 8% 1 PVA 28-99 | 22% PVA 28-99 | 26% PVA 28-99 |
|---|---|---|---|
| % w/w PVA in Batch | 18.0% | 22.0% | 26.0% |
| Bismuth Subcarbonate | 12.0% | 14.7% | 17.3% |
| 3.2 g/L Monosodium Phosphate Solution | 70.0% | 63.3% | 56.7% |

Figure 11:
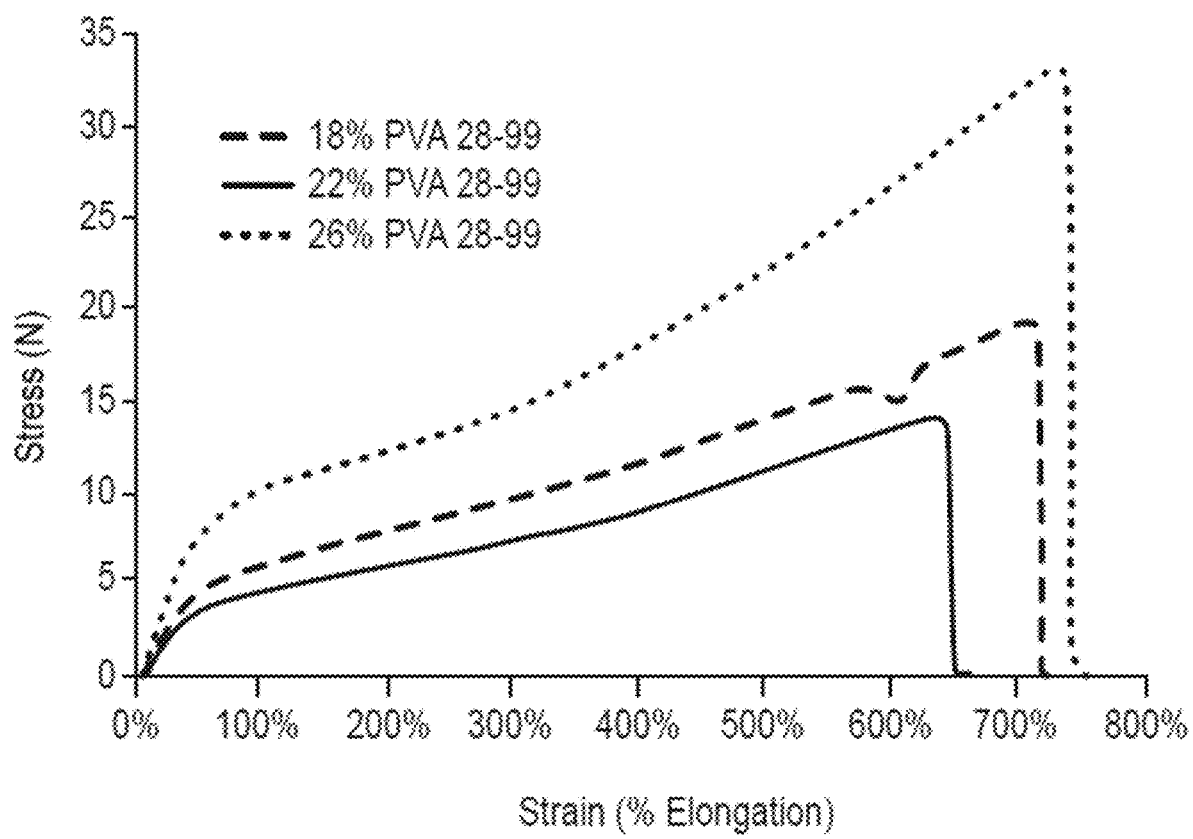
FIG. 11 is a plot of tensile test data for a porous solid made according to Example 4, with the highest concentration of the polymer (26%) providing the material of greatest modulus and tensile strength relative to lower polymer concentrations (22% or 18%).

PVA in the mixtures of Table 4 was increased in a batching step in relation to monobasic salt solution. An increase in PVA provided a higher maximum tensile strength and a higher Young's Modulus. With an increase in a ratio of PVA to monosodium phosphate, a stronger material can be prepared. FIG. 11 and Table 5 show that 26% PVA 28-99 has an increase in Young's Modulus and Maximum Tensile Stress compared to 22% and 18% PVA 28-99. Samples showed increased OD as PVA was ranged, shown in Table 5. OD measurements were 1.32, 1.40 and 1.48 mm for 18, 22 and 26% PVA concentrations respectively; ID did not vary drastically, ranging between 0.71 and 0.76 mm for samples.

TABLE 5

Increase of PVA in the batch

|  | 18% PVA 28-99 | 22% PVA 28-99 | 26% PVA 28-99 |
|---|---|---|---|
| Bismuth Subcarbonate (wt % solids) | 40% | 40% | 40% |
| % PVA in Batch | 18% | 22% | 26% |
| Outer Diameter (mm) | 1.32 | 1.40 | 1.48 |
| Inner Diameter (mm) | 0.71 | 0.71 | 0.76 |
| Cross Sectional Area (mm$^2$) | 0.97 | 1.14 | 1.26 |
| Max Stress (N/mm$^2$) | 19.3 | 14.1 | 33.2 |
| Modulus (MPa) | 14.0 | 10.8 | 18.5 |
| Maximum Elongation | 729% | 665% | 755% |

Example 5: Attachment of Extension Tube/Luer Lock to Hydrogel

A luer lock was bonded via cyanoacrylate to a polyurethane (PU) extension tube. The extension tube was mated to the PVA catheter body by sliding over PVA catheter body approximately 0.5 in. A heat gun used at approximately 300° F., PU/PVA overlap exposed 10× at 0.5 s intervals, process repeated until infusion bonding of PU and PVA occurred. Tensile data was evaluated for multiple samples:

TABLE 6

Tensile data for luer lock attached to PVA porous material

| Sample # | Tensile Strength (lbs) | OD (in) |
|---|---|---|
| 1 | 3.130 | 0.070 |
| 2 | 5.600 | 0.082 |
| 3 | 6.090 | 0.095 |
| 4 | 6.810 | 0.095 |
| 5 | 3.940 | 0.094 |
| 6 | 3.440 | 0.094 |
| 7 | 2.830 | 0.080 |
| 8 | 4.360 | 0.079 |
| 9 | 1.800 | 0.043 |
| 10 | 3.220 | 0.049 |
| 11 | 4.660 | 0.060 |

Further testing showed that a conventional ethylene-vinyl acetate (EVA) bonding process for attaching extensions or other devices to a catheter was effective for bonding such devices to an extruded porous PVA material. Table 7 shows results wherein the points of attachment exceeded the PVA strength or otherwise exceeded all design requirements. A standard natural color EVA melt-liner 3/16 in. O.D. with 0.014 in. wall and Polyolefin RNF 0.25 in. heat shrink was used in conjunction with PVA tubes (0.050 in. ID/0.063 in.-0.065 in. OD) and luer hub with tube assemblies (0.062 in. ID/0.101 in. O.D.). A Steinel HG2310 LCD heat gun with temperature set at 400° F.; (nozzle is 0.25 in. dia. size and modified tip to be 0.12 in. wide by compression to provide a narrow heat zone area) and 0.050 in. stainless mandrels were inserted through the luer hub/tube assemblies into the ID of the PVA tubes.

Three samples using a PE hub and PVA tube butt weld were made at 400° F. The joint was observed to be very strong.

The clear luer hub and tube assembly was slipped over the PVA extrusion about 0.75 in. deep and the ethyl vinyl acetate melt liner and polyolefin added over the assembly. A melt was made and joined at 400° F. Upon noticing the melting of the PVA extrusion and meltliner, a more controlled shrinking method was employed using gentle hand-rolling of the melted joint to shape smooth and prevent melting of the PVA tube.

The PVA extrusion was inserted inside the hub and tube and joined using the methods described above. The strength was very good. Assemblies could not be pulled apart by hand. Two samples were formed and used for hydration and testing. Samples were tensile tested after two hours of conditioning in PBS at 37° C., with results shown in Table 7.

TABLE 7

| Sample | Tensile (N) | Failure Mode/Point | Travel Distance (mm) |
| --- | --- | --- | --- |
| PE Extension Tube 1 | 12.07 | Catheter tube | 28.27 |
| PE Extension Tube 2 | 11.74 | In EVA bond | 40.78 |
| PU Extension Tube 1 | 10.53 | Catheter tube | 30.28 |
| PU Extension Tube 2 | 9.69 | Catheter tube | 91.38 |
| PU Extension Tube 3 | 9.28 | Catheter tube | 85.96 |

Attachment of a suture wing overmold was also successful. An injection-mold of a suture wing was made with EVA (Ateva 2803G with 20% bismuth subcarbonate). It conjoined an extension line (HTP Meds #2006-0335 Rev A) and a PVA tube. A maximum break force of 27 N (6.1 lbf) (Wagner Instruments #FDK 30) required to disconnect the PVA tube and the EVA suture wing. When the assembled PICC was hydrated the break force was 28 N (6.2 lbf).

Example 6: Radiopacity

Samples were made according to methods of Example 2, except using bismuth subcarbonate as the radiopaque agent. The samples are depicted in FIGS. 12A-12F: Control (12A, BARD PowerPICC), 5.7% bismuth subcarbonate by weight, not annealed (21B), 12.1% bismuth subcarbonate by weight, not annealed (12C), 12.1% bismuth subcarbonate by weight, annealed (12D), 5.7% bismuth subcarbonate by weight, annealed (12E), 4.2% bismuth subcarbonate by weight (12F). Extruded samples after alcohol exposure had OD ranges of 2.71-2.84 mm, with consistent IDs of 1.397 mm. After annealing, samples had OD ranges of 1.63-1.93 mm, with ID of 0.97-1.04 mm. Hydration of the materials post annealing in glycerol resulted in hydrated ODs ranging 1.89-2.44 mm, with ID ranges of 1.19-1.25 mm.

All samples B-E exceed radiopacity of control sample. 4.2% bismuth subcarbonate sample (12F) showed about the same level or less of radiopacity and is considered a minimum for the samples. Radiopacity testing was performed at Mount Auburn Hospital in Cambridge, MA.

Example 7: Power Infusion

Pressure testing showed that the extruded porous plastics exceeded all design requirements. Power injection testing was performed for samples of PVA-RO (radiopaque) agent incorporated nanoporous solid made according to Example 2 using a Medrad MARK V PLUS POWER INJECTOR. Samples were attached to a barb/luer fitting with silicone tubing.

Water was injected at 5 mL/sec for 1 second with the sample not occluded (free flowing) and passed without sample failure. Another same sample for the same PVA-RO formulation was then occluded and tested using the same parameters; the sample failed at the extension tube bond due to preexisting damage caused by heat shrink processing.

Figure 13:
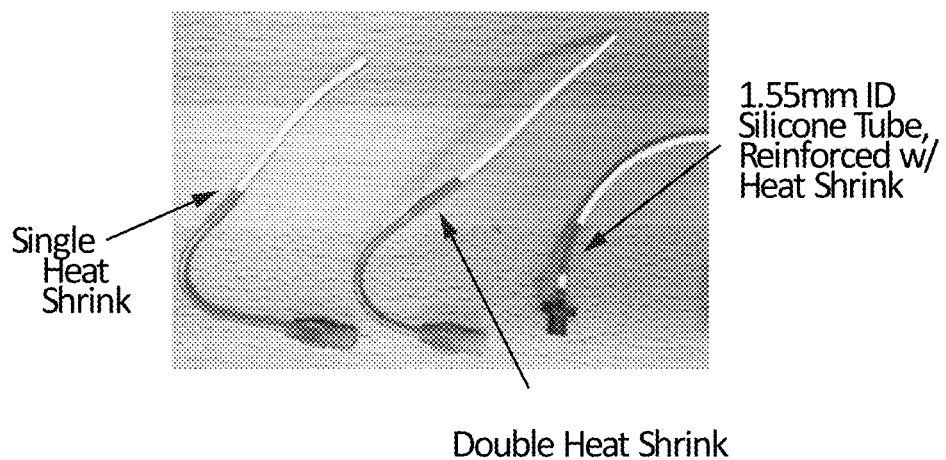
FIG. 13 is a photograph of a first set of test samples described in Example 7.
Figure 14:
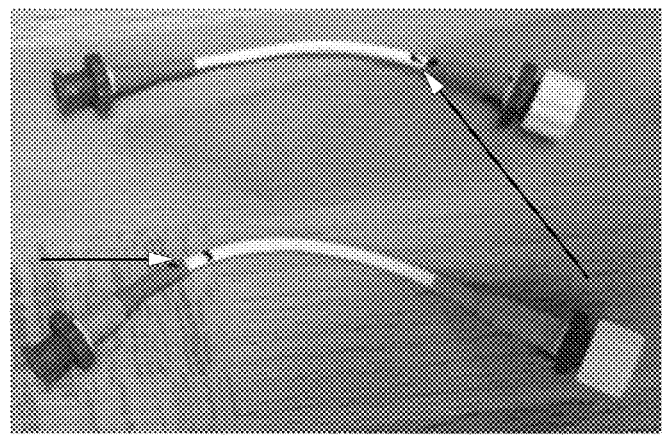
FIG. 14 is a photograph of a second set of test samples described in Example 7.

Another set of samples shown in FIG. 13 were then attached to barbed fittings with Loctite 4902 on silicone tubing and heat shrink using methods described in Example 5; a barb was attached to each end of the sample to allow capping for occlusion testing. Samples 1 and 2 were testing using a flow rate of 5 mL/sec, with a total liquid volume of 5 ML at 100 PSI; samples failed near heat shrink joints due to bonding heat exposure (failure locations indicated in FIG. 14).

Sample 3 was tested using a reduced injection rate and volume and passed 2 of 3 cycles for the following cycles: Cycle 1 used a flow of 0.4 mL/sec and 1 mL total volume at 100 max PSI, cycle 2 used the same parameters with 200 max PSI; both cycles passed. Cycle 3 used a flow of 5.0 mL/sec with 1 mL total volume and 350 max PSI; failure occurred with the tube separated from silicone and heat shrink; no damage to hydrogel was observed, indicating that using the proper attachment method (i.e., overmolding), the PVA extruded tubes were capable of withstanding power injection.

Example 8: Contact Angle

Contact angle was determined for PVA-RO incorporated hydrogel made according to Example 2. A 1 cm section of extruded material was cut from main strand using fresh blade; sample was then carefully cut along length of section. Loctite 406 used to carefully attach sample to a glass slide; once fully adhered, Loctite 406 was dabbed along edged of sample and walls of samples were gently pushed onto glass slide with forceps until a flat configuration was achieved. Using a 20 µl pipettor, a single small drop of colored water was dropped onto the surface of the material; drop was immediately photographed and imported to an image viewer to measure contact angle of droplet. All surfaces and camera were leveled prior to testing. The sample had a contact angle of 60° (taken through the drop) as measured by the drop test.

Example 9: SEM Results

Figure 15A:
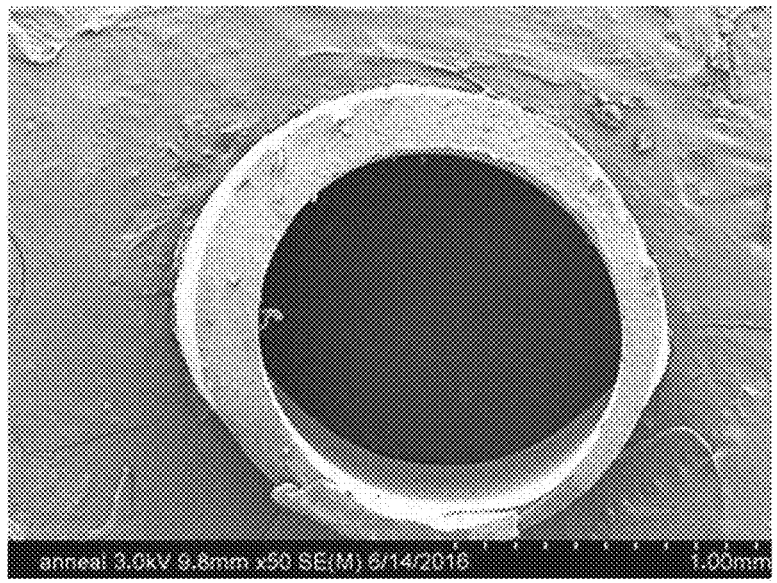
FIGS. 15A-15B are scanning electron micrographs (SEMs) of transverse (15A) or longitudinal (15B) cross sections of a porous solid extruded as described in Example 8.
Figure 15B:
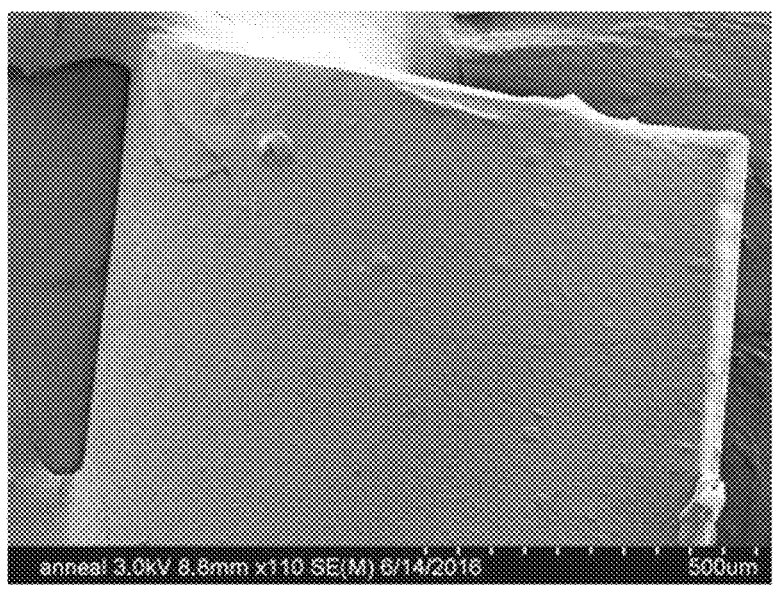

FIGS. 15A-15B are SEM images of a 17% PVA solution extruded using the methods of Example 1A except as otherwise specified. Samples were hydrated in distilled water for 24 hours at 37° C. and then rapidly frozen using liquid nitrogen to preserve pore structure. Samples were then lyophilized for 48 hours to remove water and submitted for SEM analysis. FIG. 15A shows a cross section of an extruded PVA tube, showing no macroporosity in the gel structure. FIG. 15B shows a longitudinal cross section of the extruded tube at a higher magnification, demonstrating no macroporosity to the structure. This material had a high-water content and is highly porous, with the pores no more than about 10 nm in diameter.

Figure 2:
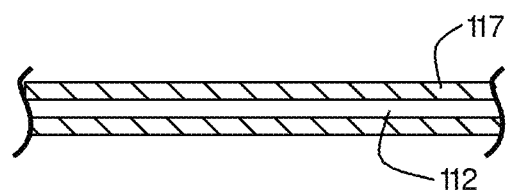
FIG. 2 is a longitudinal cross section of a portion of a continuous porous solid as formed with the apparatus of FIGS. 1C-1E.
Figure 16A:
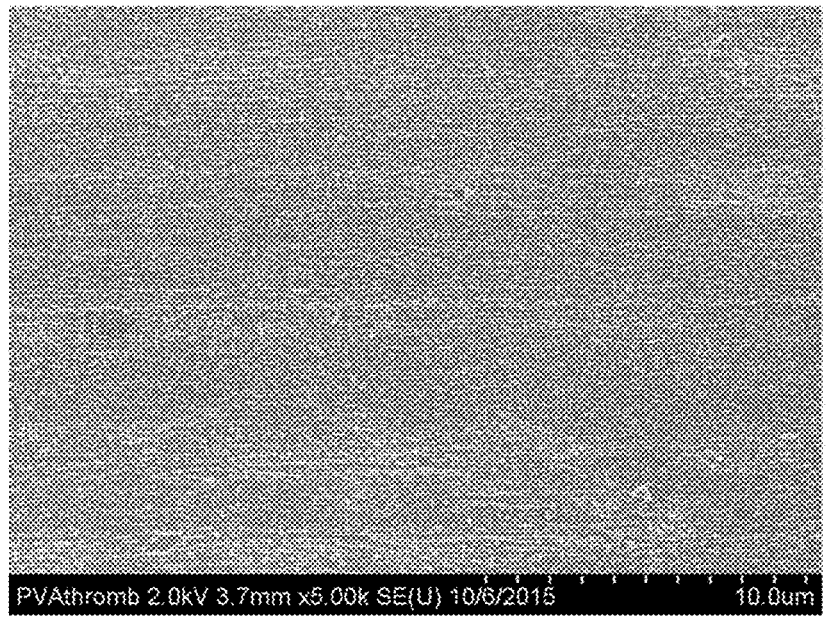
FIGS. 16A-16D are SEMs of a hydrophilic nanoporous material prepared as described in Example 9, provided at various magnifications as indicated by the scale bars.
Figure 16B:
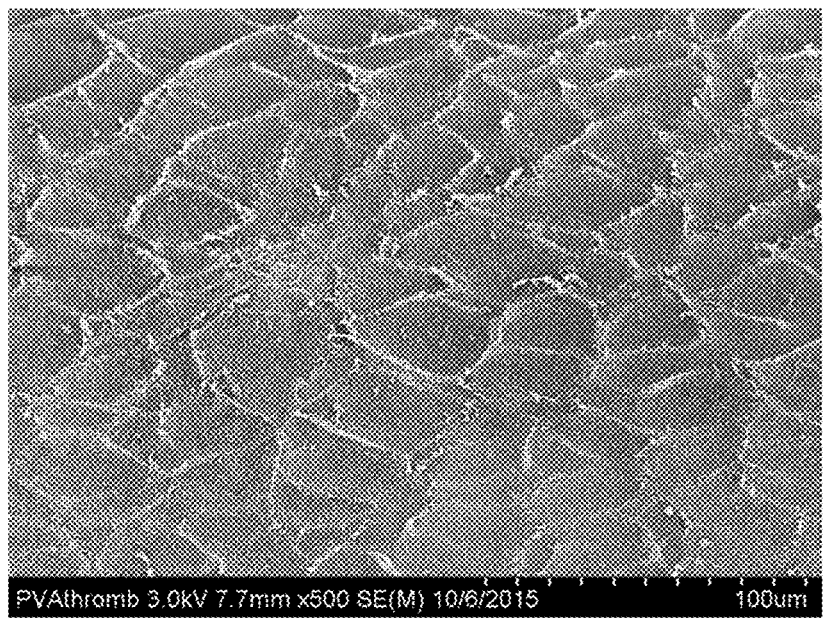
Figure 16C:
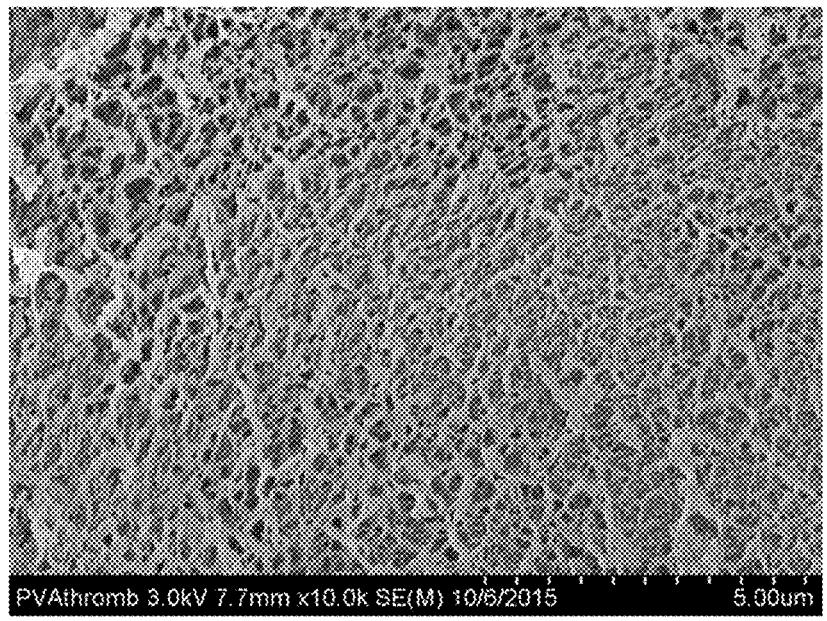
Figure 16D:
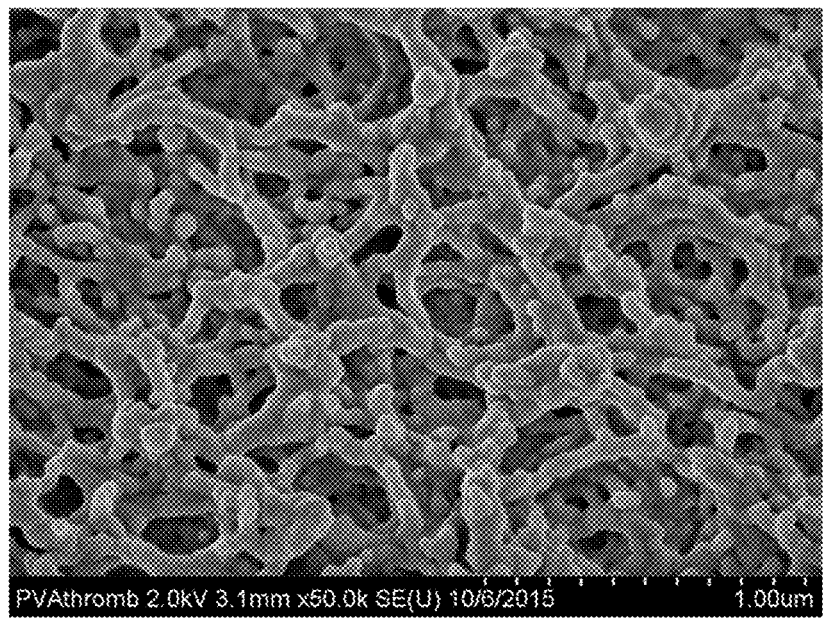

Samples of PVA extrusions were also made by heating 200 g distilled water to 95° C. jacketed reaction vessel and allowed to heat to temperature. To this, 40 g of PVA (Sigma, 146 k-186 k) was added over 5 min time period while mixing at 200 RPM. Polymer was mixed for 1.5 hours at 300 RPM. Polymer was degassed at 90° C. for less than 2 hours. Polymer then extruded into −23° C. ethanol with the apparatus of FIGS. 1-3 and then stored in ethanol at −25° C. in freezer for 24 hours. Samples were dried for 6 hours. After drying, samples were submerged in 120° C. glycerol for 17 hours. After annealing, samples removed and allowed to cool before being rinsed with ethanol; cores removed after rinse. Samples dried for 12 hours at 50° C. Two SEM images, FIGS. 16A-16D, show the results. FIGS. 16C-16D are taken at a high magnification demonstrating nanoporosity.

Example 10: Salt Additives

Various salts were used in the batching process, referring to the process of driving the polymer into solution in the polymer-solvent mixture, to alter the maximum tensile stress and Young's Modulus. Multifunctional salts were used such as phosphoric acid, boric acid, and citric acid. These salts were added in at varying degrees of neutralization as sodium and/or potassium salts.

PBS (phosphate buffered saline) contains sodium chloride, potassium chloride and phosphate salts as it major constituents. Three neutralization points were analyzed in comparison to PBS. A mixture of 18% PVA (MW 146 k-186 k, Sigma Aldrich #363065), 6% bismuth subcarbonate (Foster) (20 w/w % based on solids) and a constant molar ratio of these phosphate salt solutions at 51.7 mM was examined with phosphoric acid (Sigma Aldrich), monosodium (Sigma Aldrich), and disodium phosphate (Sigma Aldrich) in water. Monosodium phosphate resulted in the highest Young's Modulus, where phosphoric acid produced the highest tensile. FIG. 17A is a plot of tensile strengths for 18% PVA samples compounded with PBS, monosodium phosphate, disodium phosphate and phosphoric acid. The effect of other multifunctional (two or more neutralization sites) salts were also evaluated, with results as plotted in FIG. 17B. Boric acid (Sigma Aldrich), citric acid (Sigma Aldrich) and phosphoric acid (Sigma Aldrich) are compared at 18% PVA (Sigma Aldrich), 6% bismuth subcarbonate (Foster) (20 w/w % based on solids) with 51.7 mM of the respective acid solution. Boric acid increased both Young's Modulus and maximum tensile stress, whereas citric acid and phosphoric acid are relatively the same.

Dimensions of the samples after hydration at 37° C. in PBS for the various salt additives were as follows:

TABLE 8A

|  | PBS | Phosphoric acid | Monosodium Phosphate | Disodium phosphate |
| --- | --- | --- | --- | --- |
| ID (mm) | 0.762 | 0.76 | 0.8382 | 0.76 |
| OD (mm) | 1.85 | 1.23 | 1.34 | 1.32 |
| Cross Sectional area (mm$^2$) | 2.23 | 0.73 | 0.86 | 0.91 |

|  | Citric Acid | Boric Acid | Phosphoric acid |
| --- | --- | --- | --- |
| ID (mm) | 0.81 | 0.81 | 0.76 |
| OD (mm) | 1.37 | 1.33 | 1.23 |
| Cross Sectional area (mm$^2$) | 0.96 | 0.87 | 0.73 |

Example 11: PVA and PAA Blend Batching and Copolymer Extrusion

PVA-PAA blend solutions were batched using the following method; see Table 8 for formulation composition. 100 g water and PVA were added to high viscosity jacketed vessel heated to 90° C. and mixed at 600 RPM. Bismuth subcarbonate concentrate was homogenized with remaining water for 15 minutes and then 32 g of the concentrate was added to 90° C. jacketed reaction vessel, unless otherwise specified. PVA was then added to vessel while mixing 600 RPM. PAA was added to solution after 1 hour of mixing and continued for 0.5 hours until solution was totally homogenous. Polymer was then aliquoted into 20 mL syringes.

TABLE 8B

PVA-PAA Blend Formulation Composition

| No. | % PAA | Molecular Weight PAA | g PVA | g Water | g Bismuth Subcarbonate Concentrate | g PAA |
| --- | --- | --- | --- | --- | --- | --- |
| 1 | 0.1 | 450k | 16.0 | 100 | 32.0 | 0.125 |
| 2 | 0.4 | 450k | 16.0 | 100 | 32.0 | 0.500 |
| 3 | 4.0 | 450k | 16.0 | 100 | 7.0 (RO only) | 5.125 |
| 4 | 0.2 | 3m | 16.0 | 100 | 10.0 (RO only) | 0.500 |
| 5 | 0.3 | 3m | 16.0 | 100 | 32.0 | 0.500 |
| 6 | 0.4 | 3m | 16.0 | 100 | 7.0 (RO only) | 0.500 |

Polymer was reheated to 90° C. and degassed at 90° C. for 1 hour. Polymer was then extruded into approximately 10° C. to approximately 21° C. ethanol. Extrudate was allowed to sit in ethanol on monofilament for approximately 0.5 hours. Extrudate was then transferred to room temperature ethanol and allowed to dehydrate for 24 hours with monofilament removed.

Extrudate was transferred to vacuum oven and dried at 50° C. for 48 hours. After drying, samples were injected with 120° C. USP grade mineral oil and then submerged in 120° C. mineral oil in a convection oven for 2 hours. Samples were then removed from mineral and allowed to cool to room temperature. A rinse/flush procedure was performed once with ethanol and twice with distilled water. Samples transferred to 37° C. PBS to hydrate before tensile testing and surface evaluation. After hydration, samples were smooth on the surface and ranged in OD from 1.8 to 2.4 mm, and 1.5 to 1.6 mm in ID. Tensile testing was performed as per ISO-10555 protocols. Tensile values are not normalized to sample cross sectional area.

Figure 18B:
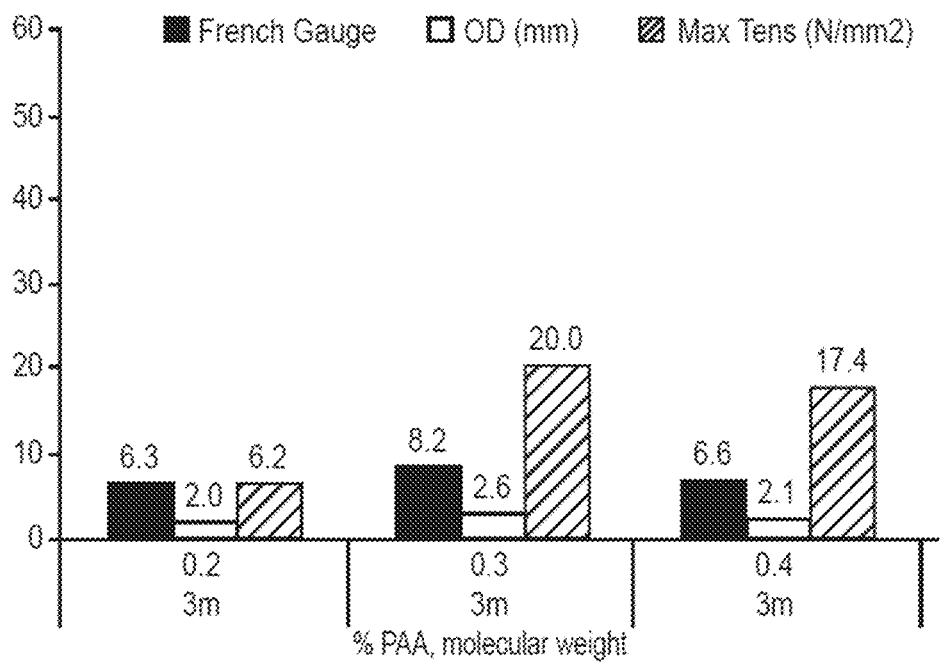

FIG. 18A is a comparison of PVA-PAA blend formulations of 450 k molecular weight PAA. PAA formulations at 0.1% and 0.4% (w/w) concentrations in water extruded with PVA in an 11-13% concentrations showed higher tensile strength than 4.0% formulations. Higher water content may be correlated to increased percent of PAA, decreasing of strength between PVA bonds, therefore reducing tensile strength. Moreover, the 4.0% 450 k PAA formulations exhibited a spongey looking surface. FIG. 18B is a comparison of PVA-PAA Blend Formulations of 3 m Molecular Weight PAA. PAA formulations of 3 m molecular weight at 0.3% and 0.4% (w/w relative to solvent) concentration showed higher tensile strength than 0.2% formulation. The 3 m molecular weight PAA-containing formulations exhibited approximately half of the tensile strength of 450 k PAA-containing formulations, excluding 4.0%.

Example 12: PVA and PEG Blend Batching and Copolymer Extrusion

PVA-PEG blend solutions were batched using the following method; see Table 9, PVA (Sigma, 146 k-186 k), bismuth subcarbonate (Foster), 100 g distilled water, and PEG 8 k (Sigma), PEG 20 k (Sigma), or PEG 35 k (Sigma). Bismuth subcarbonate was homogenized with water for 15 minutes and then added to 90° C. jacketed reaction vessel. PVA was then added to vessel while mixing at 600 RPM for 2 hours; PEG was then added to solution and mixing continued for 2 hours until solution was totally homogenous. Polymer was then aliquoted into 20 mL syringes.

TABLE 9

PVA-PEG Blend Formulation Composition

| No. | % PEG | Molecular Weight PEG | g PVA | g Water | g Bismuth Subcarbonate | g PEG |
|---|---|---|---|---|---|---|
| 1 | 1 | 8k | 16.0 | 100 | 7.0 | 1.25 |
| 2 | 1 | 20k | 16.0 | 100 | 7.0 | 1.25 |
| 3 | 1 | 35k | 16.0 | 100 | 7.0 | 1.25 |

Polymer was reheated to 90° C. and extruded into approximately 3° C. to 21° C. ethanol with an approximate OD of 2.3-2.4 mm. Extrudate was allowed to sit in ethanol on monofilament for approximately 1 hour. Extrudate was then transferred to room temperature ethanol and allowed to dehydrate for 24 hours with monofilament removed.

Figure 19:
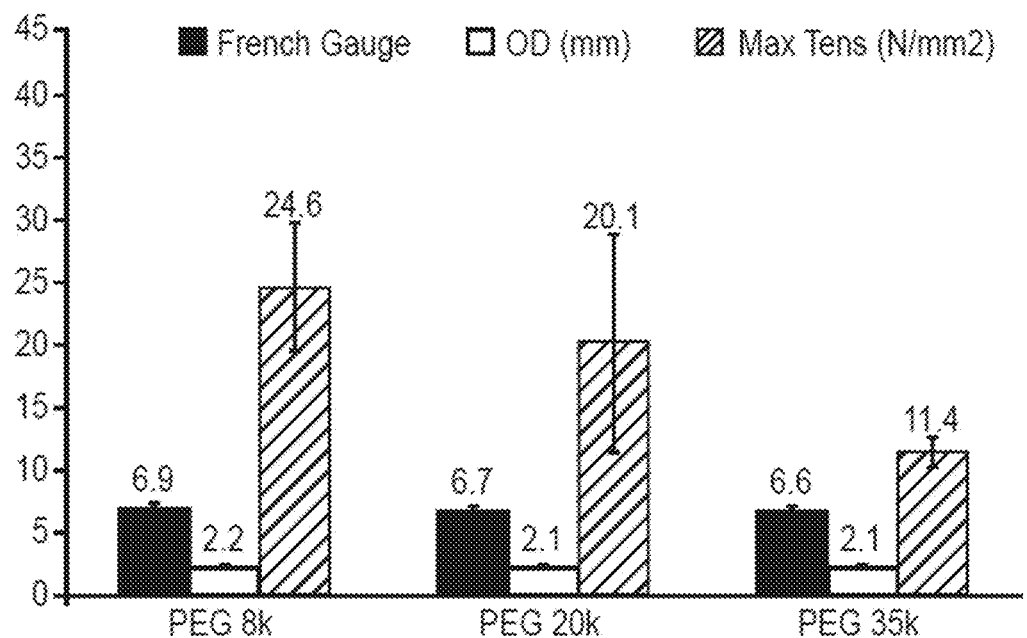
FIG. 19 is a plot of tensile data for various blends of polymers described in Example 12, with data being shown in $N/mm^2$.
Figure 20A:
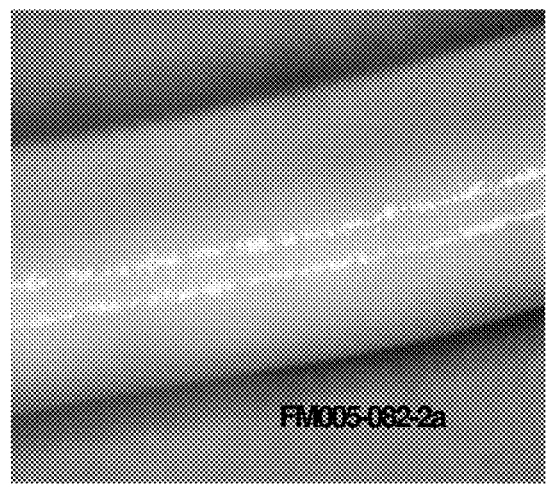
FIGS. 20A-20C are photograph of a PEG/PVA copolymer extrusion described in Example 12 depicting surfaces with a PEG molecular weight of 8 k (20A), 20 k (20B), or 35K (20C).
Figure 20B:
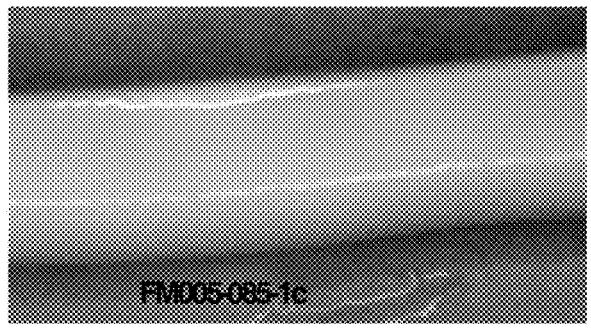
Figure 20C:
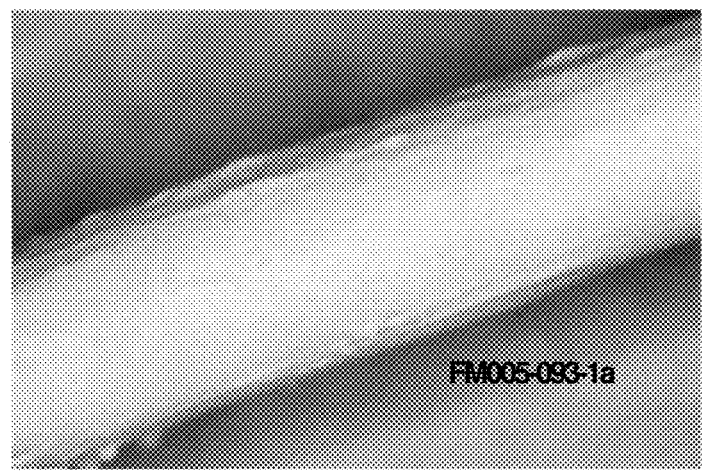
Figure 21A:
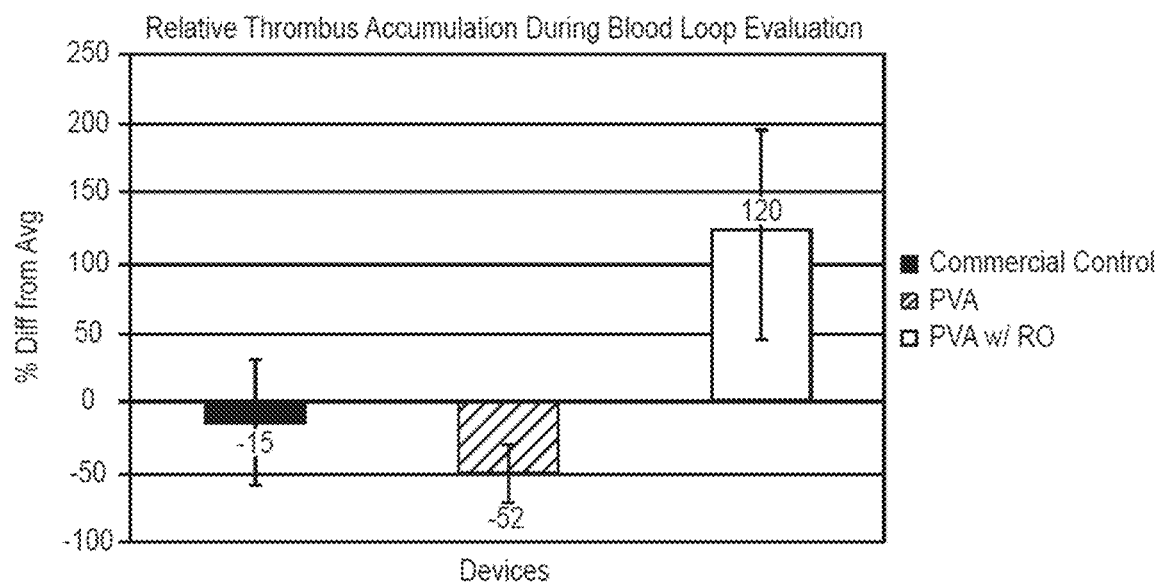
FIGS. 21A-21B provide results of blood contact experiments described in Example 15 as a plot of relative thrombus accumulation (21A) or photographs of the tested samples (21B).

Extrudate was transferred to vacuum oven and dried at 50° C. for 48 hours. After drying, samples were injected with 120° C. USP grade mineral oil and then submerged in 120° C. mineral oil in a convection oven for 2 hours. Samples were then removed from mineral and allowed to cool to room temperature, then measured for OD and wall thickness. Samples were approximately 1.9 to 2.3 mm in diameter with wall thicknesses of 0.48 mm. A rinse/flush procedure was performed once with ethanol and twice with distilled water. Samples transferred to distilled water to hydrate before tensile testing and surface evaluation. Tensile testing was performed as per ISO-10555 protocols. FIG. 19 depicts the results and shows a comparison of PVA-1% PEG formulations of varying MW PEG; note that tensile values are not normalized to sample cross sectional area. PEG blend extrudate resulted in a smooth surface, excluding PEG 35 k which produced a scale pattern along outside of extrudate. Due to wide standard deviations of all 1% PEG blends, there is no significant difference observed in tensile strength of 8 k, 20 k 35 k PEG co-extrusions. FIGS. 20A-20C are photographs of the 8 k, 20k, 35k, PEG co-extrusions, respectively.

Example 13: Thrombogenic Evaluation of a PVA Gel

Samples of PVA extrusions were made by heating 200 g distilled water to 95° C. jacketed reaction vessel and allowed to heat to temperature. To this, 40 g of PVA (Sigma, 146 k-186 k) was added over 5 min time period while mixing at 200 RPM. Polymer was mixed for 1.5 hours at 300 RPM. Polymer was degassed at 90° C. for less than 2 hours. Polymer then extruded into −23° C. ethanol and then stored in ethanol at −25° C. in freezer for 24 hours. Samples were dried for 6 hours.

After drying, samples were submerged in 120° C. glycerol for 17 hours. After annealing, samples removed and allowed to cool before being rinsed with ethanol; cores removed after rinse. Samples dried for 12 hours at 50° C.

Samples of PVA with barium sulfate were made by heating 50 g water in a jacketed reaction vessel at 90° C. In a side vessel, 4 g of barium sulfate and 50 g water homogenized for 15 minutes at 11 k RPM and then added to the jacketed vessel. This was mixed for 10 minutes to heat. After heating, 16 g of PVA (Sigma, 146 k-186 k) was added and mixed at 360 RPM for approximately 2 hours.

The PVA-RO polymer mixture was heated to 90° C. and extruded into −16° C. ethanol. The extrudate was allowed to dehydrate at −25° C. for 24 hours. Cores were removed and samples dried in an incubator at 50° C. for approximately 6 hours. After drying, samples were submerged in 120° C. glycerol (Sigma) for 17 hours. After annealing, samples removed and allowed to cool before being rinsed with distilled water. Samples dried at 50° C. for 12 hours and packaged for testing.

Samples were evaluated for nonthrombogenic durability testing at Thrombodyne, Inc. (Salt Lake City, UT). Each sample was cut to 15 cm in length with an N=5 per sample group. Prior to testing, samples were sterilized using a 12-hour ethylene oxide exposure; samples were hydra tested for approximately 48 hours in distilled water prior to evaluation to represent clinical use.

Fresh heparinized bovine blood with autologous $^{111}$In-labeled platelets was divided into portions for test sample and control evaluation. Samples were inserted into an in vitro blood flow loop of 0.25 in. ID polyvinyl chloride tubing for approximately 120 minutes. Blood was kept at 98° C. and pumped through the blood loop using a peristaltic pump for the duration of testing. Samples were initially checked for thrombi after 45 minutes in the blood flow loop and removed at 120 minutes. At the end of the experiment, the devices were explanted from the tubing, rinsed with saline, and placed in a gamma counter for thrombus quantification. Experiment parameter are presented in Table 10. Each experiment consisted of an independent flow system per test sample and/or control circulating blood from the same animal to enable simultaneous comparisons without cross-over effects.

Figure 21B:
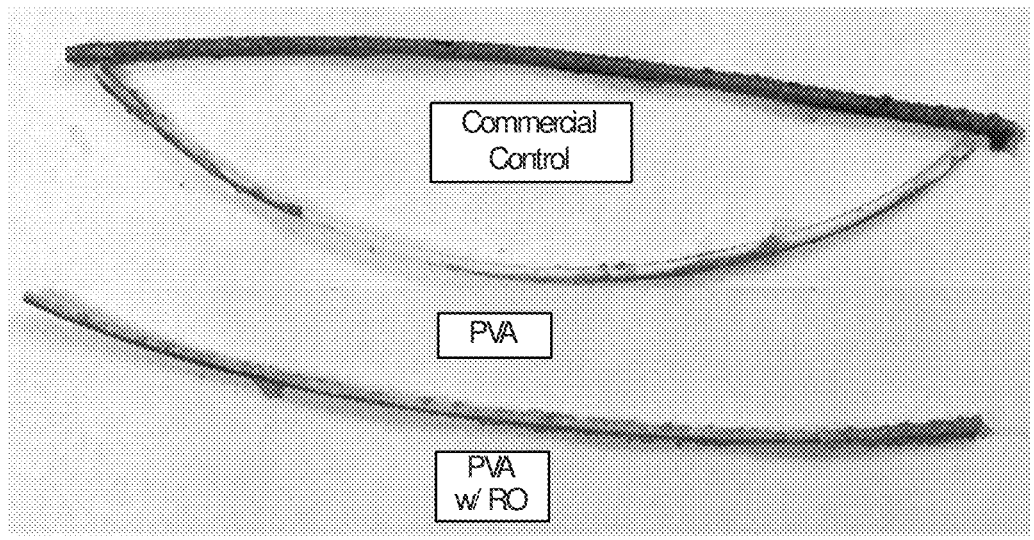

Samples were measured for radioactivity and also qualitatively assessed for specific types of thrombus accumulation (i.e. adhesion or fibrin accumulation). Count results are provided in Table 10. Percent thrombosis was calculated relative to the average total thrombosis observed across all test and control groups per animal blood circulated. Results for thrombus accumulation are provided in Tables 11-12 and depicted in FIG. 21A. Visual assessment of the thrombosis is shown in FIG. 21B, with a commercially available control catheter, a 17% PVA extrusion, and the 17% PVA-barium sulfate extrusion.

TABLE 10

Experimental Parameters

| | |
|---|---|
| Heparin Concentration | 0.7 EU/mL |
| Internal diameter of tubing in which device was deployed | 0.25 in. |

TABLE 10-continued

Experimental Parameters

| | |
|---|---|
| Blood flow rate | 20 mL/min |
| Experiment time | 60-12 min |
| Number of replications (N)** | 6 |

**Blood from a different animal was used in different replications

TABLE 11

Raw Radiation Data for 6 French Polyurethane Control and Hydrogel Formulations

| Raw Radiation counts per minute (CPM) Polyurethane Control | Raw Radiation counts per minute (CPM) PVA Formulation | PVA w/RO (PVA-barium) | Average |
|---|---|---|---|
| Expt #1 | 6305 | 8928 | 11509 | 8914 |
| Expt #2 | 9219 | 1803 | 4624 | 5215 |
| Expt #3 | 1194 | 765 | 4101 | 2020 |
| Expt #4 | 8226 | 3095 | 10692 | 7338 |
| Expt #5 | 677 | 2536 | 24837 | 9350 |

TABLE 12

Relative Thrombus Accumulation Based on Percent Difference from Average per Animal

| | % Difference From Average | | |
|---|---|---|---|
| | Polyurethane Control | PVA Formulation | PVA w/RO (PVA-barium) |
| Expt #1 | −29.27 | 0.16 | 29.11 |
| Expt #2 | 76.77 | −65.43 | 17.71 |
| Expt #3 | −40.89 | −62.13 | 163.87 |
| Expt #4 | 12.11 | −57.82 | 113.99 |
| Expt #5 | −92.76 | −72.88 | 273.46 |
| Mean | −15 | −52 | 120 |
| Std. Error | 44.8 | 20.8 | 74.4 |

The results show a reduction in thrombi for PVA formulation compared to a commercially available PICC. The PVA-RO (barium as RO agent) formulation was not superior to the control. Possible reasons include the lack of barium micronization and evidence of larger barium particles on the surface of the extrusion.

Example 14: Incorporation of Polyacrylic acid (PAA) into Extruded PVA

A porous solid was prepared according to the process of Example 1A, with the further inclusion of polyacrylic acid (PAA) and other changes described as follows. A PVA-PAA solution was prepared by first preparing a 13% by weight PVA polymer solution in physiological phosphate buffer solution (PBS) using 200 g of PBS (lot SLBH9016, Sigma-Aldrich), 32 g PVA (lot MKBR1224V, Sigma-Aldrich, Mw 146-186 kDa) and 14 g bismuth subcarbonate (Foster). PBS was heated to 90° C. and then dry PVA was added slowly while mixing moderately. Once all PVA was added and the solution began to thicken, stir speed was increased to high to ensure that the polymer completely dissolved and was fully blended, and then the bismuth subcarbonate was added to form the final suspension. The PVA solution was stirred for approximately 2 hours. Upon completion, the solution was thick and opaque. The suspension was poured into a 20 cc syringe and degassed in an oven at 90° C.; heating during degassing was approximately 4 hours.

The PVA-containing mixture was extruded into a bath of 3° C. ethanol (lot SHBF8329V, Sigma-Aldrich) using a monofilament puller speed of 7 (Arduino specific motor moving software, 84 mm diameter puller wheel) to achieve a gauge size of 6 French.

Once the sample was extruded, it was left undisturbed in the cold ethanol for approximately 30 minutes before it was moved. The sample was then moved into a separate container of ethanol for 24 hours. The monofilament was then removed from the sample by clamping the edge of the monofilament with tongs, and slowly sliding the sample off. A mandrel slightly smaller than the inner diameter (0.033 inches) of the sample was inserted into the sample and the sample was dried flat in an incubator at 40° C. for approximately 24 hours. After complete drying, samples were soaked for 24 hours in a solution of 5% PAA which was prepared using 2.5 g of PAA (lot MKBT4716V, Mw 450 kDa) and 50 ml of deionized water (lot BCBP9977V, Sigma-Aldrich) at 45° C. Samples were then air-dried hanging for approximately 3 hours, then dried again in an incubator at 40° C. After drying, samples were annealed by being submerged in 120° C. anhydrous glycerol (lot BCBM4755V, Sigma-Aldrich) in a closed container for 17 hours in an oven.

After annealing, samples were removed from glycerol and rinsed gently with deionized water and placed back into incubator to dehydrate. Samples were transferred to a fresh container of deionized water to rehydrate, for approximately 24 hours. Samples can be dehydrated and rehydrated without negative effects or changes being observed.

Example 15: Non-Fouling in Blood Loop

Nonthrombogenic durability testing was performed at Thrombodyne, Inc. (Salt Lake City, UT). Porous solid PVA tubing including a radiopaque agent were prepared with (153-C) or without (153-A) the bulk-incorporated surface polymer (PAA) according to the process of Example 14. A 6F polyurethane catheter (Bard POWER PICC, 6F Dual-Lumen) was used as a control. Each sample was cut to 10 cm in length with an N=6 per sample group. Prior to testing, samples were sterilized with ethylene oxide using a 12-hour cycle; samples were also hydrated for approximately 12 hours in deionized water (lot BCBP7797V, Sigma-Aldrich). Platelets were radioactively labeled using Indium-111. Samples were inserted into an in vitro blood flow loop of ⅛ inch polyvinyl chloride tubing for approximately 60 minutes. Blood was kept at 98° F. with and a constant pressure was maintained using a peristaltic pump for the duration of testing. Samples were qualitatively assessed for thrombi (see Table 13 and FIG. 22 showing results of experiments (EXP) 1-6, with FIG. 22 showing results of experiment 6. Samples were quantitatively evaluated for platelet levels via gamma counts (Table 14). Based on the irradiated platelet counts, the porous solid PVA tubing with the bulk incorporated PAA agent showed an 89% reduction compared to the standard polyurethane control.

TABLE 13

Summary of Nonthrombogenic Durability Testing

| sample | Exp 1 | Exp 2 | Exp 3 | Exp4 | Exp 5 | Exp 6 |
|---|---|---|---|---|---|---|
| BARD Control | Little thrombus accumulation along sample | Platelet accumulation along entire length of sample | Sporadic platelet coverage along length of sample with particularly heavy coverage at distal end | Thrombus accumulation near proximal end of sample; appears to be fibrin with potentially some platelet clumping | Some thrombus accumulation at distal end of sample; mostly fibrin, with slightly platelet aggregation | Slight platelet accumulation along length of sample |
| PVA-bismuth (153-A) | Uniform thrombus accumulation (mostly fibrin, some platelet) along middle and distal ends of sample; thrombus also observed at proximal end of sample, though mostly on one side of sample; still considered uniform coverage | Uniform thrombus accumulation; both platelet with some fibrin | Mix of fibrin with platelet accumulation along length of sample; in general coverage is quite uniform along sample | Fibrin coverage along entire length of sample; several section appear to have slightly less coverage, but in general should be considered uniform coverage with some platelet aggregation from middle to distal ends | Fibrin accumulation along full length of sample with slight platelet clumping in sections along sample; accumulation appears to have occurred along edge that was closest to tubing wall; may have been exacerbated by turbulence of blood along that side; not major defects noted here (ie. lines along sample) | Fibrin thrombus along length of sample; some areas appear to have less thrombus than others, but in general accumulation is mostly uniform |
| PVA-bismuth-pAA (153-C) | Three small dots of light thrombus near end of middle and distal end of sample; unclear what type of thrombus, potentially platelet | No visible thrombus along length of sample except for slight accumulation at proximal end; most likely platelets, but difficult to determine | No thrombus accumulation along length of sample; a few small dots of light thrombus accumulation | No thrombus on sample; potentially very light area of platelet accumulation at distal end, but thrombus is very light; proximal end has very small bit of fibrin | Slight thrombus accumulation proximal at end of sample; no other visible fibrin or platelet clumping along length | No visible thrombus accumulation |

TABLE 14

Indium-111 Counts for 6 In-Vitro Blood Loop Experiments

| Exp. No. | Bard Control | 153-A | 153-C | Average Response per Loop |
|---|---|---|---|---|
| 1 | 105 | 1336 | 314 | 9468 |
| 2 | 4520 | 10301 | 244 | 19324 |
| 3 | 9349 | 17148 | 234 | 19478 |
| 4 | 210 | 2655 | 230 | 4548 |

TABLE 14-continued

Indium-111 Counts for 6 In-Vitro Blood Loop Experiments

| Exp. No. | Bard Control | 153-A | 153-C | Average Response per Loop |
|---|---|---|---|---|
| 5 | 122 | 1061 | 205 | 4720 |
| 6 | 170 | 996 | 368 | 2558.5 |
| Average | 2413 | 5583 | 266 | 10016 |
| Std. Dev. | 3821 | 6695 | 62 | 7617 |

Example 16: Surface Morphology

Scanning Electron Microscopy (SEM) of samples described in Example 14 containing PVA with RO agent (FIG. 23A at 500×, FIG. 23B at 2000×) and PVA with RO agent soaked in PAA (FIG. 24A at 300× and FIG. 24B at 2500×). The surface of the PVA with RO agent extrudate shown in FIG. 23 shows a non-porous surface with large ridges throughout the surface, the ridges being an artifact of an early extrusion process used to manufacture these samples. The surface of the PVA with RO agent soaked in PAA shown in FIGS. 24A-B shows a distinctly different surface, with significantly greater porosity on the surface, evident of the bulk incorporation altering the surface characteristics of the PVA with RO agent extrudate.

Example 17: Role of Molecular Weight of Bulk-Incorporated Surface-Bound Polymers on Thrombus Reduction Batching of PVA-Bismuth Subcarbonate Polymer Solution and Extrusion A PVA-Bismuth Subcarbonate polymer solution was prepared using 42 g Bismuth Subcarbonate (Lot: Foster, FEI5577), 179 g of 0.6 w/w % monobasic sodium phosphate solution, and Poly(vinyl alcohol) 28-99 (lot: EMD, K45556756). Substituents were heated to 67° C. in a sealed polypropylene jar and mixed in a dual asymmetric centrifugal (DAC) Flaktech SPEEDMIXER until visually homogenous.

Polymer was immediately placed on a roller at approximately 70 RPM for 4 hours. When polymer had cooled to room temperature, it was cut into 1 cm×1 cm×1 cm cubes. Cubed polymer was extruded using a Brabender ¾" single screw Advance Torque Rheometer (ATR). Heated polymer was extruded into approximately 10° C. ethanol bath onto a 0.031" acetal core filament to form tubes. The extruded material (extrudate), measuring 1.75 mm on die exit, was cut to 24" to 30" segments. After approximately 3 hours of dehydration in ethanol, monofilament was removed. Extrusions were then dehydrated to less than 5% water content in room temperature (21° C.) ethanol for 24 hours, with an OD of 1.4 mm with a 0.79 mm ID.

The extruded 4 Fr Single Lumen PVA Tubes were then cut to 10 cm and loaded with 1% poly(acrylic acid) in 5×PBS solution at varying molecular weights at 37° C. for 16 hours. Molecular weights included: 100 kDa (Sigma Aldrich: 523925), 250 kDa (Sigma Aldrich: 416002), and 710 kDa (Lubrizol: CARBOPOL 907, 710 kDa). The tubes were heat treated: dried for 3 hours at 55° C. and annealed for 90 minutes at 140° C. Upon hydrating for 24 hours in 1×PBS the tubes measuring 1.2-1.25 mm OD with roughly a 0.78 mm ID were tested in an in vitro blood flow loop as described in Example 15, where the output is platelet count (Thrombodyne). FIG. 25A shows no significant difference in thrombus accumulation as a function of molecular weight of the poly(acrylic acid) increases when compared to a control (at 100%) (CR Bard: POWERPICC 4 Fr, Single Lumen). Thrombus reduction of at least 70% was obtained.

Figure 26A:
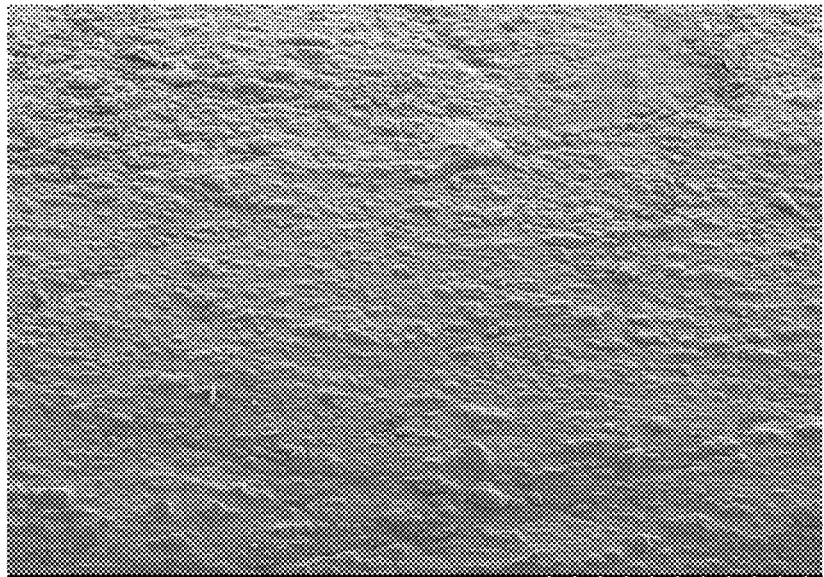
FIGS. 26A-26B are SEM micrographs of a surface of a porous solid with bulk incorporated water soluble PVA polymer (28-99) prepared according to Example 20 at 200× magnification (26A) or 2500× magnification (26B).
Figure 26B:
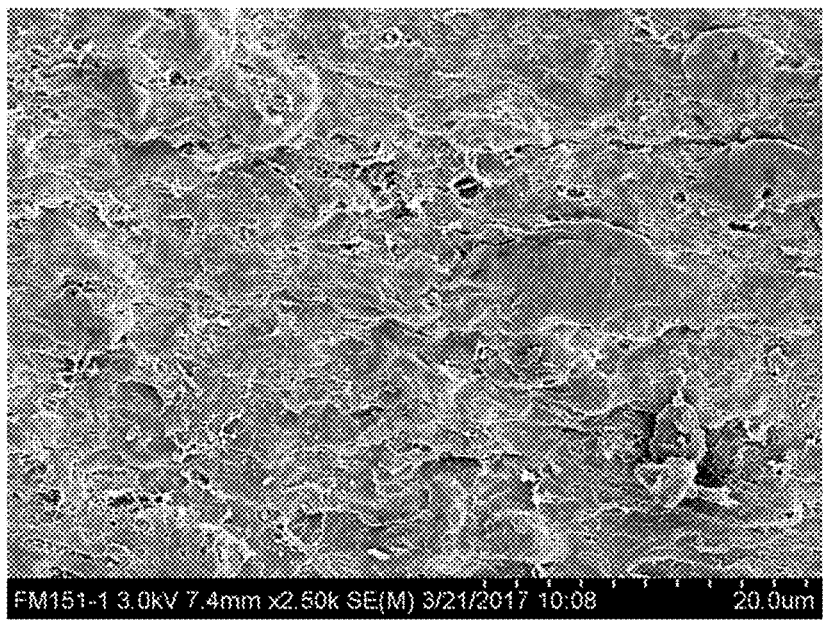

Example 18: Effect of Bulk Incorporated Surface-Bound Polymers Over Time in Blood Loop Thrombogenicity Test Extruded 4 F Single Lumen PVA Tubes described in Example 17 were cut to 10 cm and loaded with 1% poly (acrylic acid) (Lubrizol: CARBOPOL 907, Mw 710 kDa) in 5×PBS solution at 37 C The tubes were heat treated: dried for 3 hours at 55° C. and annealed for 90 minutes at 140° C. After hydrating for 24 hours in 1×PBS the tubes were tested in an in vitro blood flow loop as described in Example 17, where the output is platelet count (Thrombodyne). The time of exposure was 3 hours, 16 hours, and 40 hours. FIG. 26B shows a decrease in thrombus accumulation as exposure time of the Extruded 4 Fr Single Lumen PVA Tubes to poly(acrylic acid) increases when compared to a control (at 100%) (CR Bard: POWERPICC 4 Fr, Single Lumen). Thrombus reduction of up to 93% was obtained.

Example 19: Effect of Varying Water-Soluble Polymers Molecular Weight and Polymer Type Used as Bulk Incorporated Surface-Bound Polymers in Porous Tubes Extruded 4 F Single Lumen PVA Tubes described in Example 17 were cut to 10 cm and soaked in 1% w/w of varying polymers in 5×PBS solutions at varying molecular weights at 37° C. for 3 hours. Polymers used were: 200 kDa Poly(ethylene oxide) (PEO) (Sigma Aldrich: 181994), 360 kDa Poly(vinyl pyrrolidone) (PVP) (Sigma Aldrich: PVP360), and 710 kDa Poly(acrylic acid) (PAA) (Lubrizol: CARBOPOL 907). The tubes were heat treated: dried for 3 hours at 55° C. and annealed for 90 minutes at 140° C. Upon hydrating for 24 hours in 1×PBS the tubes were tested in an in vitro blood flow loop following the procedures of Example 17, where the output is platelet count (Thrombodyne). FIG. 26C shows a decrease in thrombus accumulation with each bulk incorporated polymer as compared to a control (at 100%) (CR Bard: POWERPICC 4 Fr, Single Lumen). Reduction of at least 30% was obtained.

Example 20: Batching of PVA-Bismuth Subcarbonate Polymer Solution and Extrusion Extruded 4 F Single Lumen PVA Tubes, manufactured under similar conditions to Example 17 except using a 0.039" acetal core filament, were cut to 24" to 30" segments. After approximately 3 hours dehydration in ethanol, monofilament was removed and PTFE covered stainless steel mandrels were inserted into lumens. Extrusions were then dehydrated in room temperature (21° C.) ethanol for 24 hours.

A 1% PVA 28-99 Solution was prepared using 2.5 g PVA 28-99 (lot: EMD, K4555675628, Mw 145 kDa) and 247.5 g 1×PBS. Solution was heated to 90° C. and mixed until solids fully dissolved. A 1% PVA 67-99 Solution was prepared using 2.5 g PVA 67-99 (lot: SEKISUI, 02812328S1. Mw 180 kDa) and 247.5 g 1×PBS. The solution was heated to 90° C. and mixed until solids fully dissolved. A 1% PAA 100 k solution was prepared using 1.905 g PAA 100 k (lot: Sigma, STBF3673V, Mw=100 kDa), 31.76 g distilled water and 33 g 10×PBS. The solution was heated to 90° C. and mixed until solids fully dissolved. A 1% PAA 250 k solution was prepared using 1.905 g PAA 250 k (lot: Sigma, STBF3186V, Mw=250 kDa), 31.76 g distilled water and 33 g 10×PBS. The solution was heated to 90° C. and mixed until solids fully dissolved. A 1% CARBOPOL 907 solution was prepared using 2.5 g PAA (CARBOPOL 907, lot: Lubrizol, 010164597, Mw=710 kDa), 495.0 g USP water (lot: Fisher, 1607174) and 495.0 g 10×PBS. The solution was heated to 90° C. and mixed until solids fully dissolved.

Extruded materials were soaked in each of the solutions described for 16 hours or 40 hours at 37° C. with or without circulation as indicated in Table 15.

TABLE 15

Soaking parameters of hydrophilic samples

| Lot # | Solution Type | Soak Time (hours) | Soak Temp | Circulating (Y/N) |
|---|---|---|---|---|
| FM012-151-1 | 1% PVA 28-99 | 16 | 37° C. | N |
| FM012-151-2 | 1% PVA 67-99 | 16 | 37° C. | N |
| FM012-151-3 | 1% PAA 100 k | 16 | 37° C. | N |
| FM012-151-4 | 1% PAA 250 k | 16 | 37° C. | N |
| DD010-121-A | 1% Carbopol 907 | 40 | 37° C. | Y |
| DD010-128-2 | 1% Carbopol 907 | 16 | 37° C. | Y |

Samples were removed from the soak after the indicated period and mounted on stainless steel mandrels. Samples were then placed inside oven, ramped to 55° C., and heated for 3 hours at 55° C. The dried samples were then annealed in air at 140° C. for 1.5 hours on mandrels in a forced air oven. Samples were then hydrated in PBS at room temperature (approximately 21° C. for 3 hours).

SEM Preparation

All samples, after annealing, were hydrated for at 3 hours in 1×PBS at 37° C. Samples were gently rinsed with distilled water and then lyophilized. Lyophilized samples were coated with 5 nm platinum prior to SEM analysis.

Analysis

FM012-151-1. PVA 28-99 soaked samples were evenly covered along the outside of the tube body, with a globular coating of PVA on the surface; no porosity was visible (see FIGS. 26A and 26B) depicting the outer surface of PVA 28-99 conditioned sample. At 200× (26A) or 2500× (31B), the outer surface appeared globular and bumpy in appearance relative to non-bulk incorporating PVA extruded porous solids (compare to FIG. 16-17 or 20), demonstrating the bulk incorporation to the surface.

Figure 27A:
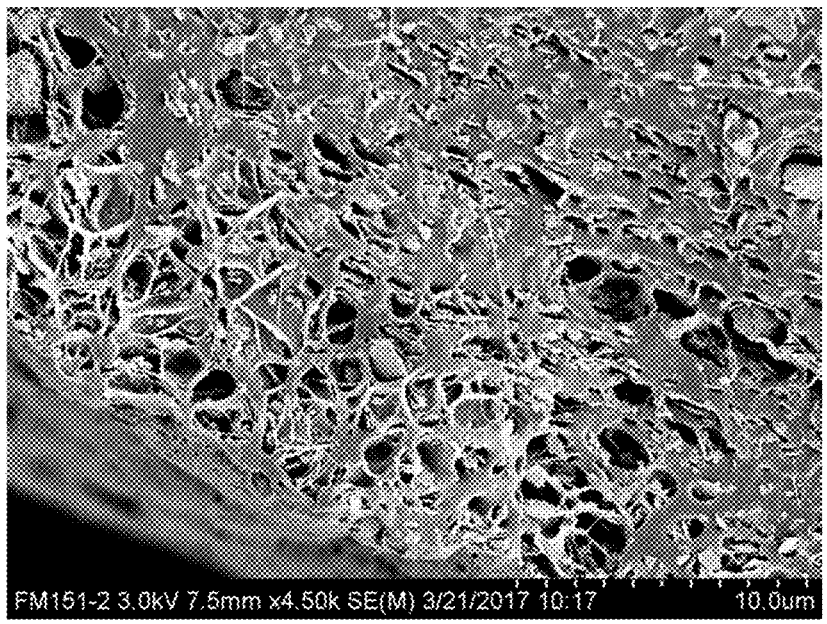
FIGS. 27A-27B are SEM micrographs of a porous solid with bulk incorporated water soluble PVA polymer (67-99) prepared according to Example 20 at 200× magnification (32A, surface view) or 2500× magnification (surface view, 27B).
Figure 27B:
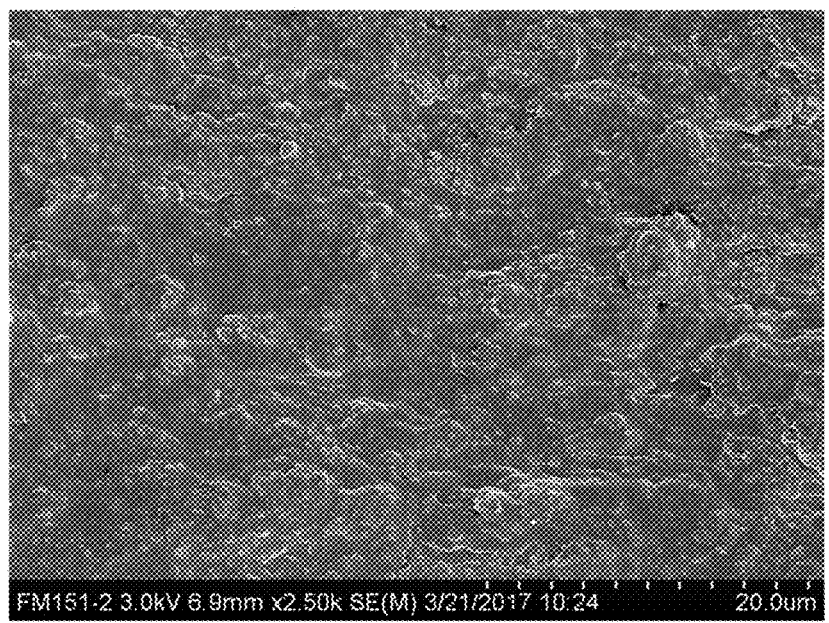
Figure 28:
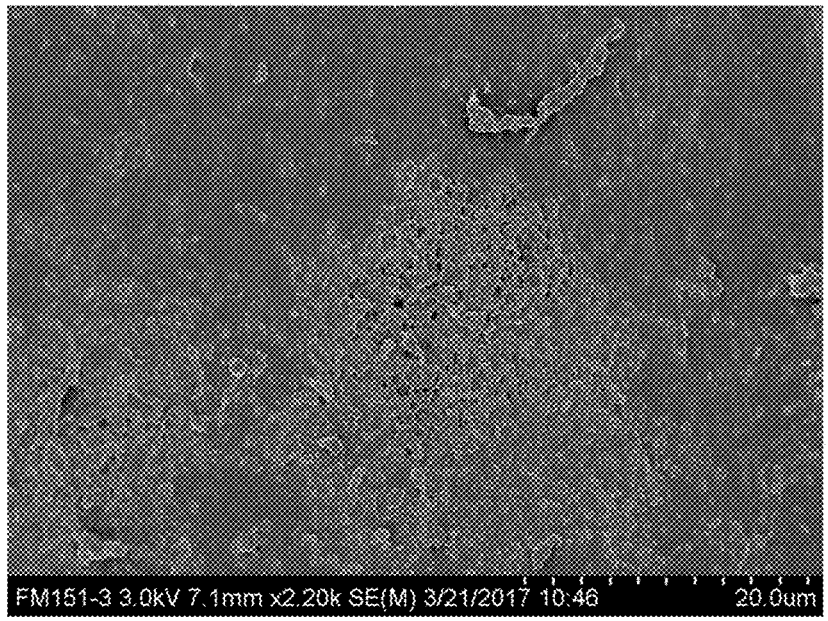
FIG. 28 is a SEM micrograph of a surface view of a porous solid with bulk incorporated water-soluble polymer (PAA, 100 k MW) prepared according to Example 20 at 2200× magnification.

FM012-151-2. Samples conditioned with PVA 67-99 shown in FIG. 27A shows the highly porous cross section near the outer surface of with web-like strands, forming a boundary layer of pores towards the outside surface of the tube body. The web-like chains decrease towards the inner wall, apparently where PVA could not penetrate. The surface again shows a globular appearance relative to the non-bulk incorporated PVA extruded porous solids (refer previous patent art). FIG. 27B is a SEM micrograph of the outer surface, showing complete coverage of the porous surface with the bulk-incorporated water soluble PVA polymer.

FM012-151-3. Samples with bulk incorporated water-soluble polymer (PAA 100 k) showed a complete coverage of the underlying porous solid, with no visible pores. The coverage was globular in some areas, supporting bulk incorporation into the surface relative to PVA extruded porous solids not exposed to bulk incorporation. In other areas, coverage was smooth and continuous although particles of bismuth subcarbonate were slightly visible below a thin layer of the PAA 100 k (see FIG. 28).

Figure 29:
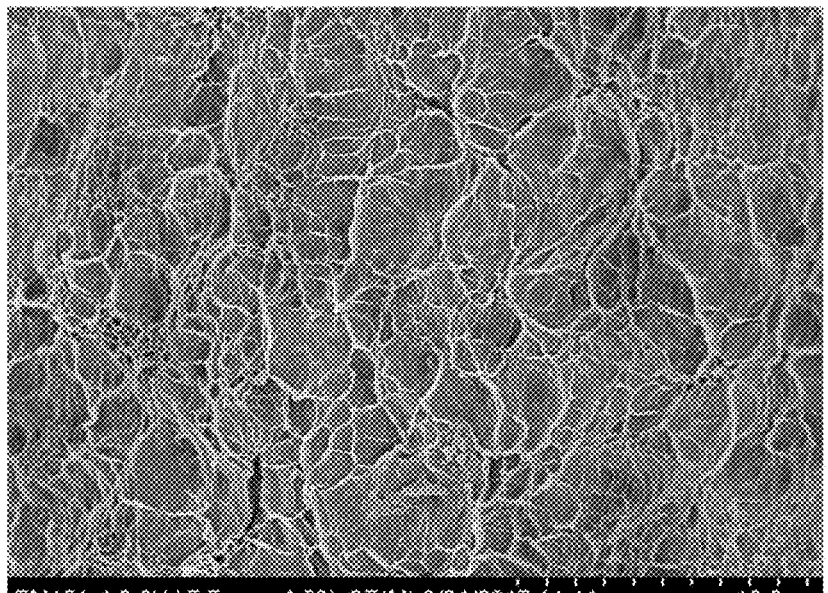
FIG. 29 is a SEM micrograph of a surface view of a porous solid with bulk incorporated water-soluble polymer (PAA, 250 k MW) prepared according to Example 20 at 4500× magnification.
Figure 30:
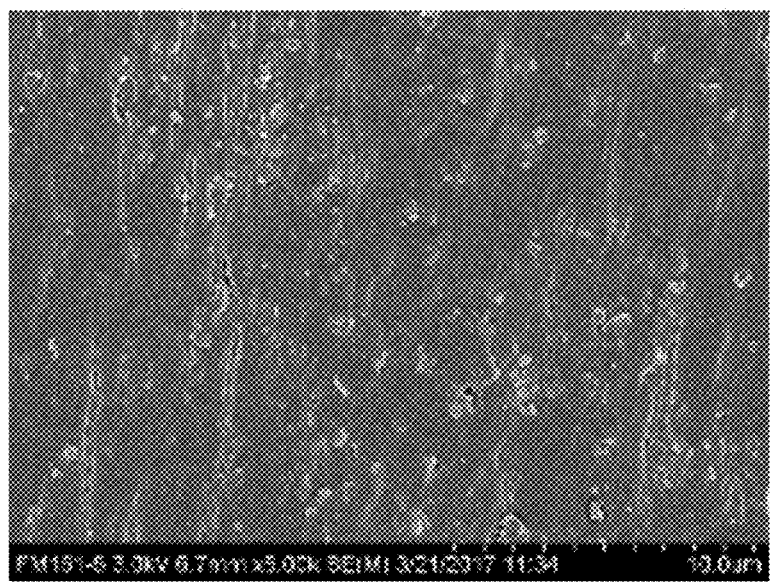
FIG. 30 is a SEM micrograph of a cross-sectional view of a porous solid with conditioned with CARBOPOL 907 prepared according to Example 20 at 5000× magnification.
Figure 31:
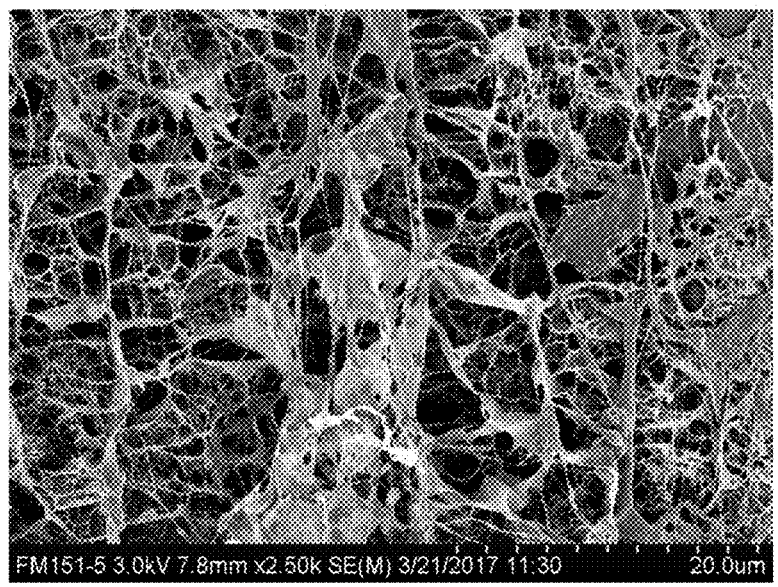
FIG. 31 is a SEM micrograph of a surface view of a porous solid with conditioned with CARBOPOL 907 prepared according to Example 20 at 2500× magnification.

FM012-151-4. Samples with bulk incorporated higher molecular weight PAA (250 k) exhibited a rougher surface than PAA 100 k conditioned samples. The entire outer surface of the tube showed continuous coverage, with the "yarn-like" features being visible, indicating bulk incorporation of the PAA as compared to non-bulk incorporated PVA extruded porous solids (refer previous patent art). FIG. 29 shows a thicker level of poly(acrylic acid) coverage on FM151-4 ((250 k PAA) than FM151-3 (100 k PAA).

DD010-121-A. Samples conditioned in CARBOPOL 907 for 40 hours (see FIG. 30) still showed some level of visible bismuth subcarbonate on cross-section, but appear very dense, with less porosity as compared to non-bulk incorporated PVA extruded porous solids. The outer surface of DD010-121-A shows a large concentration of "yarn-like" strands completely covering the surface. The surface morphology of DD010-121-A 40-hour soak (see FIG. 31) is similar to that observed in 16 hour soaked CARBOPOL 907 samples, with the "yarn-like" surface indicative of bulk incorporation of the CARBOPOL 907 as compared to PVA extruded porous solids not exposed to bulk incorporation of PAA. While there appears to be more "yarn" on 40 hour soaked samples, no tests were performed to support that conclusion.

DD010-128-2. Samples conditioned in CARBOPOL 907 for 16 hours showed little to no difference compared to the 40 hour samples (see FIG. 32).

Example 21: pSBMA Bulk Incorporated

Extruded 4 F Single Lumen PVA Tubes, manufactured under conditions as in Example 17 except using a 0.039" acetal core filament, were cut to 24" to 30" segments. Extrusions were then dehydrated in room temperature (21° C.) ethanol for 24 hours. The cut segments were removed from the ethanol, then decored to remove the filament.

Poly(sulfobetaine methacrylate) (pSBMA) was made via free radical aqueous polymerization. 0.4121 g Sulfobetaine methacrylate (Sigma Aldrich: 537284) was polymerized with 0.2316 μg of potassium persulfate (Sigma Aldrich: MKBW9558V) in 19.9693 g of USP water (RICCA: 9190). The mixture was dissolved with the aid of a vortexer. The solution was purged with nitrogen (Airgas: NI-150) for 5 minutes and sealed. It was heated to 70° C. for 16 hours. 19.7784 g of the polymerized solution was then added to 28.021 g of 1× phosphate buffered saline (FM012-173) in a 50 mL conical tube.

The dehydrated 4 Fr, extruded polyvinyl alcohol (PVA)—bismuth subcarbonate porous solid tubes were cut to 10 cm length segments and placed in the pSBMA solution for 16 hours at 37° C. The tubes were taken out of the solution, dried at 55° C. for 3 hours, and then annealed at 150° C. for 90 minutes. They were placed in 1× phosphate buffered saline for 1 hour and dried again for 3 hours at 55° C.

Figure 32:
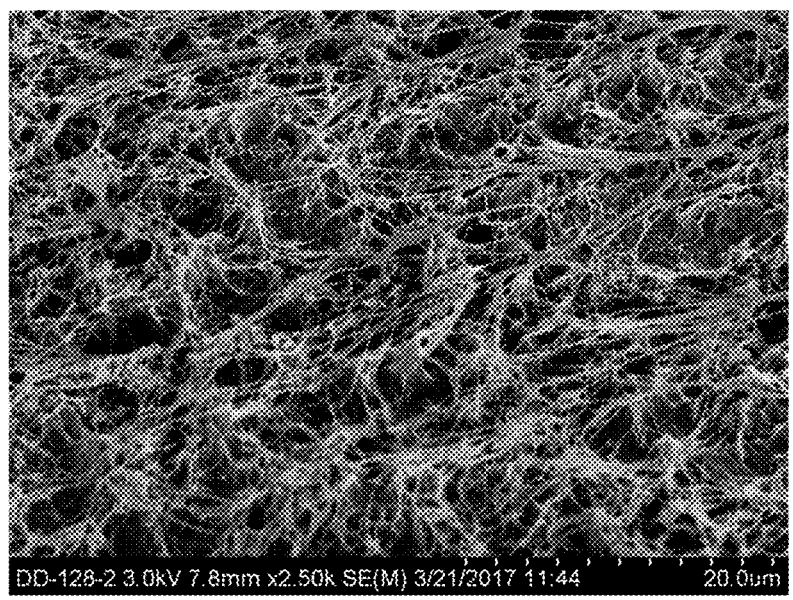
FIG. 32 is a SEM micrograph of a surface view of a porous solid with conditioned with CARBOPOL 907 prepared according to Example 20 at 2500× magnification.

FTIR was performed on the samples, shown in FIG. 32. The top spectra shows the annealed bulk incorporated p(SBMA) PVA porous solid tube. The middle spectra provides the control reference spectra for SBMA, and the bottom spectra is the control spectra for an annealed non-bulk incorporated PVA porous solid tube control. Comparing the annealed p(SBMA) bulk incorporated tube FTIR spectra (FIG. 33A) to that of control PVA-bismuth subcarbonate FTIR spectra (FIG. 33B) shows a distinct peak at 1040 cm$^{-1}$, associated with the sulfite group of SBMA (FIG.

Figure 33A:
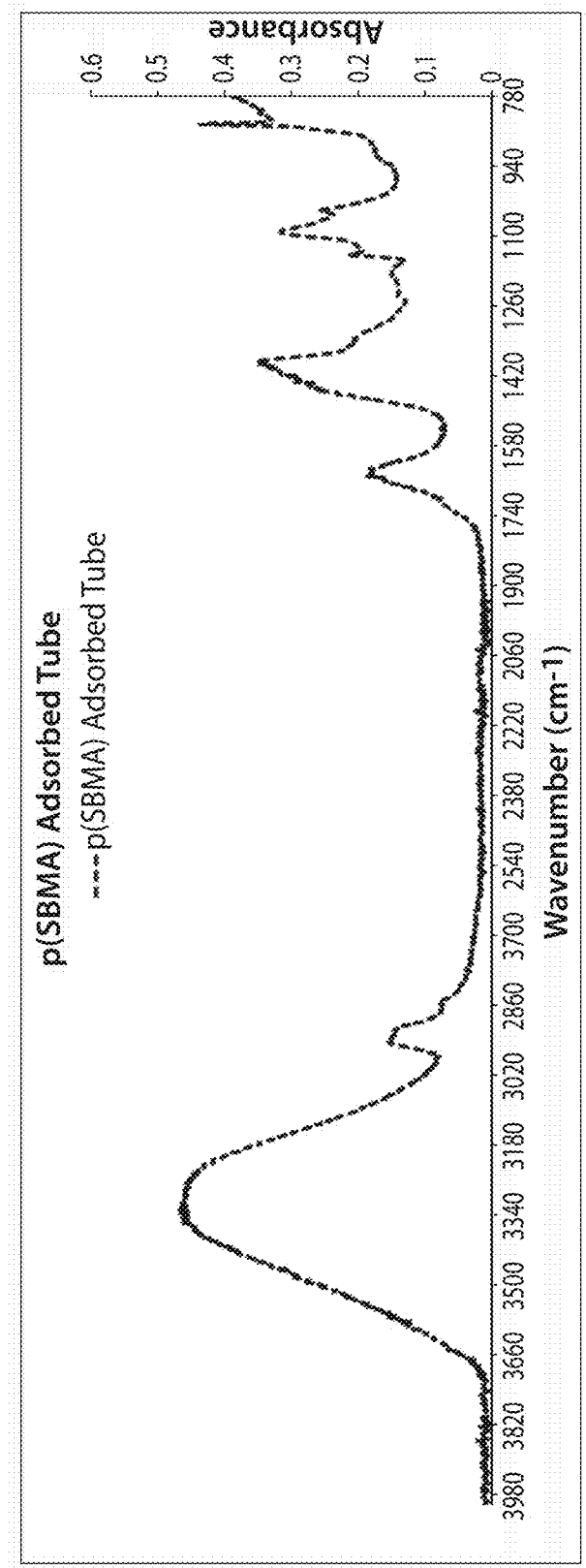
FIGS. 33A-33C are plots of FTIR data generated according to Example 21.
Figure 33B:
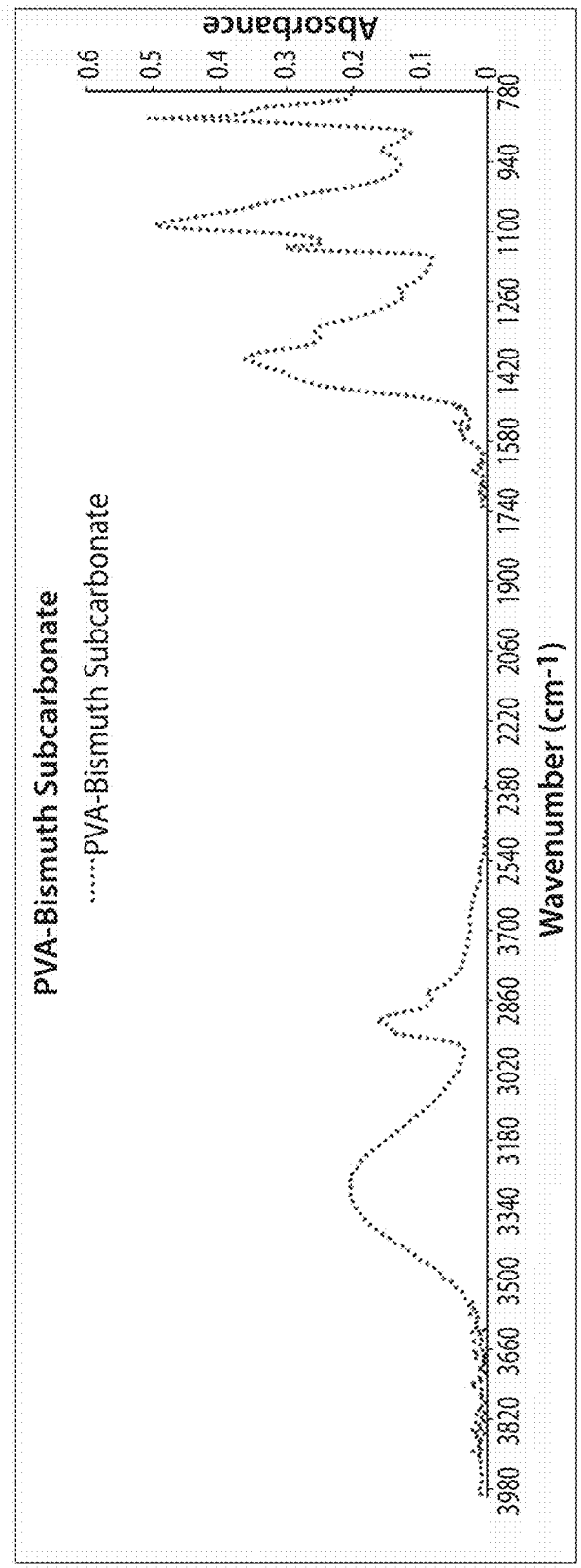
Figure 33C:
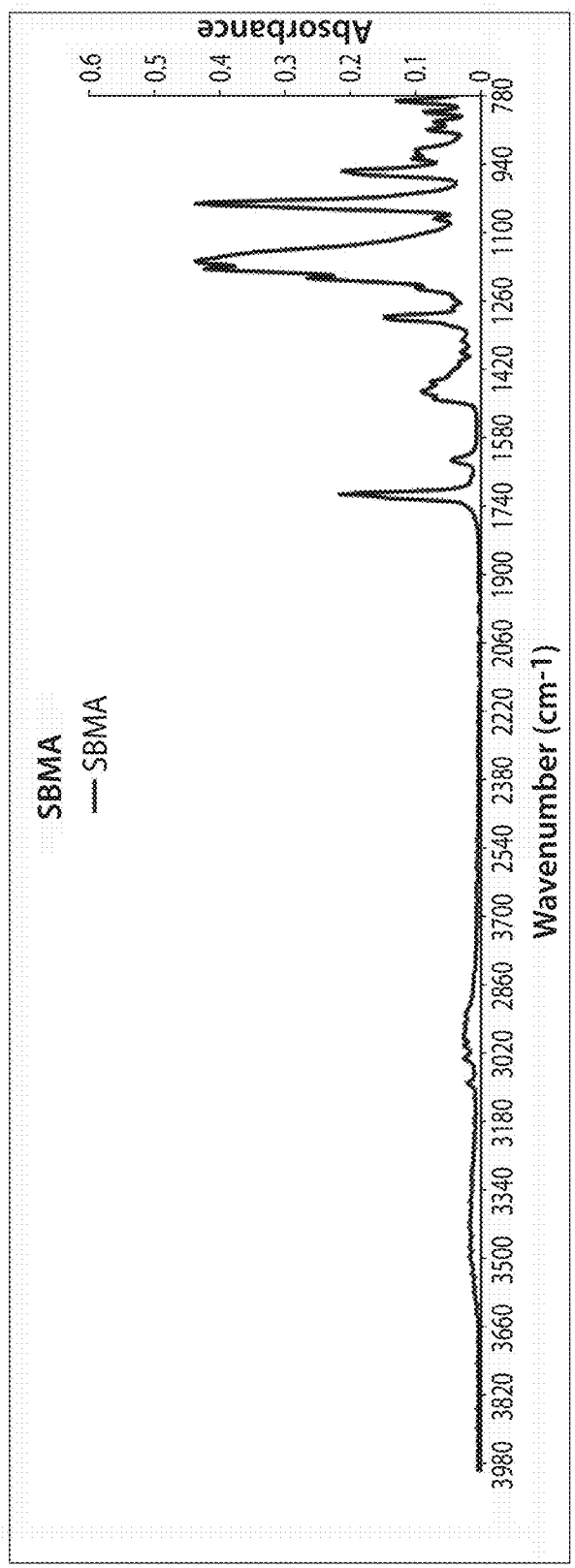

33C). This indicates the p(SBMA) has been bulk incorporated into the porous PVA-bismuth subcarbonate solid. The control sample, PVA-Bismuth Subcarbonate (FIG. 33B), has a strong PVA-associated peak at 1080 cm$^{-1}$, but no peak at 1040 cm$^{-1}$. The result of a bulk incorporated pSBMA PVA porous solid tube is a decrease in the 1080 cm$^{-1}$ peak as seen in FIG. 33A. pSBMA was successfully bulk incorporated into a PVA matrix.

Example 22: PAA Durability

Figure 34A:
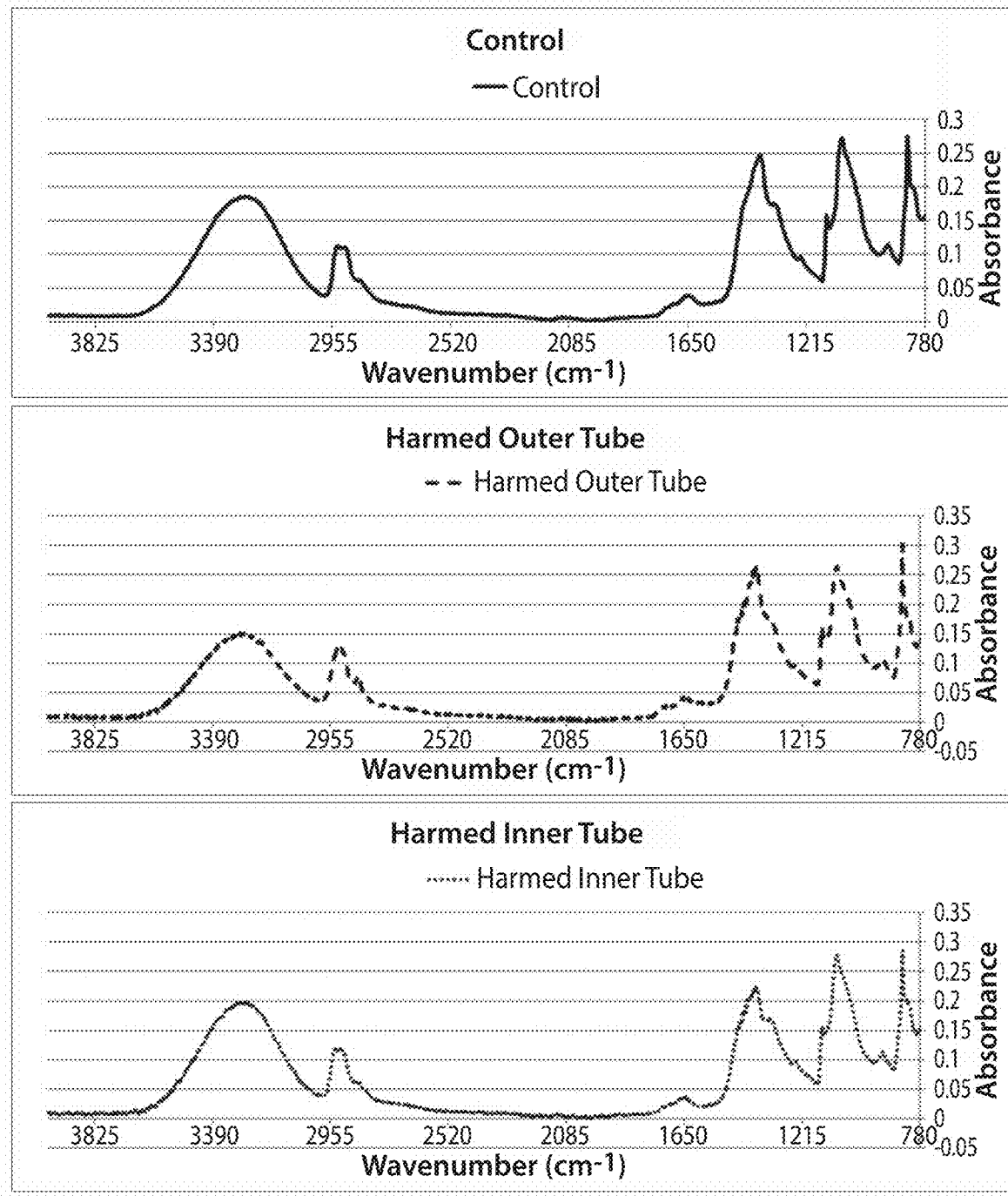
FIGS. 34A-34C are plots of FTIR data generated according to Example 22, showing control and test samples (34A), an overlay of the spectra (34B) and a magnification (34C) of the region 1500 to 1600 $cm^{-1}$ of FIG. 34B.
Figure 34B:
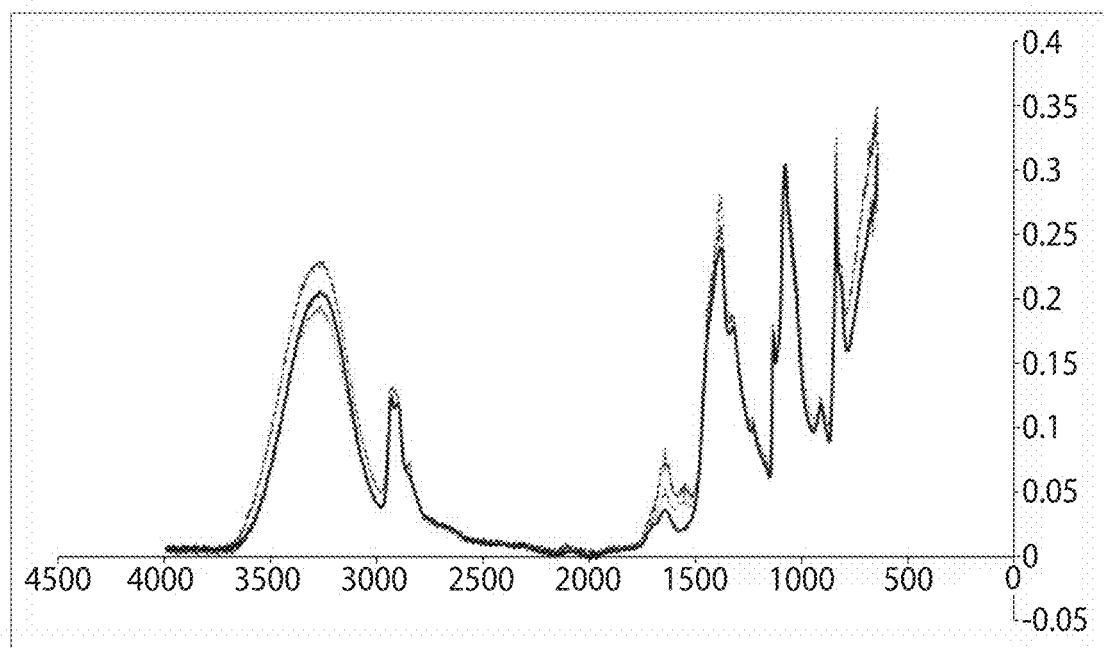
Figure 34C:
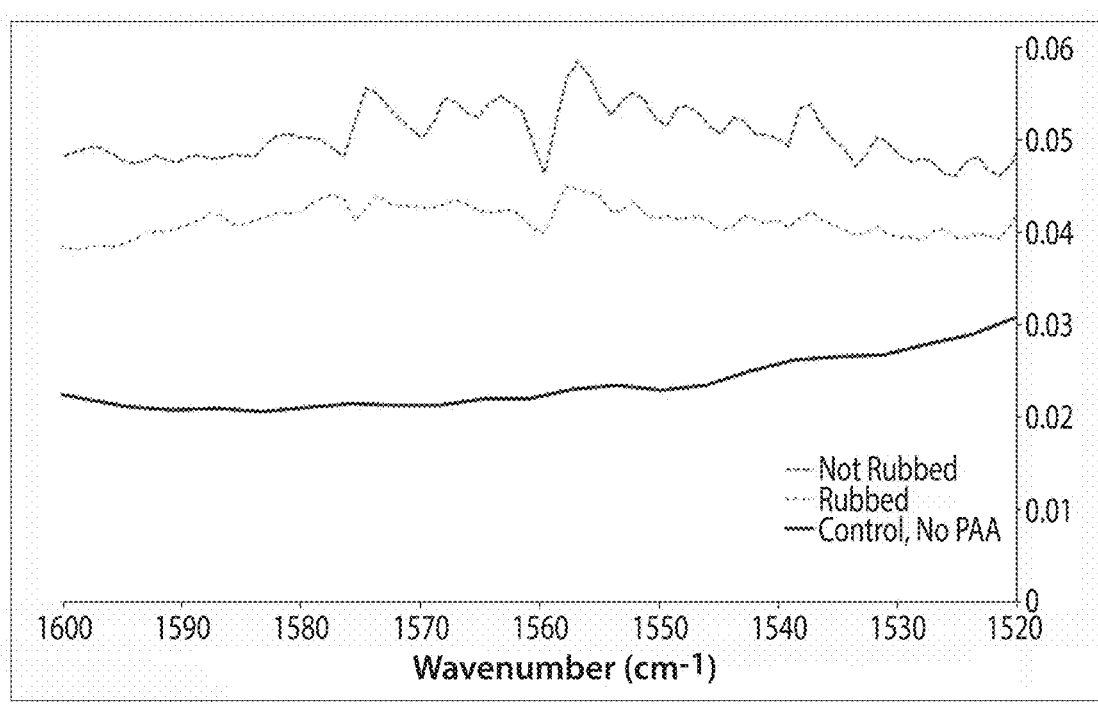

A 1% w/w solution of poly(acrylic acid) (PAA) (Lubrizol: CARBOPOL 907), in a 50:50 solution of 10× phosphate buffered saline (DD010-148) and USP water (RICCA: 9190) was made. Extruded 4 F Single Lumen PVA Tubes were made using the conditions of Example 17 except using a 0.039" acetal core filament. The tubes were cut into 24" to 30" segments. Extrusions were then dehydrated in room temperature (21° C.) ethanol for 24 hours. The cut segments were removed from the ethanol, and then decored to remove the filament. The segments were then cut to 10 cm lengths and placed in the PAA solution for 16 hours at 37° C. They were removed from the solution, dried 55° C. for 3 hours, annealed at 150° C. for 90 min, hydrated for 1 hour in 1×PBS, dried again for 3 hours at 55° C. Samples were set aside for controls or for further treatment by use in a peristaltic pump, with the treated samples being referred to as harmed tubes. A 40 cm finished tube was placed in a 40 cm neoprene tube connected in a loop with a dual barb connection. The 0.25" ID tube was filled with 1×PBS and the PAA treated PVA tube was allowed to hydrate for 2 hours at 37° C. The PAA treated PVA and neoprene tubing was place in a peristaltic pump for 24 hours at ambient conditions. The pump was set to 120 rpm and PBS was circulated through the loop, with the sample directly in the peristaltic pump head to expose it equally to flow, rubbing and compression, approximating 500,000 compressions at a flow rate of about 11 mL/s (66 mL/min) or a total of 95 L. The tubing inner diameter (ID) was 0.25" with a length of 45 cm, having an inner surface area of 89.8 cm$^2$ and a volumetric flux of 0.12 cm$^3$ s$^{-1}$ cm$^{-2}$ (11/89.8). Upon comparing the FTIR in FIG. 34A of an unharmed surface catheter (Control, not exposed to compressions) to the outer and inner surfaces of the harmed section there was no significant difference in the 1650 cm-peak, representing the acid group of the PAA. There was also no significant difference in the other peaks between 1600 cm$^{-1}$ and 780 cm$^{-1}$, indicating the PVA: bismuth subcarbonate ratio did not change as well. An overlay of the FTIR spectra is shown in FIG. 34B. A zoom in of the 1500 to 1600 cm$^{-1}$ region is shown in FIG. 34C. The peak at 1558 cm$^{-1}$, associated with the sodium acrylate peak, was used to determine the amount of PAA pre and post exposure durability exposure. The signal strength prior to rubbing and flow was 0.05183, while the signal strength after rubbing and flow was 0.04484. Accounting for baseline signal strength of 0.02299 in the control sample, a loss of only 25% was observed after exposure to these conditions. This demonstrated that the bulk incorporation of the second hydrophilic polymer to the solid porous PVA extrusion was durable.

Example 23: Role of Desolvation in Bulk Incorporation of Polymers

Extruded 4 F Single Lumen PVA Tubes, manufactured under similar conditions to Example 17 except using a 0.039" acetal core filament, were cut to 24" to 30" segments. Extrusions were then dehydrated in room temperature (21° C.) ethanol for 24 hours. The cut segments were removed from the ethanol, then decored to remove the filament. Samples were separated into two groups.

Samples of extruded, dehydrated PVA tube were soaked in a 1% solution of PAA (Lubrizol: CARBOPOL 907, Mw=710 kDa) and 5×PBS at 37° C. for 16 hours. The tube was then dried at 55° C. for 3 hours and annealed at 150° C. for 90 minutes. SEM images are shown in FIG. 35A. The arrow is outside the outer surface of the tube.

Samples of extruded, dehydrated PVA tube were dried at 55° C. for 3 hours and annealed at 150° C. for 90 minutes. Samples were then soaked in a 1% solution of PAA (Lubrizol: CARBOPOL 907) and 5×PBS at 37° C. for 16 hours. After the PAA soak the exposed tube is re-dried at 55° C. for 3 hours and re-annealed at 150° C. for 90 minutes. SEM images are shown in FIG. 35B.

Example 24: Bulk Incorporation Effects Demonstrated by Changes in Physical Properties Extruded 4 F Single Lumen PVA Tubes, manufactured under similar conditions to Example 17 except using a 0.039" acetal core filament, were cut to 24" to 30" segments. Extrusions were then dehydrated in room temperature (21° C.) ethanol for 24 hours. The cut segments were removed from the ethanol, then decored to remove the filament. Samples were separated into two groups.

Samples of extruded, dehydrated PVA tube were soaked in a 1% solution of PAA (Lubrizol: Carbopol 907, Mw=710 kDa) and 5×PBS at 37° C. for 16 hours. The tube was then dried at 55° C. for 3 hours and annealed at 150° C. for 90 minutes. These were tested for maximum load at break using a INSTRON tensile tester (Model 3343, 500 N load cell) with pneumatic grips @40 psi and a grip strength of 1 kN. Samples were pulled at 400 mm/min starting from a 20 mm gap distance, and tensile strength and modulus calculated for samples. Samples of bulk incorporated hydrophilic PVA tubes were compared to non-bulk incorporated controls that had undergone identical drying and annealing conditions.

Table 16 shows results for max load at break, Young's Modulus, and the normalized tensile. Table 17 provides the calculated area per sample based on the measured ID and OD of the tubes. P values for significant differences between PAA bulk incorporated and control samples are calculated. It is evident that no significant difference between OD and ID is evident, though area was significant. Max load at break, modulus, elongation and normalized tensile were all significant. This indicates that the methods detailed result in bulk incorporation of the second hydrophilic into the existing porous PVA matrix, as they occupy the pores of the matrix prior to annealing and alter the overall mechanical properties of said matrix. A true surface coating would not alter the mechanical strength of the base porous PVA solid.

TABLE 16

|  | Lot Number |  | Maximum (N) Load |  | Young's (MPa) Modulus |  | Normalized (MPa) Tensile |
|---|---|---|---|---|---|---|---|
| PAA | DD010-148 | 26.98<br>25.85<br>24.56 | 25.8 ± 1.2 | 17.95<br>16.18<br>11.50 | 15.21 ± 3.3 | 31.26<br>32.12<br>25.08 | 29.49 ± 3.8 |
| No PAA | FM012-159-2c | 28.81<br>27.86<br>28.36 | 28.35 ± 0.5 | 26.27<br>25.07<br>24.76 | 25.37 ± 0.8 | 59.08<br>47.42<br>38.62 | 48.37 ± 10.3 |
|  | p-value |  | 0.027 |  | 0.007 |  | 0.041 |

TABLE 17

|  | Area (mm^2) |  | Outer Diameter (mm) |  | Inner diameter (mm) |  | Elongation (%) |  |
|---|---|---|---|---|---|---|---|---|
| PAA | 0.93<br>0.90<br>0.99 | 0.94 ± 0.047 | 1.464<br>1.45<br>1.51 | 1.47 ± 0 | 0.98<br>0.98<br>1.01 | 0.99 ± 0.017 | 981.038<br>928.541<br>974.47 | 961.35 ± 28.6 |
| No PAA | 0.70<br>0.77<br>0.86 | 0.77 ± 0.08 | 1.36<br>1.42<br>1.46 | 1.41 ± 0.1 | 0.98<br>1.02<br>1.02 | 1.01 ± 0.023 | 1089.302<br>1072.898<br>1000.717 | 1054.31 ± 47.1 |
|  | p-value | 0.037 |  | 0.148 |  | 0.374 |  | 0.043 |

Example 25: Extrudate Hydration Rate

The following example demonstrates the hydration rate for an exemplary extruded PVA tube using 0.039" acetal core filament.

A PVA-Bismuth Subcarbonate polymer solution (e.g., a first water soluble polymer) was prepared using 42.0 g Bismuth Subcarbonate (Lot: Foster, FEI5577), 179.25 g of 6.2 w/w % monobasic sodium phosphate solution, and Poly(vinyl alcohol) 28-99 (lot: EMD, K45556756). Substituents were heated in a sealed polypropylene jar and mixed in a Flaktech Speedmixer.

The polymer was immediately placed on a roller at approximately 70 RPM for 4 hours. When the polymer had cooled to room temperature, it was cut into 1 cm×1 cm×1 cm cubes.

The cubed polymer was extruded using the Brabender ¾" single screw ATR. Heated polymer was extruded into approximately 10° C. ethanol bath onto a 0.039" acetal core filament. The extruded PVA tubes (extrudate) were cut to 24" to 30" segments. After approximately 3 hours of dehydration in ethanol, the core filament was removed and PTFE covered stainless steel mandrels were inserted into lumens.

A hydrophilic solution was prepared using Carbopol 907 (lot: Lubrizol, 010164597), USP water (lot: Fisher, 1607174) and PBS. The solution was heated and mixed until solids fully dissolved.

All samples were soaked for 16 hours at 37° C. in Carbopol 907 solution in stainless steel circulatory baths.

Samples were removed from soak after indicated period and mounted on stainless steel mandrels. Dried samples were then annealed in air at 140° C. for 1.5 hours on mandrels in a forced air oven. Samples were then hydrated in PBS at room temperature (approximately 21° C. for 3 hours). After hydrating, samples were dried back down at 37° C. for 5 hours.

Dry samples were cut into approximately 20 mm long sections. Length, inner diameter, outer diameter, and mass were recorded for each sample. Samples were then submerged in 1×PBS at room temperature (approximately 21-22° C.). A syringe was used to ensure that all air was expelled from lumens.

At various time intervals, samples were removed from PBS, dabbed lightly on a lint-free lab wipe to remove excess PBS from lumen and surface; length and mass were recorded and samples were quickly returned to PBS. Samples were hydrated for a total of 22 hours. Inner and outer diameters were measured again after 1 hour and 22 hours of hydration.

Length, mass and inner diameter (ID)/outer diameter (OD) percent change were calculated using to following formula:

$$\% \text{ change} = \frac{(\text{final value} - \text{initial value})}{\text{initial value}} * 100$$

Percent change for each variable was averaged for each time point (see Table 18).

TABLE 18

| Time (min) | Avg. % Mass | Stdev % Mass | Avg. % Length | Stdev % Length | Avg. % ID Change | Stdev % ID Change | Avg. % OD Change | Stdev % OD Change |
|---|---|---|---|---|---|---|---|---|
| 0 | 0.0 | 0.0 | 0.0 | 0.0 | 0.0 | 0.0 | 0.0 | 0.0 |
| 2.5 | 30.6 | 12.4 | 2.9 | 0.3 | x | x | x | x |
| 5 | 32.4 | 11.3 | 4.5 | 0.6 | x | x | x | x |
| 10 | 30.5 | 4.1 | 6.3 | 1.0 | x | x | x | x |
| 15 | 26.2 | 4.9 | 7.9 | 1.1 | x | x | x | x |
| 20 | 22.9 | 11.1 | 7.4 | 1.0 | x | x | x | x |
| 25 | 35.5 | 10.5 | 6.6 | 0.8 | x | x | x | x |

TABLE 18-continued

| Time (min) | Avg. % Mass | Stdev % Mass | Avg. % Length | Stdev % Length | Avg. % ID Change | Stdev % ID Change | Avg. % OD Change | Stdev % OD Change |
|---|---|---|---|---|---|---|---|---|
| 35 | 31.7 | 13.0 | 7.0 | 1.1 | x | x | x | x |
| 45 | 33.3 | 26.1 | 7.4 | 1.1 | x | x | x | x |
| 60 | 24.4 | 15.5 | 7.3 | 0.5 | 18.0 | 4.2 | 2.7 | 4.8 |
| 120 | 29.5 | 4.6 | 7.5 | 0.9 | x | x | x | x |
| 1320 | 26.4 | 4.3 | 6.8 | 0.3 | 18.8 | 3.5 | 4.9 | 2.2 |

During hydration, percent increase in mass fluctuated slightly between 22.9% to 33.3% over the 22-hour hydration period but showed no significant difference in mass increase between any time point.

Percent increase of sample length showed tight standard deviations as compared to mass increase and serve as a representative indicator of level of sample hydration. Length increased 2.9% and 4.5% after 2.5 and 5 minutes of hydration, respectively; length increase then leveled off at approximately 10 minutes of hydration, with no significant increase in length after that point (see Table 18).

Inner and outer diameter showed 4.9% and 18.8% increase at 60 min and 1320 min, respectively. Without wishing to be bound by theory, the significant difference between ID and OD may be due to the fact that ID shrinkage is restricted by the size of the core diameter during ethanol dehydration, drying and annealing, causing the ID to retain more of its initial sizing, whereas OD is unrestricted during post extrusion processing, and therefore able to swell more when hydrated. OD showed no significant change between 1 and 22 hours of hydration.

4F catheters extruded on 0.039" core filament show no further length increase after 10 minutes of hydration in 1×PBS at 21° C.

Example 26: Strength Testing of Dehydrated Articles

The following example demonstrates the properties of articles, according to some embodiments described herein.

22 articles/catheters (e.g., a first component as described above) integrated with suture wings (e.g., a second component as described above) were used during the study. The length was first measured using a calibrated measuring tape and measured from distal tip to the proximal suture wing.

The catheter tube (e.g., an article comprising a first water soluble polymer as described above) was cut 5 cm distal from the suture wing. These were tested for maximum load at break using an INSTRON tensile tester (Model 3343, 500 N load cell) with pneumatic grips @40 psi and a grip strength of 1 kN. Samples were pulled at 400 mm/min starting from a 20 mm gap distance, and tensile strength and modulus calculated for samples. Separately, the bond strength of the suture wing and extension leg joint was tested. The cross section of a 1-2 mm piece of the distal tip from the catheter body was measured. The modulus, strain, and absolute tensile force were measured. Stress is generally defined as tensile force over cross-sectional area according to:

$$\text{Stress}\left[\frac{N}{mm^2}\right] = \frac{\text{Tensile Force}[N]}{\text{Cross Sectional Area}[mm^2]}$$

Modulus is generally defined as the maximum slope of stress over % elongation (strain) according to:

$$\text{Modulus}\left[\frac{N}{mm^2} = MPa\right] = \frac{\Delta\text{Stress}[N/mm^2]}{\Delta\text{Elongation}[\%]}$$

The slope is generally defined as the ratio of change in stress over change in strain. Young's modulus was measured between 0% and 10% elongation. A typical break of a dehydrated PVA tube would occur at less than 50% elongation. A break was determined as a 40% drop in tensile from the maximum value.

Suture Wing to Tube Joint

A break was often detected (40% drop in tensile from maximum load) before the 50% elongation. Where a break wasn't detected, stable necking of the dry PVA tube occurred. The maximum tensile strength of 22 samples was 53 N (Table 19). All breaks were observed within the PVA tube. Some of the PVA tube breaks occurred inside the suture wing, but were not complete slip outs, the mechanical bond from the heat shrink and hypotubes alongside the aliphatic polyether-based thermoplastic polyurethane dip coats and continued to hold a segment of the dehydrated PVA tube.

TABLE 19

| | Maximum Tensile |
|---|---|
| Average | 53N |
| Lower Tolerance Limit (k = 2.118) | 45N |
| Standard Deviation | ±4N |
| Standard Error | ±1N |
| % RSD | 8% |

The tensile strength of the catheter body was also evaluated. The results are summarized in Table 20. Samples used for this testing were post-sterilization.

TABLE 20

Dehydrated PVA Tube Dimensions and Strength characteristics. (n = 22)

| | Maximum Load (N) | Young's Modulus (MPa) | Stress (MPa) | Area (mm²) | OD (mm) | ID (mm) |
|---|---|---|---|---|---|---|
| Average | 55 | 1844 | 151 | 0.61 | 1.19 | 0.80 |
| Lower Tolerance Limit (k = 2.118) | 47 | 1509 | 113 | 0.53 | 1.13 | 0.74 |
| Standard Deviation | ±4 | ±158 | ±18 | ±0.04 | ±0.03 | ±0.03 |
| Standard Error (n = 22) | ±1 | ±34 | ±4 | ±0.01 | ±0.01 | ±0.01 |
| % RSD | 7% | 9% | 12% | 6% | 3% | 4% |

Example 27: Hydration Testing

The following example demonstrates the hydration profile of an exemplary article/catheter, as described herein.

20 articles/catheters (e.g., articles comprising a first water soluble polymer as described herein) were prepared as described in Example 24. The final product was packaged in protective sheaths in 12×18" Tyvek/mylar pouches and sterilized by ethylene oxide.

Samples were removed from their protective sheath and a mass measurement was taken prior to any preparation or additional conditioning. Samples were then hydrated by flushing the catheter with 5 mL of normal saline at 22±2° C. After 10 minutes, a mass measurement was taken. The catheters were then transferred to a 1×PBS bath at 37±2° C. Additional mass measurements were taken at 30 minutes, 60 minutes, 90 minutes, 120 minutes, 3 hours, 4 hours and 24 hours submersed in 1×PBS at 37±2° C. Results of mass were used to define the range of observation for inner lumen diameter.

Samples were evaluated for inner lumen diameter at 4 data points: a) dry, b) 10 minutes at 22±2° C., c) 20 minutes at 37±2° C. and d) when the sample reached steady state 37±2° C.

Mass

The percent mass increase from the dry state and after the 10-minute, 22±2° C. hydration and exposure to in situ conditions (37° C., PBS) is summarized in Table 21.

TABLE 21

| Timepoint | Average (g) | Mass Standard Deviation (g) | Average % Mass Increase From Dry | Average % Mass Increase after 10-minute Hydration |
|---|---|---|---|---|
| Dry | 3.40 | 0.022 | N/A | N/A |
| 10-minute | 3.55 | 0.040 | 4.5%* | N/A |
| 30-minute | 3.63 | 0.026 | 6.6% | 1.9% |
| 60-minute | 3.65 | 0.026 | 7.3% | 2.8% |
| 90-minute | 3.65 | 0.027 | 7.1% | 2.6% |
| 120-minute | 3.66 | 0.031 | 7.4% | 3.0% |
| 180-minute | 3.66 | 0.022 | 7.5% | 3.0% |
| 240-minute | 3.69 | 0.043 | 8.4% | 4.0% |
| 1440-minute | 3.68 | 0.019 | 8.0% | 3.5% |
| Average at Steady | | | | |

During the initial hydration at 10 minutes at 22° C., samples increased in mass by 4.5% with a standard deviation of 0.9%. Samples increased in mass by an average 3.1% with a standard deviation of 0.9% between 10 minutes and steady state, which results in an average total mass increase of 7.7% with a standard deviation of 1.0% overall.

Note that some timepoints appear to lose mass when compared to the previous timepoint but is believed due to the error in the measurement. Although a standard process for removing excess water prior to gravimetric measurement was employed during this study, it is possible that water in the lumen or on the surface of the catheter varied between timepoints.

To determine what was considered steady state, a t-test was conducted between consecutive timepoints assuming 2 tails and unequal variance. The results can be found in Table 22.

TABLE 22

| Timepoint Comparison | P-value |
|---|---|
| 10 minutes to 30 minutes | 0.00 |
| 30 minutes to 60 minutes | 0.05 |
| 60 minutes to 90 minutes | 0.67 |
| 90 minutes to 120 minutes | 0.49 |
| 120 minutes to 180 minutes | 0.79 |
| 180 minutes to 240 minutes | 0.07 |
| 240 minutes to 1440 minutes | 0.41 |

As shown in Table 22, the first timepoint where the populations are not statistically different (p-value>0.05) between consecutive timepoints is 60 minutes. This generally indicates the time at which the catheter reaches the hydration steady state.

Based on the results of the mass study, the steady state timepoint used for this study was 60 minutes. The average inner diameter per timepoint is reported in Table 23.

TABLE 23

| Timepoint | Average Inner Diameter (mm) | Standard Deviation (mm) |
|---|---|---|
| As packaged | 0.78 | 0.020 |
| 10 minutes | 0.87 | 0.014 |
| 20 minutes | 0.89 | 0.027 |
| 60 minutes | 0.89 | 0.018 |

The measured hydrated inner diameter is 0.90±0.10 mm. Based on these results, after hydration at 22±2° C. for 10 minutes, all catheters are within the specification with an average of 0.87 mm. A t-test was done between the inner diameter at 20 minutes and 60 minutes and assuming 2 tails and unequal variance, the p-value is 0.58, showing there is no significant difference between the inner diameter at 20 minutes (the earliest potential first point of use for injection of infusate) and steady state.

This study shows that at 10 minutes the catheter assembly is at 93% of its full mass and the ID is 0.87 mm, which is within the desired range for a 4 Fr catheter. This results in an ID that is acceptable for injection of infusate at the time of insertion and is further supported by the ID measurements taken at 20 minutes which found an ID of 0.89 mm. Based on the results of the mass study, samples reach full hydration at 60 minutes, which results in an average mass increase of 3% from the mass after the 10-minute hydration.

Example 28: Blood Loop Analysis

The following example demonstrates the quantitative thrombogenicity of extruded PVA tubes (e.g., articles comprising a first water soluble polymer as described herein) relative to existing commercial standard and non-thrombogenic devices (BioFlo PICC by AngioDynamics and PowerPICC® by Bard).

A PVA-Bismuth Subcarbonate polymer solution (e.g., a first water soluble polymer) was prepared using 42.0 g Bismuth Subcarbonate (Lot: Foster, FEI5577), 179.25 g of 6.2 wt % monobasic sodium phosphate solution, and Poly (vinyl alcohol) 28-99 (lot: EMD, K45556756). Substituents were heated to in a sealed polypropylene jar and mixed in a Flacktek Speedmixer.

After mixing, polymer was immediately placed on a roller at approximately 70 RPM for 4 hours. When polymer had cooled to room temperature, it was cut into 1 cm×1 cm×1 cm cubes.

Cubed polymer was extruded using the Brabender ¾" single screw ATR. Heated polymer was extruded into a 10±2° C. ethanol bath onto a 0.039" acetal core filament. The extruded PVA tubes were cut to approximately 60 mm to 75 mm segments. After 3 hours dehydration in ethanol and core filament was removed.

All samples were soaked for 16 hours at 37° C. in a 1% Carbopol 907 solution in stainless steel circulatory baths, ensuring steady solution flow through lumen.

Samples were removed from soak after indicated period and mounted on PTFE coated stainless steel mandrels. Dried samples were annealed in air at 140° C. for 1.5 hours in a forced air oven.

A 20% Poloxamer 407 solution was prepared using 401.27 g Poloxamer 407 (lot: Spectrum, 1FK0656), 160.97 g 10×PBS (lot: Sigma, SLBQ7746V), and 1641.00 g of USP water (lot: RICCA, 1607174). After annealing, samples were conditioned in the 20% Poloxamer 407 at room temperature (approximately 21° C.) for three (3) hours. After conditioning, samples were rinsed with USP water and immediately bagged in Tyvek pouches; samples were doubled bagged.

Samples were sterilized in an Anprolene Sterilizer with 18.2 g of ethylene oxide in a 24 hour exposure cycle.

These samples were labeled as DD010-132-A. Four (4) separate comparative catheters, 4F PowerPICC®s and 4F BioFlo PICCs, were obtained.

DD010-132-1 samples were measured to determine outer diameter dimensions after full hydration. Samples were hydrated for in PBS for approximately 16 hours at 37° C. and cut into 15 cm lengths. Outer diameter was measured at four points along length of 15 cm long sample. Outer diameter measurement points were spaced approximately 3-4 cm apart.

Nonthrombogenic durability testing was performed where samples were hydrated in sterile saline for approximately 24 hours prior to testing; any sample longer than 15 cm once fully hydrated was trimmed to length prior to mounting in blood loop. Full length PowerPICC and BioFlo devices were cut into 15 cm lengths; tapered sections of these devices were not used for blood loop testing.

Fresh bovine blood was collected and heparin was added to achieve a 0.75 U/ml concentration. Platelets were labeled with 111Indium. Samples were inserted into an in-vitro blood flow loop of ¼ inch (6.4 mm) polyvinyl chloride tubing for approximately 120 minutes. Blood was kept at 37° C. and pumped at 200 ml/min through the loop using a peristaltic pump for the duration of testing. Samples were initially checked for thrombi after 45 minutes in the blood flow loop, and removed after 60-120 minutes. Six replications (N=6) were run in total with two samples of each catheter type per experiment.

Samples were first assessed qualitatively for specific types of thrombus accumulation (i.e. platelet adhesion and/or fibrin accumulation). Radiation counts per minute (CPM) of were determined for each sample and are summarized in Table 24.

TABLE 24

|  | PowerPICC (Control) Average (CPM) | BioFlo Average (CPM) | DD010-132-A Average (CPM) |
| --- | --- | --- | --- |
| Experiment #1 | 1195.5 | 168.5 | 47 |
| Experiment #2 | 1162.5 | 205.5 | 96.5 |
| Experiment #3 | 3210.5 | 2197 | 92.5 |
| Experiment #4 | 22107.5 | 44.5 | 24.5 |
| Experiment #5 | 27989.5 | 1733 | 241.5 |
| Experiment #6 | 17523.5 | 1478.5 | 494.5 |
| Average | 12198.2 | 971.2 | 166.1 |
| Standard Error | 4828.9 | 384.3 | 72.6 |

DD010-132-A outer diameter after hydration was an average of 1.47±0.04 mm for N=24 points (a total of 3 measurements were made on each of 6 retain samples from the same lot as the devices tested).

Overall, extended blood loop analysis against PowerPICC® (control device) and BioFlo devices showed a significant decrease in thrombus accumulation on the DD0101-132-A as compared to both comparative catheters. Visually, all six (6) experiments showed reduced thrombus accumulation on DD010-132-A samples, which showed little to no visual platelet adherence (see FIG. 36) while both the PowerPICC® control and BioFlo devices showed obvious signs of moderate to severe platelet accumulation.

Figure 36:
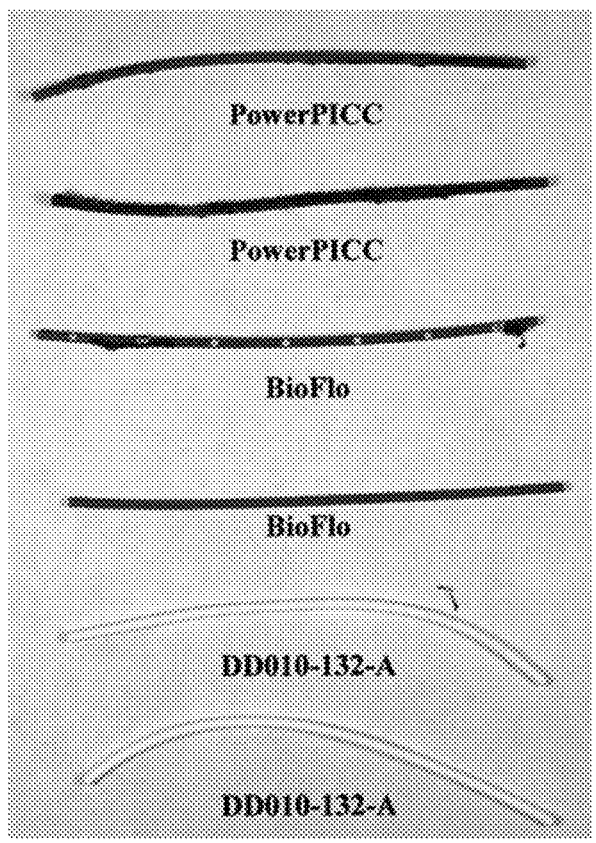
FIG. 36 is a photograph of an exemplary thrombogenicity test.

In experiments where fibrin accumulation was observed, the comparative devices showed moderate (BioFlo) to severe (PowerPICC®) platelet accumulation where the DD010-132-A samples did not (see FIG. 36).

Radiation counts showed a similarly large distinction between both comparative devices and DD010-132-A devices. In general, both PowerPICC® and Bioflo showed high levels of CPM variability, even between samples in the same experiments, as opposed to DD010-132-A devices which had average CPMs that remained relatively low and had tight tolerances (see Table 24).

Using PowerPICC® as a baseline for 100% thrombus accumulation, BioFlo showed average platelet accumulation of 19.2%±10.2%, an 80.8% relative reduction as compared to PowerPICC. The PICC-141 showed platelet accumulation of 3.2%±1.2%, a 96.8% decrease in relative thrombus accumulation compared to the PowerPICC® (see Table 24 and FIG. 36). Using BioFlo as a baseline for 100% thrombus accumulation, DD010-132-A shows an average decrease in relative thrombus of 69.8% (see Tables 24-25).

TABLE 25

| | CPM Percent Comparison versus PowerPICC Control Device (%) | | |
| --- | --- | --- | --- |
| Exp | PowerPICC ® (Control) | BioFlo | DD010-132-A |
| 1 | 100.0 | 14.1 | 3.9 |
| 2 | 100.0 | 17.7 | 8.3 |
| 3 | 100.0 | 68.4 | 2.9 |
| 4 | 100.0 | 0.2 | 0.1 |
| 5 | 100.0 | 6.2 | 0.9 |
| 6 | 100.0 | 8.4 | 2.8 |
| Avg | 100.0 ± 0.0 | 19.2 ± 10.2 | 3.2 ± 1.2 |

DD010-132-A outperformed comparative devices during in-vitro blood loop testing with decreased thrombus accumulation on device body, as well as decreased variability across N=6 replications. DD010-132-A devices showed a 96.8% reduction in thrombosis as compared to PowerPICC® and 69.8% reduction as compared to BioFlo.

EXEMPLARY EMBODIMENTS

1. A process for making a porous solid material comprising heating a mixture (also referred to as a matrix-forming mixture) that comprises at least one water soluble polymer (also referred to as a matrix polymer or matrix-forming polymer) and a solvent (also referred to as polymer-forming solvent) to a temperature above the melting point of the at least one polymer in the polymer-solvent mixture and cooling the mixture in a solvent-removing environment to physically crosslink the polymer to make a crosslinked matrix, and continuing to remove the solvent until the crosslinked matrix is a microporous solid material or until it is a nanoporous solid material.

2A. A process for making a porous solid material comprising heating a (matrix-forming) mixture that comprises at least one water soluble (matrix-forming) polymer and a (matrix-forming) solvent to a temperature above the melting point of the at last one polymer in the (matrix-forming) mixture, forming the mixture, e.g., by molding or extruding the mixture through a die, and passing the formed mixture into a solvent-removing environment. The process may further comprise one or more of: e.g., cooling the formed mixture in a solvent-removing environment, and continuing to remove the solvent until the crosslinked matrix is a nanoporous solid material or until it is a microporous solid material.

2B. A process comprising solvating, in a mixture, a pre-desolvated hydrophilic structural matrix that comprises one or more hydrophilic polymers physically crosslinked form a porous matrix, with the mixture having one or more water soluble polymers that resolvates the porous hydrophilic porous matrix. The matrix may further be annealed.

3. A process for making a porous polymeric material and/or hydrophilic porous solid comprising heating a (matrix-forming) mixture that comprises at least one (matrix-forming) water soluble polymer and a (matrix-forming) solvent to a temperature above a melting point of the (matrix-forming) polymer, forming the mixture, e.g., extruding the mixture through a die, and passing the formed mixture into a solvent-removing environment. In the case of extrusion, with the (matrix-forming) polymer forming a continuous porous solid as it passes through the die. Embodiments include removing at least 50% w/w of the solvent in less than 60 minutes (or less than 1, 2, 5, or 10 minutes). Embodiments include removing at least 90% w/w of the solvent in less than 60 minutes (or less than 1, 2, 5, or 10 minutes). Resultant materials may be, e.g., a hydrogel, a microporous material or a nanoporous material. The extrusion may be a cold extrusion.

4. The process of any of paragraphs 1-3 wherein a salt is in the mixture or is added during the process. Salts can be useful for dissolving polymers and/or to aid in crosslinking. The salt may be, e.g., anionic, cationic, divalent, trivalent. Moreover, additives that are salts or otherwise, that are capable of two or more hydrogen-bond acceptor and/or hydrogen bond donator sites may be added to the polymers.

5. The process of any of paragraphs 1-4 wherein crosslinking takes place while cooling the mixture and/or in the solvent-removing environment.

6. The process of any of paragraphs 1-5 wherein the porous solid is crosslinked with bonds that are covalent crosslinks or physical crosslinks. These embodiments include being free of covalent bonds in the case where physical crosslinks are involved.

7. The process of any of paragraphs 1-6 further comprising annealing the porous solid.

8. The process of any of paragraphs 1-7 further comprising aligning the polymer chains of the continuous porous solid to be substantially parallel to each other.

9. The process of paragraph 8 wherein aligning the polymer chains comprises passing the mixture through a die.

10. The process of any of paragraphs 1-9 wherein the at least one water soluble polymer comprises PVA, PAA, PEG, PVP-I, or PVP.

11. The process of any of paragraphs 1-10 wherein the at least one water soluble polymer comprises hydroxyl or carboxyl pendant groups.

12. The process of any of paragraphs 1-11 wherein the mixture has a concentration of the at least one polymer in the mixture from 5% to 50% w/w of the polymer relative to the mixture.

13. The process of any of paragraphs 1-11 wherein the mixture has a concentration of the at least one polymer in the mixture from 5% to 50% w/w of the polymer relative to the solvent.

14. The process of paragraph 12 wherein at least 50% of the solid material that forms the porous solid is PVA, PAA, PEG, or PVP.

15. The process of any of paragraphs 1-14 wherein the porous solid completes crosslinking while being in a solvent-removing environment.

16. The process of any of paragraphs 1-14 wherein the porous solid is prepared as a tube.

17. The process of any of paragraphs 1-15 wherein exposure to a solvent-removing environment removes at least half of the solvent in less than 60 minutes.

18. The process of any of paragraphs 1-17 comprising an exposure to a solvent-removing environment of at least one hour. For example, an exposure to the dehydrating environment during which time at least about 50% w/w of the total solvent is removed.

19. The process of any of paragraphs 1-18 wherein the porous solid has a Young's modulus of at least 5 MPa at EWC.

20. The process of any of paragraphs 1-18 wherein the porous solid has an elongation at break of at least 200%, a Young's modulus of at least 5 MPa and a tensile strength of at least 20 MPa, at EWC.

21. The process of any of paragraphs 1-20 wherein the polymeric material further comprises a second material in contact with the porous solid, e.g., the second material being a reinforcing material, a fiber, a wire, or plastic fibers.

22. The process of any of paragraphs 1-21 wherein the mixture comprises at least two polymers.

23A. The process of any of paragraphs 1-22 wherein the at least one polymer comprises a first hydrophilic polymer and a second hydrophilic polymer. For example, wherein the first and second polymers are independently chosen from PVA, PAA, PEG, PVP-I, and PVP. And/or for example wherein the first and second polymers are present at a ratio of 1 part of the second polymer and from 1-100,000 parts of the first polymer (w/w).

23B. The process of any of paragraphs 1-22 wherein the at least one polymer comprises a first polymer at a first concentration and a second polymer at a second concentration, with the first concentration being from 10%-60% w/w and the second polymer being from 1%-10% w/w, with the w/w being the weight of the polymer relative to the total weight of all of the polymers and the solvent in the mixture.

24. The process of any of paragraphs 1-23 (23 refers to 23A and 23B) wherein the mixture further comprises a salt or other additive for crosslinking.

25. The process of any of paragraphs 1-24 further comprising an additive capable of two or more hydrogen-bond acceptor and/or hydrogen bond donator sites.

26. The process of any of paragraphs 22-25 wherein at least two polymers are co-extruded, a for example two or more of: polyvinylpyrrolidone, polyvinylpyrrolidone-iodine, polyethylene glycol, and polyacrylic acid.

27. The process of paragraphs 26 wherein the coextruded polymers are mixed in a die head.

28. The process of any paragraphs of 22-26 wherein the water-soluble polymer is a first polymer that is formed into a first layer, and further comprising a second polymer formed as a second layer.

29. The process of any of paragraphs 22-28 wherein the first polymer and the second polymer are extruded at the same time as separate layers.

30. The process of any of paragraphs 28-29 wherein the first polymer layer is formed as a sheet and the second polymer layer is formed in contact with the sheet.

31. The process of any of paragraphs 1-31 further comprising adding a third polymer.

32. The process of paragraph 31 wherein the third polymer is polyvinylpyrrolidone, polyvinylpyrrolidone-iodine, PEG, or polyacrylic acid.

33. The process of any of paragraphs 21-32 wherein the second material is a reinforcing material, a fiber, a wire, a braided material, braided wire, braided plastic fibers, or at least a portion of a connector.

34. The process of any of paragraphs 21-32 further comprising the second material or the second polymer being disposed as a layer on, or within, the material.

35. The process of any of paragraphs 21-34 wherein the second polymer or the second material comprises a polyethylene glycol or a polyol, e.g., wherein the polyol is a polymer having at least three hydroxyl groups, or wherein the polyol is glycerin.

36. The process of any of paragraphs 1-35 further comprising adding braiding material in contact with the porous solid.

37. The process of any of paragraphs 1-36 wherein making the mixture comprises adding PVA to a solvent.

38. The process of any of paragraphs 1-37 wherein the solvent comprises (or consists essentially of) water, an alcohol, ethanol, an organic solvent miscible with water, or a combination thereof.

39. The process of any of paragraphs 1-38 wherein the heated solvent is at a temperature from 70 to 120° C.

40. The process of any of paragraphs 1-39 wherein a PVA concentration in the mixture is from 15% to 25% w/w.

41. The process of any of paragraphs 1-40 wherein the mixture is cooled after formation or at the time of formation and comprises passing the mixture into a cold bath, a chilled mold, a frozen mold, or liquid nitrogen.

42. The process of any of paragraphs 1-41 wherein the solvent-removal environment is a chamber filled with a gas. For example, dry air, or nitrogen, or a gas at, e.g., less than atmospheric pressure.

43. The process of any of paragraphs 1-41 wherein the solvent-removal environment is a solution that comprises ethanol, methanol, isopropanol, or a polyol.

44. The process of any of paragraphs 1-41 wherein the solvent-removal environment comprises a solution with an osmolarity that exceeds an osmolarity of the mixture.

45. The process of any of paragraphs 1-44 wherein the solvent-removal environment or solution comprises a salt present in at a concentration of at least 0.1 molar.

46. The process of any of 44-41 wherein the solvent-removal environment or solution comprises a salt present in at a concentration in a range of 0.1 to 8 molar.

47. The process of any of paragraphs 1-43 wherein the solvent-removal environment or solution further comprises an osmotic agent, with the environment having an osmolar value greater than an osmolar value of the formed mixture.

48. The process of any of paragraphs 1-47 wherein the solvent-removal process is performed over a period of time from 3 to 48 hours.

49. The process of any of paragraphs 1-48 wherein the solvent-removal process is performed while the polymer is crosslinking.

50. The process of 49 wherein the crosslinking is completed before the solvent removal process is completed.

51. The process of any of paragraphs 1-50 further comprising an annealing process that comprises heating a porous solid material to an annealing temperature.

52. The process of paragraph 51 wherein the annealing temperature is from 80 to 250° C.

53. The process of any of paragraphs 51-52 wherein the annealing is performed in an absence of air and/or oxygen and/or water.

54. The process of any of paragraphs 50-53 wherein the annealing is performed, at least in part, in a liquid bath.

55. The process of paragraph 54 wherein the liquid bath comprises mineral oil and/or a polyol and/or glycerin.

56. The process of any of paragraphs 50-55 wherein the annealing is performed for a period of time from 3 hours to one week.

57. The process of any of paragraphs 1-56 wherein the mixture is passed through a die.

58. The process of paragraph 57 wherein the mixture is formed as a tube having at least one lumen.

59. The process of paragraph 57 wherein the tube is formed around a core.

60. The process of paragraph 59 wherein the core is air, water, a liquid, a solid, or a gas.

61. The process of any of paragraphs 57-60 further comprising a second material or a second polymer being extruded as a layer on, or within, the crosslinked matrix.

62. The process of any of paragraphs 57-61 wherein the mixture is a first mixture, with the process further comprising a second mixture that comprises a further material, with the second mixture also being passed through the extrusion die to form a second tubular layer.

63. The process of paragraph 61 wherein the second material is or comprises a reinforcing material, a fiber, a wire, or plastic fibers.

64. The process of any of paragraphs 57-63 wherein a solid material surrounds the core and becomes entrapped within the tubular hydrogel layer or, when present, the second tubular layer.

65. The process of paragraph 64 wherein the solid material comprises a wire, a braid, a metal wire, a plastic wire, a metal braid, a plastic braid, a mesh, a fabric mesh, a metal mesh, a plastic mesh.

66. The process of any of paragraphs 1-65 wherein the porous solid is formed as a continuous form, a tube, a sheet, a solid cylinder, a tube with a plurality of lumens, or a ring.

67. The process of any of paragraphs 1-66 wherein the porous material is with an aspect ratio of at least 4:1 (length: diameter). Alternatively, an aspect ratio from 3:1 to 1000:1.

68. The process of any of paragraphs 1-67 wherein the porous material is hydrophilic.

69A. The process of any of paragraphs 1-68 wherein the porous material is processed to further comprise at least one bulk incorporated polymer.

69B. A biomaterial, a polymeric material, or a catheter comprising a medically acceptable hydrophilic porous solid. The solid may further comprise at least one bulk incorporated polymer.

70. A biomaterial, a polymeric material, or a catheter comprising a porous polymeric solid having one or more of: a tensile strength of at least 20 MPa, a Young's modulus of at least 5 MPa, a solids content of from 10%-50% w/w at EWC, a solids content of at least 10% w/w or at least 33% at EWC, a solids content of 10, 20, 30, 33, 35, 40, 50, 60% w/w at EWC. For example, a polymeric material comprising a hydrophilic porous solid, with the porous solid having a solids content of at least 33% w/w and a Young's modulus of at least 5 MPa, at equilibrium water content (EWC). And, for example, forming with an aspect ratio of at least 10:1. For example, a polymeric material of wherein the porous solid comprises at least one polymer, and the at least one polymer comprises a first hydrophilic polymer and a second hydrophilic polymer, with the second hydrophilic polymer being present in an amount from 1 part to 1,000 parts relative to 10,000 parts of the first polymer.

71. The biomaterial of paragraphs 69 or 70 wherein the porous polymeric solid comprises crosslinked hydrophilic polymers.

72. The biomaterial of paragraphs 70 or 71 with the porous polymeric solid having a solids content of at least 33% w/w at equilibrium water content (EWC) in a physiological saline at 37° C. Alternatively, the solids content being at least 50% w/w or in a range from 40% to 99% w/w.

73. The biomaterial of any of paragraphs 70-72 with being a nanoporous material having a tensile strength of at least 20 MPa and/or a Young's modulus of at least 5 MPa with a solids content of the nanoporous material being at least 50% w/w at EWC.

74. The biomaterial of any of paragraphs 70-73 wherein the pore diameters are 100 nm or less.

75. The biomaterial of any of paragraphs 70-74 having an internal alignment of the polymeric structure.

76. The biomaterial of any of paragraphs 70-75 with the porous material swelling no more than 50% w/w at EWC when placed in an excess of physiological saline and allowed to freely expand, with a PVA content of the hydrogel being at least 50% w/w.

77. The biomaterial of any of paragraphs 70-76 being a nanoporous material or a microporous material that comprises, or consists essentially of, at least one hydrophilic polymer, PVA, PAA, PEG, or PVP or a combination thereof.

78. The biomaterial of any of paragraphs 70-77 wherein the porous material comprises a matrix of a crosslinked hydrophilic polymer, wherein the water soluble polymer comprise hydroxyl and/or carboxyl pendant groups.

79. The biomaterial of any of paragraphs 70-78 wherein the porous material comprises crosslinked polymers having a molecular weight, before crosslinking, of at least 50 k g/mol. Alternatively, a molecular weight in g/mol from 50 k to 1000 k.

80. The biomaterial of any of paragraphs 70-79 wherein at least 50% of the solid material that forms the porous material is PVA, PAA, PEG, or PVP.

81. The biomaterial of any of paragraphs 70-80 wherein the porous material is crosslinked with covalent crosslinks or is free of covalent crosslinks and/or is free of covalent crosslinking agents.

82. The biomaterial of any of paragraphs 70-81 wherein the nanoporous material is crosslinked with physical crosslinks.

83. The biomaterial of 82 wherein the physical crosslinks are ionic bonds, hydrogen bonds, electrostatic bonds, Van Der Waals, or hydrophobic packing.

84. The biomaterial of any of paragraphs 70-83 further comprising a layer of a second material or a second polymer.

85. The biomaterial of any of paragraphs 70-83 further comprising a second material encapsulated within the porous solid.

86. The biomaterial of paragraph 85 wherein the second material is a reinforcing material, a fiber, a wire, a braided material, braided wire, braided plastic fibers, or at least a portion of a connector.

87. The biomaterial of any of paragraphs 84-86 wherein the coating or the layer or the second polymer of the second material comprises a polyethylene glycol or a polyol, e.g., wherein the polyol is a polymer having at least three hydroxyl groups, or wherein the polyol is glycerin.

88. The biomaterial of any of paragraphs 84-87 wherein the coating or the layer or the second polymer of the second material comprises PVA, PAA, PEG, or PVP.

89A. The biomaterial of any of paragraphs 70-88 further comprising a radiopaque (RO) agent. The RO agent may be, e.g., a coating, a layer on, or in the biomaterial.

90. A biomaterial of any of 70-83 that consists essentially of PVA, or a porous material consists essentially of PVA.

91. The biomaterial of any of paragraphs 70-91 comprising a shape that is a tube.

92. A process of incorporating polymers in a porous material comprising providing a desolvated porous matrix and exposing the desolvated porous matrix to a mixture comprising one or more water soluble polymers solvated in a solvent.

93. A process of incorporating polymers in a porous material comprising providing a material comprising a porous, hydrophilic matrix that comprises one or more water soluble polymers physically crosslinked with each other to form the matrix, with the matrix being desolvated, exposing the matrix to a mixture that resolvates the porous hydrophilic porous matrix and comprises one or more water soluble polymers solvated in a solvent of the mixture, and resolvating in the mixture.

94. A process of incorporating polymers in a porous material comprising
providing a material comprising a porous, hydrophilic matrix that comprises one or more water soluble polymers (also referred to as matrix polymers) physically crosslinked with each other to form the matrix, with the matrix being desolvated,
exposing the desolvated porous hydrophilic matrix to a mixture (also referred to as conditioning mixture) comprising one or more water soluble polymers (also referred to as bulk incorporated polymers or conditioning polymers) solvated in a solvent, (also referred to as bulk-forming solvent or conditioning solvent), and wherein exposing the hydrophilic matrix to the mixture draws the one or more of the water-soluble polymers into the pores. The porous hydrophilic matrix may be hydrophilic relative to the solvent.

95. The process of any of paragraphs 92-94 wherein the matrix comprises a solvent and is desolvated to between 0-90% of an EWC of the matrix in the solvent before exposure to the mixture.

96. The process of any of paragraphs 92-95 wherein the matrix is resolvated in the mixture to an EWC in the mixture.

97. The process of any of paragraphs 92-96 wherein the matrix is annealed after exposure to the mixture.

98. The process of any of paragraphs 92-97 with the desolvated matrix comprising a first composition of a solvent and the mixture comprising a second composition of a solvent. The first and second compositions may be the same or different, and may independently be chosen to be water, aqueous, organic, or a mixture of the same, with the water composition for the first and second compositions being independently chosen to be from 0-100% of the total solvent weight.

99. The process of paragraph 98 wherein the first composition and second composition are independently chosen to have 0-100% of a solvent that is methanol, ethanol, an alcohol, dimethylsulfone, or water.

100. The process of any of paragraphs 92-99 wherein the polymer of the porous matrix and the polymer of the mixture are independently selected to be one or more polymers may be selected from the group consisting of polyvinyl alcohol (PVA), polyvinylpyrrolidone (PVP), polyethylene glycol (PEG), polyacrylic acid (PAA), polyacrylamide, hydroxypropyl methacrylamide, polyoxazolines, polyphosphates, polyphosphazenes, poly(vinyl acetate), polypropylene glycol, Poly(N-isopropylacrylamide) (PNIPAM), polysaccharides, sulfonated hydrophilic polymers (e.g., sulfonated polyphenylene oxide, Nafion®, sulfobetaine methacrylate) and variations of the same with an added iodine (e.g., PVA-I, PVP-I), or variations with further pendent groups, copolymers with one or more of the same and combinations of the same. An RO agent or other materials may be present in the matrix.

101. The process of any of paragraphs 92-100 wherein exposure to the mixture causes a decrease in physical properties of the matrix. For instance, a decrease in Young's modulus and/or tensile strength that is independently selected to be from 1-20%, e.g., 1, 5, 10, or 15%. As is evident, the decrease is relative to the same process performed without exposure to the mixture, or wherein the exposure to the mixture is performed but the bulk incorporation does not proceed, e.g., the matrix is not suitably desolvated before the exposure.

102. The process of any of paragraphs 92-101 wherein a coverage by the water-soluble polymer is at least 70, 80, 90, or 100%.

103. A material comprising a porous matrix of physically crosslinked hydrophilic polymers that are crosslinked to form the matrix and to define pores of the matrix, with the matrix comprising a water-soluble polymer incorporated into the surface without covalent crosslinking to the surface. The water-soluble polymer may be, for instance, incorporated as a monolayer or present in pores of the matrix at the surface and under the surface.

104. A material conditioned with water-soluble polymers comprising a porous matrix that comprises a water-soluble polymer incorporated into a surface portion of the porous matrix without covalent bonds to the material, with no more than 25% w/w of the water-soluble polymer being removable from the surface when exposed to 500,000 compressions in a peristaltic pump flowing physiological saline across the surface at a flux of 0.12 cm$^3$ s$^{-1}$ cm$^{-2}$ for 24 hours.

105 A material comprising a porous matrix of a physically crosslinked hydrophilic polymer crosslinked to form the matrix and to define pores of the matrix, with the matrix comprising at least one water soluble polymer incorporated into a surface of the matrix without covalent crosslinking of the water soluble polymers to the surface, with the incorporated water soluble polymer providing a decrease of at least 10% of a Young's modulus of the porous matrix relative to the porous matrix in an absence of the incorporated polymer.

106. A material conditioned with water soluble polymers comprising a porous hydrophilic matrix that comprises a water-soluble polymer entrapped in pores of the porous matrix without covalent bonds to the material, wherein the porous matrix comprises a hydrophilic polymer physically crosslinked to form the hydrophilic matrix and the pores.

107. A material with bulk incorporated polymers comprising a water-soluble polymer entrapped in pores of a hydrophilic porous matrix, with the matrix comprising a physically crosslinked hydrophilic polymer.

108. A material with bulk incorporated polymers comprising a water-soluble polymer entrapped in pores of a hydrophilic porous matrix, with the matrix consisting essentially of a physically crosslinked hydrophilic polymer.

109. The material of any of paragraphs 103-108 with the water-soluble polymer covering at least a portion of a surface of the matrix.

110. The material of any of paragraphs 103-109 wherein a Young's modulus of the material is reduced by at least 10% (or 20%) by the water soluble (bulk incorporated) polymer.

111. The material of any of paragraphs 103-110 wherein the water-soluble polymer (bulk incorporated polymers) are present at the surface without providing a network.

112. The material of any of paragraphs 103-111 wherein the water-soluble polymer is essentially free of covalent bonds with each other and/or wherein, a EWC, the water-soluble polymers are essentially free of hydrogen bonds with each other.

113. The material of any of paragraphs 103-112 with the matrix being free of, or essentially free of, covalent bond cross-links and/or covalent crosslinking agents.

114. The material of any of paragraphs 103-113 wherein the matrix, at a surface of the material, has pores with openings at the surface of no more than 1 μm diameter at EWC. Alternatively, no more than 2000, 1000, 500, 250, 100 or 10 nm diameter. A percentage of the pores that are below the indicated diameter may be, e.g., 50, 60, 70, 80, 90, 95, 99, or 100% of the total pores of the surface.

115. The material of any of paragraphs 100-114 wherein the water-soluble polymer is present in at least some pores of the porous solid that are within 10 μm of a surface of the matrix. Alternatively, at any depth chosen from 1-500 μm. Alternatively, wherein the porous matrix comprises the bulk incorporated polymers at a depth of 1-500 μm.

116. The material of any of paragraphs 103-115 wherein a molecular weight of the water-soluble polymer is from 40 k-5000 k, or a range or value thereof.

117. A biomedical catheter comprising the material of any of paragraphs 70-116.

118. The catheter of paragraph 117 wherein the catheter is a central venous catheter, a peripherally inserted central catheter (PICC), a tunneled catheter, dialysis catheter. central venous, peripheral central, midline, peripheral, tunneled, dialysis access, urinary, neurological, peritoneal, intra-aortic balloon pump, diagnostic, percutaneous transluminal angioplasty, interventional, or a drug delivery catheter.

119. The catheter of any of paragraphs 117-118 comprising a plurality of lumens.

120. A biomedical catheter comprising a medically acceptable material, e.g., the material of any of paragraphs 1-118. For example, a hydrophilic nanoporous material, hydrophilic microporous material, or a hydrogel, e.g., further comprising a bulk incorporated polymer.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape-such as, round, square, gomboc, circular/circle, rectangular/rectangle, triangular/triangle, cylindrical/cylinder, elliptical/ellipse, (n) polygonal/(n) polygon, etc.; angular orientation-such as perpendicular, orthogonal, parallel, vertical, horizontal, collinear, etc.; contour and/or trajectory-such as, plane/planar, coplanar, hemispherical, semi-hemispherical, line/linear, hyperbolic, parabolic, flat, curved, straight, arcuate, sinusoidal, tangent/tangential, etc.; direction-such as, north, south, east, west, etc.; surface and/or bulk material properties and/or spatial/temporal resolution and/or distribution-such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed is:

1. An article, comprising:
a polymeric material comprising a first water soluble polymer having a plurality of pores;
a second water soluble polymer, same as the first water soluble polymer and positioned within at least a portion of the plurality of pores;
an osmotic agent present in the polymeric material, and
wherein the polymeric material has a Young's elastic modulus of greater than or equal to 500 MPa in a dehydrated state and a Young's elastic modulus of less than or equal to 300 MPa and greater than or equal to 5 MPa at an equilibrium water content state.

2. An article as in claim 1, wherein the plurality of pores have a mean pore size of less than or equal to 500 nm and greater than or equal to 10 nm.

3. An article as in claim 1, wherein at least 50% of the plurality of pores have a diameter of less than or equal to 1 μm.

4. An article as in claim 1, wherein the article has a porosity of greater than or equal to 5% and less than or equal to 50% in a dehydrated state.

5. An article as in claim 1, wherein the article is configured to swell in an amount greater than or equal to 5 w/w % and less than or equal to 50 w/w % from a dehydrated state to an equilibrium water content state.

6. An article as in claim 5, wherein swelling occurs in less than or equal to 60 minutes in water.

7. An article as in claim 5, wherein swelling occurs in less than or equal to 60 minutes in standard normal saline.

8. An article as in claim 1, wherein the article has a Young's elastic modulus of greater than or equal to 1 GPa in a dehydrated state.

9. An article as in claim 1, wherein the article has a Young's elastic modulus of less than or equal to 100 MPa and greater than or equal to 5 MPa at an equilibrium water content state.

10. An article as in claim 1, wherein the article is substantially lubricious at an equilibrium water content state.

11. An article as in claim 1, wherein the article has an average surface roughness (Ra) of less than or equal to 500 nm at an equilibrium water content state.

12. An article as in claim 1, wherein the article has a coefficient of friction of less than or equal to 0.10 at an equilibrium water content state.

13. An article as in claim 1, wherein the article comprises an osmotic agent present in the polymeric material in an amount greater than or equal to 0.05 w/w % and less than or equal to 2 w/w % versus the total article weight.

14. An article as in claim 1, wherein the osmotic agent is selected from the group consisting of phosphates, borates, sodium chloride, citrates, ethylenediaminetetraacetates, sulfites, sulfates, hyposulfites, metal oxides, selenium dioxide, selenium trioxide, selenous acid, selenic acid, nitrates, silicates, and botanic acid.

15. An article as in claim 1, wherein the first water soluble polymer is present in the article in an amount of greater than or equal to 20 w/w % and less than or equal to 95 w/w % at an equilibrium water content state.

16. An article as in claim 1, wherein the polymeric material has a water contact angle of less than or equal to 45 degrees at an equilibrium water content state.

17. An article as in claim 1, wherein the first water soluble polymer does not comprise covalent crosslinking agents.

18. An article as in claim 1, wherein the first water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

19. An article as in claim 1, wherein the polymeric material comprises a mixture comprising the first water soluble polymer and a third water soluble polymer.

20. An article as in claim 19, wherein the third water soluble polymer is selected from the group consisting of poly(vinyl alcohol), poly(acrylic acid), polyethylene glycol, poly(vinyl pyrrolidone), poly(methacrylic sulfobetaine), poly(acrylic sulfobetaine), poly(methacrylic carboxybetaine), poly(acrylic carboxybetaine), povidone, polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

21. An article as in claim 1, wherein the second water soluble polymer is selected from the group consisting of poly(vinyl alcohol), poly(acrylic acid), polyethylene glycol, or poly(vinyl pyrrolidone), poly(methacrylic sulfobetaine), poly(acrylic sulfobetaine), poly(methacrylic carboxybetaine), poly(acrylic carboxybetaine), povidone polyacrylamide, poly(N-(2-hydroxypropyl) methacrylamide), polyoxazolines, polyphosphates, polyphosphazenes, polyvinyl acetate, polypropylene glycol, poly(N-isopropylacrylamide), poly(2-hydroxymethylmethacrylate), and combinations thereof.

22. An article as in claim 1, wherein the article is configured for use with a medical device such as a catheter, a balloon, a shunt, a wound drain, an infusion port, a drug delivery device, a tube, a contraceptive device, a feminine hygiene device, an endoscope, a grafts, a pacemaker, an implantable cardioverter-defibrillator, a cardiac resynchronization device, a cardiovascular device lead, a ventricular assist device, an endotracheal tube, a tracheostomy tube, an implantable sensor, a ventilator pump, and an ophthalmic device.

23. An article as in claim 22, wherein the catheter is selected from the group consisting of central venous catheters, peripheral central catheters, midline catheters, peripheral catheters, tunneled catheters, dialysis access catheters, urinary catheters, neurological catheters, percutaneous transluminal angioplasty catheters, and peritoneal catheters.

24. An article as in claim 1, wherein the second water soluble polymer is positioned within the bulk of the first water soluble polymer.

25. An article as in claim 1, wherein less than 0.5 w/w % sorption of a therapeutic agent to the bulk of the first water-soluble polymer occurs at equilibrium water content after flushing with 5× the volume of the article with water or normal saline.

* * * * *